United States Patent
Feldstein

(10) Patent No.: US 10,392,615 B2
(45) Date of Patent: Aug. 27, 2019

(54) METHODS FOR RNA PROMOTER IDENTIFICATION

(71) Applicant: The Regents of the University of California, Oakland, CA (US)

(72) Inventor: Paul A. Feldstein, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/737,303

(22) PCT Filed: Jun. 22, 2016

(86) PCT No.: PCT/US2016/038802
§ 371 (c)(1),
(2) Date: Dec. 17, 2017

(87) PCT Pub. No.: WO2016/209989
PCT Pub. Date: Dec. 29, 2016

(65) Prior Publication Data
US 2018/0155713 A1 Jun. 7, 2018

Related U.S. Application Data

(60) Provisional application No. 62/185,060, filed on Jun. 26, 2015.

(51) Int. Cl.
| C12N 15/11 | (2006.01) |
| C12N 15/113 | (2010.01) |
| C12N 15/10 | (2006.01) |
| C12N 15/82 | (2006.01) |
| C12Q 1/6876 | (2018.01) |

(52) U.S. Cl.
CPC ........ *C12N 15/1093* (2013.01); *C12N 15/111* (2013.01); *C12N 15/8205* (2013.01); *C12Q 1/6876* (2013.01); *C12N 2310/12* (2013.01); *C12N 2310/121* (2013.01); *C12N 2320/10* (2013.01); *C12N 2330/51* (2013.01)

(58) Field of Classification Search
CPC .............. C12N 15/1093; C12N 15/111; C12N 15/8205; C12N 2310/12; C12Q 1/6876
See application file for complete search history.

(56) References Cited

U.S. PATENT DOCUMENTS

| 6,210,931 B1 * | 4/2001 | Feldstein | C12P 19/34 435/6.12 |
| 2008/0207539 A1 * | 8/2008 | Arbuthnot | C12N 15/111 514/44 A |

FOREIGN PATENT DOCUMENTS

| WO | WO-2016210321 A2 * | 12/2016 | C12N 15/1051 |

OTHER PUBLICATIONS

Chay et al. Virology 239, 413-425 (Year: 1999).*

* cited by examiner

*Primary Examiner* — Brian Whiteman
(74) *Attorney, Agent, or Firm* — O'Banion & Ritchey LLP; John P. O'Banion

(57) ABSTRACT

Provided are constructs and methods for RNA promoter identification.

14 Claims, 44 Drawing Sheets
Specification includes a Sequence Listing.

Fig. 1A-C

```
               10         20         30         40         50         60         70         80         90        100
                *          *          *          *          *          *          *          *          *          *
  1  ATACCCTGTCACCGGATGTGCTTTCCGGTCTGATGAGTCCGTGAGGACGAAACAGGACTGTCAGGTGGCCGAAAGCCACCAGTAAACTAGTGGATCCAA  100
     >>>>>>>>>>>>>>>>>>>>>>>>>>>>>>>>>>>>>>>>>>>>>>>>                                           >>>>>>>
                Hammerhead ribozyme region                                               Stuffer insertion site
                                                     >>>>>>>>>                                        >>
                                                     D8 complement                          2nd D8 complement
                                                             >>>>>
                                                             P5 complement 110        120        130        140        150        160        170        180        190        200
                *          *          *          *          *          *          *          *          *          *
 101 CAGGACTGTCAGTAGTCAAGGCGTACCAGGTAATATACCACAACGTGTGTTCTCTGTTGACTTCTCTGTTGTTGTGTCATTGGTTCCGGATCTCG  200
     >>>>>>                  >>>>>>>>>>>>>>>>>>>>>>>>>>>>>>>>>>>>>>>>>>>>>>>>>>>>>>>>>>>>>>>>>>>>>>>>
     2nd D8 complement            Hairpin catalytic core complement
           >>>>>
           2nd P5 complement
```

*Fig. 8A*

```
          210       220       230       240       250       260       270       280       290       300
           *         *         *         *         *         *         *         *         *         *
201 CATTAGCGGGCGACGGGGTATCCTGCAGGAAGCTTGGATCCGTCGACGCGGCCGCGATCGTCGACTGTAGAACTCTGAACCCTTGGCACCCGAGAATTCC
    >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
                       Multiple cloning site
                                                                              >>>>>>>>>>>>>>>>>>>>>>>
                                                                                 RT primer 1 complement 310       320       330       340       350       360       370       380       390       400
           *         *         *         *         *         *         *         *         *         *
301 AGAATTCGGCGCGGCCATACCCTGTCTCGGGTCCGGCATGGCCATCTCCACCTCCCTCGCGGTCCGACCTGGGCATCCGAAGGAGGACAGACGTCCACTCGGATGG
    >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
    Multiple cloning site     HDV negative strand ribozyme
    >
    RT primer 1 complement 410
           *
401 CTAAGGGAGAGCC 413
    >>>>>>>>>>>>>
    HDV negative strand ribozyme
```

*Fig. 8B*

```
         10         20         30         40         50         60         70         80         90        100
          *          *          *          *          *          *          *          *          *          *
  1 AGATCTAATAGCACTCACTATAGGGATCTATACCCTGTCACCGGATGTGCTTTCCGGTCTGATGAGTCCGTGAGGACGAAACAGGACTGTCAGGTGGCC 100
    >>>>>>>>>>>>>>>>                        >>>>>>>>>>>>>>>>>>>>>>>>>>>>>>>>>>>>>>>>>>>>>>>>>>>>>>>>>>>>>>
    T7 RNA promoter                         Hammerhead ribozyme region                     >>>>>>>>
                                                                                           D8 complement
                                                                                                   >>>>
                                                                                                   P5 complement 110        120        130        140        150        160        170        180        190        200
          *          *          *          *          *          *          *          *          *          *
101 GAAAGCCACCAGTAAACTGGATCAACAGGACTAGTGGATCCTAGTCAAGGGTACCAGGTAATATACCAACGTGTTTCTCTGGTTGACTTCTCT 200
    >>>>>>                                      >>>>>>>>>>>>>>>>>>>>>>>>>>>>>>>>>>>>>>>>>>>>>>>>>>>>>>>>>>
          Stuffer insertion site                Hairpin catalytic core complement
          >>>>>>>
          2nd D8 complement
               >>>>
               2nd P5 complement 210        220        230        240        250        260        270        280        290        300
          *          *          *          *          *          *          *          *          *          *
201 GTTTGTTGTGTCATTGGTTCCCGGATCTCGCATTAGCGGCGACTTGGATCCTGCAGGAAGCTTGGATCCGTCGACGCGGCCCGCGATCGTCGGACTGTAG 300
    >>                                                  >>>>>>>>>>>>>>>>>>>>>>>>>>>>>>>>>>>>>>>>>>>>>>>>>>
    Hairpin catalytic core complement                   Multiple cloning site
                                                                                            >>>>>>>>>>>>>>>
                                                                                            Primer 2 complement
```

*Fig. 10A*

```
            310        320        330        340        350        360        370        380        390        400
              *          *          *          *          *          *          *          *          *          *
301 AACTCTGAACCCTTGGCACCCGAGAATTCCAGAATTCGGGCGCGCCATACCCCTGTCGGGTCGGCATGGCATCTCCACCTCCTGGCGGTCCGACCTGGGCAT
    >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
    Multiple cloning site                                        HDV negative strand ribozyme
                       >>>>>>>>>>>>>>>>>>>>
                       RT primer 1 complement
    >>>>>>>>>
    Primer 2 complement 410        420        430        440        450        460        470        480        490        500
              *          *          *          *          *          *          *          *          *          *
401 CCGAAGGAGGACAGAGTCCACTCGGATGGCTAAGGGAGAGCCATCTAGACGCGGTTGCTGGCGTTTTTCCATAGGCTCCGCCCCCTGACGAGCATCACA
    >>>>>>>>>>>>>>>>>>>>>>>>>>>>>>>>>>>>>>>                   <<<<<<<<<<<<<<<<<<<<<<<<<<<<<<<<<<<<<<<<<
    HDV negative strand ribozyme                                              rep (pMB1)

510        520        530        540        550        560        570        580        590        600
              *          *          *          *          *          *          *          *          *          *
501 AAAATCGACGCTCAAGTCAGAGGTGGCGAAACCCGACAGGACTATAAAGATACCAGGCGTTTCCCCCTGGAAGCTCCCTCGTGCGCTCTCCTGTTCCGAC
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
    rep (pMB1)
    <<<<<<<<<<<<<<<<<<<<<
    seq2

610        620        630        640        650        660        670        680        690        700
              *          *          *          *          *          *          *          *          *          *
601 CCTGCCGCTTACCGGATACCTGTCCGCCTTTCTCCCTTCGGGAAGCGTGGCGCTTTCTCATAGCTCACGCTGTAGGTATCTCAGTTCGGTGTAGGTCGTT
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
    rep (pMB1)
```

*Fig. 10B*

```
     710        720        730        740        750        760        770        780        790        800
       *          *          *          *          *          *          *          *          *          *
701 CGCTCCAAGCTGGGCTGTGTGCACGAACCCCCCGTTCAGCCCGACCCCCGTTATCCGGTAACTATCGTCTTGAGTCCAACCCGGTAAGACACGACT 800
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
    rep (pMB1)

810        820        830        840        850        860        870        880        890        900
       *          *          *          *          *          *          *          *          *          *
801 TATCGCCACTGGCAGCAGCCACTGGTAACAGGATTAGCAGAGCGAGGTATGTAGGCGGTGCTACACAGAGTTCTTGAAGTGTGGCCTAACTACGGCTACAC 900
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
    rep (pMB1)

910        920        930        940        950        960        970        980        990       1000
       *          *          *          *          *          *          *          *          *          *
901 TAGAAGAACAGTATTTGGTATCTGCGCTCTGCTGAAGCCAGTTACCTTCGGAAAAAGAGTTGGTAGCTCTTGATCCGGCAAACAAACCACCGCTGGTAGC 1000
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
    rep (pMB1)

1010       1020       1030       1040       1050       1060       1070       1080       1090       1100
       *          *          *          *          *          *          *          *          *          *
1001 GGTGGTTTTTTTTGTTTGCAAGCAGCAGATTACGCGCAGAAAAAAAGGATCTCAAGAAGATCCTTTGATCTTTTCTACGGGGTCTGACGCTCAGTGGAACG 1100
    <<<<<<<<<<<<<<<<<<<<<<<<<<<<<<<<<<<<<<<<<<<<<<<<<<<<<<<<<<<<<<<<<<<<<<<<<<<<<<<V
    rep (pMB1)

1110       1120       1130       1140       1150       1160       1170       1180       1190       1200
       *          *          *          *          *          *          *          *          *          *
1101 AAAACTCACGTTAAGGGATTTTGGTCATGAGATTATCAAAAAGGATCTTCACCTAGATCCTTTTAAATTAAAAATGAAGTTTTAAATCAATCTAAAGTAT 1200
                                                                         <<<<<<<<<<<<<<<<<<<<<<<<<<<<
                                                                                                 ampR 1210       1220       1230       1240       1250       1260       1270       1280       1290       1300
       *          *          *          *          *          *          *          *          *          *
1201 ATATGAGTAAACTTGGTCTGACAGTTACCAATGCTTAATCAGTGAGGCACCTATCTCAGCGATCTGTCTATTTCGTTCATCCATAGTTGCCTGACTCCCC 1300
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
```

Fig. 10C

```
        1310       1320       1330       1340       1350       1360       1370       1380       1390       1400
          *         *          *          *          *          *          *          *          *          *
1301 GTCGTGTAGATAACTACGATACGGGAGGGCTTACCATCTGGGCCCCAGTGCTGCAATGATACCGCGAGACCCACGCTCACCGGCTCCAGATTTATCAGCAA 1400
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 1410       1420       1430       1440       1450       1460       1470       1480       1490       1500
          *         *          *          *          *          *          *          *          *          *
1401 TAAACCAGCCAGCCGGAAGGGCCGAGCGCAGAAGTGGTCCCTGCAACTTTATCCGCCTCCATCCAGTCTCTATTAATTGTTGCCGGGAAGCTAGAGTAAGTAG 1500
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 1510       1520       1530       1540       1550       1560       1570       1580       1590       1600
          *         *          *          *          *          *          *          *          *          *
1501 TTCGCCAGTTAATAGTTTGCGCAACGTTGTTGCCATTGCTACAGGCATCGTGGTGTCACGCTCGTCGTTTGGTATGGCTTCATTCAGCTCCGGTTCCCAA 1600
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 1610       1620       1630       1640       1650       1660       1670       1680       1690       1700
          *         *          *          *          *          *          *          *          *          *
1601 CGATCAAGGCGAGTTACATGATCCCCCATGTGTGCAAAAAAGCGGTTAGCTCCTTCGGTCCTCCGATCGTTGTCAGAAGTAAGTTGGCCGCAGTGTTAT 1700
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 1710       1720       1730       1740       1750       1760       1770       1780       1790       1800
          *         *          *          *          *          *          *          *          *          *
1701 CACTCATGGTTATGGCAGCACTGCATAATTCTCTTACTGTCATGCCATCCGTAAGATGCTTTTCTGTGACTGGTGAGTACTCAACCAAGTCATTCTGAGA 1800
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR
```

*Fig. 10D*

```
1801 ATAGTGTATGGCGACCGAGTTGCTCTTGCCCGGCGTCAATATACCGCGCCACATAGCAGAACTTTAAAAGTGCTCATCATTGGAAAACGT 1900
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 1901 TCTTCGGGGCGAAAACTCTCAAGGATCTTACCGCTGTTGAGATCCAGTTCGATGTAACCCACTCGTGCACCCAACTGATCTTTTACTTTCA 2000
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 2001 CCAGCGTTTCTGGGTGAGCAAAAACAGGAAGGCAAAATGCCGCAAAAAAGGGGACACCGAAATGTTGAATACTCATACTCTTCCTTTTTCA 2100
     <<<<<<<<<<<<<<<<<<<<<<<<<<<<<<<<<<<<<<<<<<<<<<<<<<<<<<<<<<<<<<< >>>>>>>>>
     ampR                                                             seqi
                                                                      <<<<<<<<<<<<<<<
                                                                      ampr promoter 2101 ATATTATTGAAGCATTTATCAGGGTTATTGTCTCATGAGCGGATACATATTTGAATGTATTTAGAAAAATAAACAAATAGGGGTTCCGCG 2190
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampr promoter
     >>>>>>>>>>>>>
     seqi
```

*Fig. 10E*

```
         10        20        30        40        50        60        70        80        90       100
          *         *         *         *         *         *         *         *         *         *
  1 CCTGTGGTTGGCATGCACATACAAATGGACGAACGGATAAACCTTTTCACGCCCTTTTAAATATCCGATTATTCTAATAAACGCTCTTTTCTCTTAGGTT 100
    >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
    Right border 110       120       130       140       150       160       170       180       190       200
          *         *         *         *         *         *         *         *         *         *
101 TACCCGCCAATATATCCTGTCAAACACTGATAGTTTGTGAACCATCACCCAAATCAAGTTTTTGGGGTCGAGGTGCCGTAAAGCACTAAATCGGAACCC 200
    >>>>>>>>>>>>>>>>>>>>>>>>>>>>>>>>>>>>>>>>>>>>>>>>>>>>>>>>>>>>>>>>>>>>>>>>>>>>>>>
    Right border 210       220       230       240       250       260       270       280       290       300
          *         *         *         *         *         *         *         *         *         *
201 TAAAGGGAGCCCCCGATTTAGAGCTTGACGGGGAAAGCCGGCGAACGTGGCGAGAAAGGAAGGGAAGCGGGCGCCATTCAGGCTGCG 300

310       320       330       340       350       360       370       380       390       400
          *         *         *         *         *         *         *         *         *         *
301 CAACTGTTGGGAAGGGCGATCGGTGCGGGCCTCTTCGCTATTACGCCAGCTGGCGAAAGGGGGATGTGCTGCAAGGCGATTAAGTGGGTAACGCCAGGG 400

410       420       430       440       450       460       470       480       490       500
          *         *         *         *         *         *         *         *         *         *
401 TTTTCCCAGTCACGACGTTGTAAAACGACGGCCAGTGAATTAAGAATTCGAGCTCGGTACCCGGGAAACCTCCTCGGATTCCATTGCCCAGCTAT 500
                                                                       >>>>>>>>>>>>>>>>>>>>>>>>>>>>
                                                                       CaMV 35S promoter 510       520       530       540       550       560       570       580       590       600
          *         *         *         *         *         *         *         *         *         *
501 CTGTCACTTTATTGAGAAGATAGTGGAAAAGGAAGGTGGCTCCTACAAATGCCATCGTTGAAGATAAAGGAAAGGCCATCGTTGAAGATGCCTCTGCCGAC 600
    >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
    CaMV 35S promoter
```

*Fig. 12A*

```
         610       620       630       640       650       660       670       680       690       700
          *         *         *         *         *         *         *         *         *         *
601 AGTGGTCCCAAAGATGGACCCCCACCACGAGGAGCATCGTGGAAAAAGAAGACGTTCCAACCACGTCTTCAAAGCAAGTGGATTGATGTGATATCTCCA 700
    >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
    CaMV 35S promoter 710       720       730       740       750       760       770       780       790       800
          *         *         *         *         *         *         *         *         *         *
701 CTGACGTAAGGATGACGCACAATCCCTTCGCAAGACCCTTCCTCTATATAAGGAAGTTCATTTCATTTGGAGAGGGTATACCCTGTCACCGG 800
    >>>>>>>>>>>>>>>>>>>>>>>>>>>>>>>>>>>>>>>>>>>>>>>>>>>>>>>>>>>>>>>>>>>>>>>>>>>>>>>>> >>>>>>>>
                                                                                      Hammerhead ribozyme region
    >>>>>>>>>>>>>>>>>>>>>>>>>>>>>>>>>>>>>>>>>>>>>
    CaMV 35S promoter 810       820       830       840       850       860       870       880       890       900
          *         *         *         *         *         *         *         *         *         *
801 ATGTGCTTTCCGGTCTGATGAGTCCGTGAGGACGAAACAGGACTGTCAGGTGGCCGAAAGCCACCACGTAAACTAGTGGATCCAACAGGACTGTCAGCTA 900
    >>>>>>>>>>>>>>>>>>>>>>>>>>>>>>>>>>>>>>>>>>>>>>>>>>>
    Hammerhead ribozyme region
                                                       >>>>>>>>
                                                       Stuffer insertion site
                                    >>>>>>>                         >>>>>>>>
                                    D8 complement                   2nd D8 complement
                                              >>>>>
                                              P5 complement                  >>>>>
                                                                             2nd P5 complement 910       920       930       940       950       960       970       980       990      1000
          *         *         *         *         *         *         *         *         *         *
901 GTCAAGGCGTACCAGGTAATATACCACAAGTGTGTTTCTCTGGTTGACTTTCCTGTGTTTGTGTCATTGGTTCCCGGATCTCGCATTAGCGGCGACGG 1000
    >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
    Hairpin catalytic core complement
```

*Fig. 12B*

```
        1010       1020       1030       1040       1050       1060       1070       1080       1090       1100
          *          *          *          *          *          *          *          *          *          *
1001 GGTATCCTGCAGGAAGCTTGGATCCGTCGACGCGGCCGCGATCGTCGGACTGTGAACTCTGAACCCTTGGCACCCGAGAATTCGGCGCC 1100
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Multiple cloning site                                        Primer 2 complement 1110       1120       1130       1140       1150       1160       1170       1180       1190       1200
          *          *          *          *          *          *          *          *          *          *
1101 ATACCCTGTCGGGTCGGCATGGCATCTCCACCTCCTCCGCGGTCCGACCTGGGCATCCGAAGGAGACAGAGTCCACTCGGATGGCTAAGGGAGAGCCAT 1200
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
                                                                               >>>>>>>>>>>>>>>>>>
     HDV negative strand ribozyme                                               RT primer 1 complement 1210       1220       1230       1240       1250       1260       1270       1280       1290       1300
          *          *          *          *          *          *          *          *          *          *
1201 CGAATTCGCTGAAATCACCAGTCTCTCTCTCTACAAATCTATCTCTCTCTATTTTCTCCAATAAATAATGTGTGAGTAGTTTCCCGATAAGGAAATTAGGGT 1300
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     CaMV 35S terminator                                                                                   CaMV 35S terminator 1310       1320       1330       1340       1350       1360       1370       1380       1390       1400
          *          *          *          *          *          *          *          *          *          *
1301 TCTTATAGGGTTTCGCTCATGTGTTGAGCATATAAGAAAACCCTTAGTAGTGTATTTGTAAAATACTTCTATCAATAAAATTTCTAATTCCTAAAA 1400
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     CaMV 35S terminator
```

Fig. 12C

```
       1410      1420      1430      1440      1450      1460      1470      1480      1490      1500
         *         *         *         *         *         *         *         *         *         *
1401 CCAAAATCCAGTACTAAAAATCCAGATCTCCTAAAGTCCCTATAGATCTTTGTCGTGAATATAAACCAGACACGAGACGACTAAACCTGGAGCCCAGACGC 1500
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     CaMV 35S terminator 1510      1520      1530      1540      1550      1560      1570      1580      1590      1600
         *         *         *         *         *         *         *         *         *         *
1501 CGTTCGAAGCTAGAAGTACCGCTTAGGCAGGAGGCCCGTTAGGGAAAAAGATGCTAAGGCAGGGTTGGTTACGTTGACTCCCCCCGTAGGTTTAAATA 1600
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     CaMV 35S terminator 1610      1620      1630      1640      1650      1660      1670      1680      1690      1700
         *         *         *         *         *         *         *         *         *         *
1601 TGATGAAGTGGACGGAAGGAGGAAGACAAGGAAGGATAAGGTTGCAGGCCCCTGTGCAAGGTAAGAAGATGGAAATTTGATAGAGGTACGCTACTAT 1700
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     CaMV 35S terminator 1710      1720      1730      1740      1750      1760      1770      1780      1790      1800
         *         *         *         *         *         *         *         *         *         *
1701 ACTTATACTATACGCTAAGGGAATGCTTGTATTTATACCCCTAATAACCCCTTATCAATTTAAGAAATAATCCGCATAAGCCCCCGCTTAAA 1800
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     CaMV 35S terminator 1810      1820      1830      1840      1850      1860      1870      1880      1890      1900
         *         *         *         *         *         *         *         *         *         *
1801 AATTGGTATCAGAGCCATGAATAGTTCTATGACCAAAACTCAAGAGATAAAACTCAGAAGAGTTCTTAACTCTAAAGATAAAAGATGG 1900
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     CaMV 35S terminator
```

*Fig. 12D*

```
         1910       1920       1930       1940       1950       1960       1970       1980       1990       2000
           *          *          *          *          *          *          *          *          *          *
1901 CGCGTGGCCGGCCTACAGTATGAGCGGAGAATTAAGGGAGTCACGTTATGACCCCCGCCGATGACGCGGGACAAGCCGTTTACGTTTGGAACTGACAGA 2000
         2010       2020       2030       2040       2050       2060       2070       2080       2090       2100
           *          *          *          *          *          *          *          *          *          *
2001 ACCGCAACGTTGAAGGAGCCACTCAGCCGCGGGGTTTCTGGAGTTTAATGAGCTAAGCACATACGTCAGAAACCATTATTGCGCGTTCAAAAGTCGCCTAA 2100
         2110       2120       2130       2140       2150       2160       2170       2180       2190       2200
           *          *          *          *          *          *          *          *          *          *
2101 GGTCACTACTATCAGCTAGCAAATATTTCTTGTCAAAAATGCTCCACTGACGTTCCATAAATTCCCCTCGGTATCCAATTAGAGTCTCATATTCACTCTCAAT 2200
         2210       2220       2230       2240       2250       2260       2270       2280       2290       2300
           *          *          *          *          *          *          *          *          *          *
2201 CCAAATAATCTGCACCGGATCTGGATCGTTTTCGCATGATTGAACAAGATGGATTGCACGCAGGTTCTCCGGCCGCTTGGGTGGAGAGGCTATTCGGCTAT 2300
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
                                                  neomycin phosphotransferase II
         2310       2320       2330       2340       2350       2360       2370       2380       2390       2400
           *          *          *          *          *          *          *          *          *          *
2301 GACTGGGCACAACAGACAATCGGCTGCTCTGATGCCGCCGTGTTCCGGCTGTCAGCGCAGGGGCGCCCGGTTCTTTTTGTCAAGACCGACCTGTCCGGTG 2400
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
                              neomycin phosphotransferase II
         2410       2420       2430       2440       2450       2460       2470       2480       2490       2500
           *          *          *          *          *          *          *          *          *          *
2401 CCCTGAATGAACTGCAGGACGAGGCAGCGCGGCTATCGTGGCTGGCCACGACGGGCGTTCCTTGCGCAGCTGTGCTCGACGTTGTCACTGAAGCGGGAAG 2500
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
                               neomycin phosphotransferase II
```

*Fig. 12E*

```
         2510      2520      2530      2540      2550      2560      2570      2580      2590      2600
            *         *         *         *         *         *         *         *         *         *
2501 GGACTGGCTGCTATTGGGCGAAGTGCCGGGGCAGGATCTCCTGTCATCTCACCTTGCCGAGAAAGTATCCATCATGGCTGATGCAATGCGGCGG 2600
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
      neomycin phosphotransferase II 2610      2620      2630      2640      2650      2660      2670      2680      2690      2700
            *         *         *         *         *         *         *         *         *         *
2601 CTGCATACGCTTGATCGGGCTACCTGCCCATTCGACCACCAAGCGAAACATCGCATCGAGCGAGCACGTACTCGGATGGAAGCCGGTCTTGTCGATCAGG 2700
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
      neomycin phosphotransferase II 2710      2720      2730      2740      2750      2760      2770      2780      2790      2800
            *         *         *         *         *         *         *         *         *         *
2701 ATGATCTGGACGAAGAGCATCAGGGGCTCGCGCCAGCCGAACTGTTCGCCAGGCTCAAGGCGCGCATGCCCGACGGCGATGATCTCGTCGTGACCCATGG 2800
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
      neomycin phosphotransferase II 2810      2820      2830      2840      2850      2860      2870      2880      2890      2900
            *         *         *         *         *         *         *         *         *         *
2801 CGATGCCTGCTTGCCGAATATCATGGTGGAAAATGGCCGCTTTTCTGGATTCATCGACTGTGGCCGGCTGGGTGTGGCGGACCGCTATCAGGACATAGCG 2900
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
      neomycin phosphotransferase II 2910      2920      2930      2940      2950      2960      2970      2980      2990      3000
            *         *         *         *         *         *         *         *         *         *
2901 TTGGCTACCCGTGATATTGCTGAAGAGCTTGGCGGCGAATGGGCTGACCGCTTCCTCGTGCTTTACGGTATCGCCGCTCCCGATTCGCAGCGCATCGCCT 3000
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
      neomycin phosphotransferase II
```

*Fig. 12F*

```
        3010      3020      3030      3040      3050      3060      3070      3080      3090      3100
          *         *         *         *         *         *         *         *         *         *
3001 TCTATCGCCTTCTTCTGACGAGTTCTTCTGAGCGGGACTCTGGGGTTCGAAATGACCGACCAAGCGCGACGCCCAACCTGCCATCACGAGATTTCGATTCCACC
     >>>>>>>>>>>>>>>>>>>>>>>>>>>>>>>>>
     neomycin phosphotransferase II 3110      3120      3130      3140      3150      3160      3170      3180      3190      3200
          *         *         *         *         *         *         *         *         *         *
3101 GCCGCCTTCTATGAAAGGTTGGGCTTCGGAATCGTTTTCCGGGACGCCGGCTGGATGATCCTCCAGCGCGGGGATCTCATGCTGGAGTTCTTCGCCCACG 3210      3220      3230      3240      3250      3260      3270      3280      3290      3300
          *         *         *         *         *         *         *         *         *         *
3201 GGATCTCTGCGGGAACAGGCGGTCGAAGGTGCCGATATCATTACGACAGCAACGGCCCGACAAGCACAACGCCACGATCCTGAGCGCGACAATGATCGCGGC 3310      3320      3330      3340      3350      3360      3370      3380      3390      3400
          *         *         *         *         *         *         *         *         *         *
3301 GTCCACATCAACGGGTCGGCGGCGACTGCCCAGGCAAGACCGAGATGATCTTGCTGCGTTCGGATATTTTCGTGGAGTTCCCGCCACAGA 3410      3420      3430      3440      3450      3460      3470      3480      3490      3500
          *         *         *         *         *         *         *         *         *         *
3401 CCCGGATGATCCCCCGATCGTTCAAACATTTGGCAATAAACATTTGGCAATAAAGTTTCTTAAGATTGAATCCTGTTGCCGGTCTCTTGCGATGATTATCATATAATTTCTGTTGAA 3510      3520      3530      3540      3550      3560      3570      3580      3590      3600
          *         *         *         *         *         *         *         *         *         *
3501 TTACGTTAAGCATGTAATAATTAACATGTAAATGCATGACGTTATTTATGAGATGGGTTTTTATGATTAGAGTCCCGCAATTATACATTTAATACGCGATA 3610      3620      3630      3640      3650      3660      3670      3680      3690      3700
          *         *         *         *         *         *         *         *         *         *
3601 GAAAACAAAATATAGCGCGCAAACTAGGATAAATTATCGCGCGCGGTGTCAGATATCTATGTTACTAGATCGGGACTGTAGGCGGGCCCCTCACTGGTGAAAAGA
```

*Fig. 12G*

```
              3710      3720      3730      3740      3750      3760      3770      3780      3790      3800
                *         *         *         *         *         *         *         *         *         *
3701 AAAACCACCCCAGTAGTACATTAAAAACGTCCGCAATGTGTTATTAAGTCGTCTAAGCGTCAATTTGTTTACACCACAATATCCTGCCACCAGCCAGCCAA 3800
     <<<<<<<<<<<<<<<<<<<<<<<<<<<<<<<<<<<<<<<<<<<<<<<<<<<<<<<<<<<
     Left border 3810      3820      3830      3840      3850      3860      3870      3880      3890      3900
                *         *         *         *         *         *         *         *         *         *
3801 CAGCTCCCCCGACCGGCAGCTCGGCACAAAATCACCACCTCGATACAGGCAGCCCATCAGTCCGGGACGGCGTCAGCGGGAGAGCCGTTGTAAGGCGGCAGA 3900
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<

3910      3920      3930      3940      3950      3960      3970      3980      3990      4000
                *         *         *         *         *         *         *         *         *         *
3901 CTTTGCTCATGTTACCGATGCTATTCGGAAGAACGGCAACTAAGCTGCCGGGTTTGAAACACGGATGATCTCGCGGAGGGTAGCATGTTGATTGTAACGA 4000

4010      4020      4030      4040      4050      4060      4070      4080      4090      4100
                *         *         *         *         *         *         *         *         *         *
4001 TGACAGAGCGTTGCTGCCTGTGATCAAATATCATCTCCCTCGCAGAGATCCGAATTATCAGCCTTCTCTTATTCATTTCTCGCTTAACCGTGACAGAGTAGA 4100

4110      4120      4130      4140      4150      4160      4170      4180      4190      4200
                *         *         *         *         *         *         *         *         *         *
4101 CAGGCTGTCTCGCGGCCGAGGGGCGCAGCCCCTGGGGGATGGGAGGCCCGCGTTAGCGGGATGGGAGGCCCGCGTTAGCGGGAGGGTTCGAGAAGGGGGCACCCCCTTCGGC 4200
                                                                        OriV from pRK2

4210      4220      4230      4240      4250      4260      4270      4280      4290      4300
                *         *         *         *         *         *         *         *         *         *
4201 GTGCGCGGTCACGCGCACAGGGCGCAGCCCTGGTTAAAACAAGCCCTGGTTAAATATTGGTTTAAAAGCAGGTTAAAAGACAGGTTAGCGGTGGCCGAAAA 4300
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     OriV from pRK2
```

*Fig. 12H*

```
          4310      4320      4330      4340      4350      4360      4370      4380      4390      4400
            *         *         *         *         *         *         *         *         *         *
4301  ACGGGCGGAAACCCTTGCAAATGCTGGATTTTCTGCCTGTGGACAGCCCCTCAAATGTCAATAGTGCGCCCCTCATCTGTCAGCACTCTGCCCTCAAG
      <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
      OriV from pRK2

4410      4420      4430      4440      4450      4460      4470      4480      4490      4500
            *         *         *         *         *         *         *         *         *         *
4401  TGTCAAGGATCGCGCCCCTCATCTGTCAGTAGTCGCGCCCCTCAAGTGTCAATACCGCAGGGCACTTATCCCCAGGCTTGTCCACATCATCTGTGGGAAA
      <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
      OriV from pRK2

4510      4520      4530      4540      4550      4560      4570      4580      4590      4600
            *         *         *         *         *         *         *         *         *         *
4501  CTCGCGTAAAATCAGGCGTTTTCGCCGATTTGCGAGGCTGGCCAGCTCCACGTCGCCGGCCGAAATCGAGCCTGCCCCTCATCGTCAGGGCCTTCATCCGTCAACGCCGCCGG
      <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
      OriV from pRK2

4610      4620      4630      4640      4650      4660      4670      4680      4690      4700
            *         *         *         *         *         *         *         *         *         *
4601  GTGAGTCGGCCCCTCAAGTGTCAACGTCAACGTCCGCCCCTCATCTGTCAGTGAGGGCCAAGTTTTCCGCGAGGTATCCACAACGCCGGCGGCCGGTGTCTCGC
      <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
      OriV from pRK2

4710      4720      4730      4740      4750      4760      4770      4780      4790      4800
            *         *         *         *         *         *         *         *         *         *
4701  ACACGGCTTCGACGGCGTTTCTGGCGCGTTTGCAGGGCCATAGACGCGCCCAGCGCCAGCCCCAGCGGGCGAGGGCAACCAGCCCGGTGAGCGTCGGAAAGGCGCTC
      <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
      OriV from pRK2
```

*Fig. 12I*

```
      4810      4820      4830      4840      4850      4860      4870      4880      4890      4900
        *         *         *         *         *         *         *         *         *         *
4801 GGTCTTGCCTTGCTCGTCGGTGATGTACACTAGTCGCTGGCTGCTGGCTGTGAACCCAGCCGGAACTGACCCTAGCCGTTTGCAATGCACCAGGT 4900
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
                                                                             trfA 4910      4920      4930      4940      4950      4960      4970      4980      4990      5000
        *         *         *         *         *         *         *         *         *         *
4901 CATCAATTGACCCAGGCGTGTTCCACCAGGCCGCTGCCTGCCAACTCTTCGCAGGCCTTCGCCGACCTGCTCGCGCACTTCTTCACGCGGGTGGAATCCGA 5000
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     trfA 5010      5020      5030      5040      5050      5060      5070      5080      5090      5100
        *         *         *         *         *         *         *         *         *         *
5001 TCCGCACATGAGGCGGAAGGTTTCCAGCTTGAGCGGTACGGCGGGTCTCCCGGTGGTGCGAGCTGAAATAGTCGAACATCCGTCGGCCGTCGGCGACAGCTTGCGG 5100
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     trfA 5110      5120      5130      5140      5150      5160      5170      5180      5190      5200
        *         *         *         *         *         *         *         *         *         *
5101 TACTTCTCCCATATGAATTCGTGTAGTGGTCGCCAGCAGCAAAACAGCACGACGATTTCCTGTCGATCAGGACCTGGCAACGGGACGTTTCTTGCCACGGT 5200
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     trfA 5210      5220      5230      5240      5250      5260      5270      5280      5290      5300
        *         *         *         *         *         *         *         *         *         *
5201 CCAGGACGCGGAAGCGGTGCAGCAGCACCGATTCCAGGTGCCCAACGCGGTCGGACGTGAAGCCCATCGCCGTGCCTGTAGGCGCGACAGGCATTC 5300
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     trfA
```

*Fig. 12J*

```
          5310        5320        5330        5340        5350        5360        5370        5380        5390        5400
            *           *           *           *           *           *           *           *           *           *
5301  CTCGGCCTTCGTGTAATACCGGCCATTGATCGACCAGGTCCTGGCAAAGCTCGTAGAACGTGAAGGTGATCGGCTCGCCGATAGGGGTGCGCTTC  5400
      vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
      trfA
            *           *           *           *           *           *           *           *           *           *
          5410        5420        5430        5440        5450        5460        5470        5480        5490        5500
5401  GCGTACTCCAACACCTGCTGCCACACCAGTTCGTCATCGTCGGGCCCGCAGCTCGTAGGTGATCTTCACGTCCTTGTTGACGTGGAAAAATGA  5500
      vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
      trfA
            *           *           *           *           *           *           *           *           *           *
          5510        5520        5530        5540        5550        5560        5570        5580        5590        5600
5501  CCTTGTTTGCAGGCGCCTCGCGCGGGATTTTCTTGTTGCGCGTGGTGAACAGGGCAGAGCGGGCCGTGTCGTTTGGCATCGCTCGCATCGTGTCCGGCCA  5600
      vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
      trfA
            *           *           *           *           *           *           *           *           *           *
          5610        5620        5630        5640        5650        5660        5670        5680        5690        5700
5601  CGGCGCAATATCGAACAAGGAAAGCTGCATTTCCTTGAATCTGCTGTGTTTCAGCAACGCGGCCGTTGGCCTGCCTGCTGACCTGTTTTGCCAGG  5700
      vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
      trfA
            *           *           *           *           *           *           *           *           *           *
          5710        5720        5730        5740        5750        5760        5770        5780        5790        5800
5701  TCCTCGCCGGCGGGTTTTTCGCTTCTTGGTCGTCGTCATAGTTCCTCGCGCTGTGTCGATGGTCATCGACTTCGCCAAACCTGCCGCCTCCTGTTCGAGACGACGCG  5800
      vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
      trfA
```

*Fig. 12K*

```
            5810      5820      5830      5840      5850      5860      5870      5880      5890      5900
              *         *         *         *         *         *         *         *         *         *
5801  AACGCTCCACGGGCGGGCGATGCCGCGGGGCAGGGGAGCCAGTTGCACGCTTGCCGTAGCTTGCTGGACCATCGAGCCGAC  5900
      <<<<<<<<<<<<<<<<<<<<<<<<<<<<<<<<<<<<<<<<<<<<<<<<<<<<<<<<<<<<<<<<<<<<<<<<<<<<<<<<
      trfA 5910      5920      5930      5940      5950      5960      5970      5980      5990      6000
              *         *         *         *         *         *         *         *         *         *
5901  GGACTGGAAGGTTTCGCGGGGCGCACGCATGACGGTGCGGCTTGCGATCCTCCGGCATCCTCCGGAAAACCCCGTCGATCAGTTCTTGCCTGTAT  6000
      <<<<<<<<<<<<<<<<<<<<<<<<<<<<<<<<<<<<<<<<<<<<<<<<<<<<<<<<<<<<<<<<<<<<<<<<<<<<<<<<
      trfA 6010      6020      6030      6040      6050      6060      6070      6080      6090      6100
              *         *         *         *         *         *         *         *         *         *
6001  GCCTTCCGGTCAAACGTCGATTCATTCACCCTCCTTGCGGGATTGCCCCGACTCACGCCGGGGCAATGTGCCCTTATTCCTGATTTGACCCGCCTGGTG  6100
      <<<<<<<<<<<<<<<<<<<<<<<<<<<<<<
      trfA 6110      6120      6130      6140      6150      6160      6170      6180      6190      6200
              *         *         *         *         *         *         *         *         *         *
6101  CCTTGGTGTCCAGATAATCGGGCAATTCACCTTATCGGGCAATGAAGTCGGTCCCGTCGGTCTCGTCCTTCTCGTACTTGGTATTCCGAATCTTGCCTGCAC  6200

6210      6220      6230      6240      6250      6260      6270      6280      6290      6300
              *         *         *         *         *         *         *         *         *         *
6201  GAATACCAGCGACCCCCTTGCCCAAATACTTGCCGTGGGCCTGAGAGCCAAAAACACTTGATGCGGAAGAAGTCGGTGCGCTCCTGCTTGTCGCCG  6300

6310      6320      6330      6340      6350      6360      6370      6380      6390      6400
              *         *         *         *         *         *         *         *         *         *
6301  GCATCGTTGCGCCACATCTAGTACTAAAACAATTCATCCAGTAAAATATAATATTTTATTTTCTCCCAATCAGGCTTGATCCCCAGTAAGTCAAAAAAT  6400
      <<<<<<<<<<<<<<<<<<<<<<<<<<<<<<<<<<<<<<<<<<<<<<<<<<<<<<<<<<<<<<<<<<<<<<<<<<<<<<<<
                                    neomycin phosphotransferase III
```

*Fig. 12L*

```
        6410        6420        6430        6440        6450        6460        6470        6480        6490        6500
          *           *           *           *           *           *           *           *           *           *
6401 AGCTCGACATACTGTTCTTCCCGATATCCTCCCTGATCGACCGGACGCAGAAGGCAATGTCATACCACTTGTCCGCCCTGCGCTTCTCCCAAGATCAA
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     neomycin phosphotransferase III 6510        6520        6530        6540        6550        6560        6570        6580        6590        6600
          *           *           *           *           *           *           *           *           *           *
6501 TAAAGCCACTTACTTTGCCATCTTTCACAAAGATGTTGCTGTCTCCCAGGTCGCCGTGGGAAAAGACAAGTTCCTCTTCGGGCTTTTCCGTCTTTAAAAA
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     neomycin phosphotransferase III 6610        6620        6630        6640        6650        6660        6670        6680        6690        6700
          *           *           *           *           *           *           *           *           *           *
6601 ATCATACAGCTCGCGCGGATCTTTAAATGGAGTGTCTTCTTCCCAGTTTTCGCAAATCCACATCGGCCAGATCGTTATTCAGTAAGTAATCCAATTCGGCT
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     neomycin phosphotransferase III 6710        6720        6730        6740        6750        6760        6770        6780        6790        6800
          *           *           *           *           *           *           *           *           *           *
6701 AAGCGGGTGTCTAAGCTATTCGTATAGGGACAACAATCCGATATGTCGATGGAGTGAAAGAGCCTGATGATGCACTCCGCATACAGCTCGATAATCTTTTCAGGGC
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     neomycin phosphotransferase III 6810        6820        6830        6840        6850        6860        6870        6880        6890        6900
          *           *           *           *           *           *           *           *           *           *
6801 TTTGTTCATCTTCATACTCTTCCGAGCAAAGGACGCGCCATCGGCCCTCACTCATGAGCAGATTGCTCCAGCCATCATGCCGTTCAAAGTGCAGGACCTTTGG
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     neomycin phosphotransferase III
```

*Fig. 12M*

```
              6910       6920       6930       6940       6950       6960       6970       6980       6990       7000
                *          *          *          *          *          *          *          *          *          *
      6901 AACAGGCAGCTTTCCTTCCAGCCATAGCATCATGTCCTTTCCCGTTCCACATCATAGGTGGTCCCTTTATACCGGCTGTCCGTCATTTTAAATATAGG 7000
           <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
              neomycin phosphotransferase III 7010       7020       7030       7040       7050       7060       7070       7080       7090       7100
                *          *          *          *          *          *          *          *          *          *
      7001 TTTTCATTTTCTCCACCAGCTTATATACCTTAGCAGGAGACATTCCTTCCGTATCTTTACGCAGCGGTATTTTTCGATCAGTTTTTCAATTCCGGGTG 7100
           <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
              neomycin phosphotransferase III 7110       7120       7130       7140       7150       7160       7170       7180       7190       7200
                *          *          *          *          *          *          *          *          *          *
      7101 ATATTCTCATTTTAGCCATTTATTATTCCCTCCTTTTTCTACAGTATTTAAAGATACCCCAAGAAGCTAATTATAACAGACGAACTCCAATTCACTG 7200
           <<<<<<<<<<<<<<<<<<
              neomycin phosphotransferase III 7210       7220       7230       7240       7250       7260       7270       7280       7290       7300
                *          *          *          *          *          *          *          *          *          *
      7201 TTCCTTGCATTCTAAAACCTTAAATACCAGAAATCAGCTTTTTCAAAGTTGTTTTCAAAGTTGGCGTATAACATAGTATCGACGGAGCCGATTTGAAAC 7300

7310       7320       7330       7340       7350       7360       7370       7380       7390       7400
                *          *          *          *          *          *          *          *          *          *
      7301 CACAATTATGGGTGATGCTGCCAACTTACTGATTTAGTGTATGATGGGTGTTTTTGAGGTGCTCCAGTGGCTTCTGTTTCTATCAGCGTGTCCCTGTTC 7400

7410       7420       7430       7440       7450       7460       7470       7480       7490       7500
                *          *          *          *          *          *          *          *          *          *
      7401 AGCTACTGACGGGTGGTGCGTAACGGCAAAAGCACCGCCGGACATCAGCGCTATCTCTGCTCTCACTGCCGTAAAACATGGCAAGTTCACTTAC 7500

7510       7520       7530       7540       7550       7560       7570       7580       7590       7600
                *          *          *          *          *          *          *          *          *          *
      7501 ACCGCTTCTCAACCCGGTACGCACCAGAAATCATTGATATGCCATGAATGCCGTTGATGCCGGGCAACAGCCCGCATTATGGGCGTTGCCTCAACA 7600
```

Fig. 12N

```
         7610      7620      7630      7640      7650      7660      7670      7680      7690      7700
           *         *         *         *         *         *         *         *         *         *
7601 CGATTTTACGTCACTTAAAAAACTCAGGCCGCAGTCGGTAACTATGCGGTGTGAAATACCGCACAGATGCGTAAGGAGAAAATACCGCATCAGGCGCTCT 7700
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
                                              ColE1 ori from pBR322

7710      7720      7730      7740      7750      7760      7770      7780      7790      7800
           *         *         *         *         *         *         *         *         *         *
7701 TCCGCTTCCTCGCTCACTGACTCGCTGCGCTCGGTCGTTCGGCTGCGGCGAGCGGTATCAGCTCACTCAAAGGCGGTAATACGGTTATCCACAGAATCAG 7800
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     ColE1 ori from pBR322

7810      7820      7830      7840      7850      7860      7870      7880      7890      7900
           *         *         *         *         *         *         *         *         *         *
7801 GGGATAACGCAGGAAAGAACATGTGAGCAAAAGGCCAGCAAAAGGCCAGGAACCGTAAAAAGGCCGCGTTGCTGGCGTTTTTCCATAGGCTCCGCCCCCC 7900
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     ColE1 ori from pBR322

7910      7920      7930      7940      7950      7960      7970      7980      7990      8000
           *         *         *         *         *         *         *         *         *         *
7901 TGACGAGCATCACAAAAATCGACGCTCAAGTCAGAGGTGGCGAAACCCGACAGGACTATAAAGATACCAGGCGTTTCCCCCTGGAAGCTCCCTCGTGCGC 8000
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     ColE1 ori from pBR322

8010      8020      8030      8040      8050      8060      8070      8080      8090      8100
           *         *         *         *         *         *         *         *         *         *
8001 TCTCCTGTTCCGACCCTGCCGCTTACCGGATACCTGTCCGCCTTTCTCCCTTCGGGAAGCGTGGCGCTTTCTCATAGCTCACGCTGTAGGTATCTCAGTT 8100
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     ColE1 ori from pBR322
```

*Fig. 12O*

```
        8110      8120      8130      8140      8150      8160      8170      8180      8190      8200
          *         *         *         *         *         *         *         *         *         *
8101 CGGGTGTAGGTCGTTCGCTCCAAGCTGGGCTGTGTGCACGAACCCCCCGTTCAGCCCGACCGCTGCGCCTTATCCGGTAACTATCGTCTTGAGTCCAACCC
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     ColE1 ori from pBR322

8210      8220      8230      8240      8250      8260      8270      8280      8290      8300
          *         *         *         *         *         *         *         *         *         *
8201 GGTAAGACACGACTTATCGCCACTGGCAGCAGTAACCTCGCGCATACAGCCGGGCAGTGACGTCATCGTCTGCGCGGAAATGACGGGCCCCGGCGCC
     >>>>>>>>>>>>>>>>>>>>>>>>>>>>>>>>>>>>>>>>>
     ColE1 ori from pBR322

8310
          *
8301 AGATCTGGGGGAAC 8313
```

*Fig. 12P*

```
  1 GGCCTAACTGGCCTCAATATTGGCCATTAGCCATATATTCATTGGTTATATAGCATAAATCAATATTGGCTATTGGCCATTGCATACGTTGTATCTATA 100
                   CMV promoter
101 TCATAATATGTACATTTATATTGGCTCATGTCCAATATGACCGCCATGTTGGCATTGATTATTGACTAGTTATTAATAGTAATCAATTACGGGGTCATTA 200
    CMV promoter
201 GTTCATAGCCCATATATGGAGTTCCGCGTTACATAACTTACGTCAATAATGACGTATGTTCCCATAGTAACGCCAATAGGGACTTTCCATTGACGTCAATGGGTGGAGTATTTACGGTAAACTGCCCACTTGGCAGTACATCAAGTGTATCA 300
    CMV promoter
301 CGTATGTTCCCATAGTAACGCCAATAGGGACTTTCCATTGACGTCAATGGGTGGAGTATTTACGGTAAACTGCCCACTTGGCAGTACATCAAGTGTATCA 400
    CMV promoter
401 TATGCCAAGTCCGCCCCCTATTGACGTCAATGACGGTAAATGGCCCGCCTGGCATTATGCCCAGTACATGACCTTACGGGACTTTCCTACTTGGCAGTAC 500
    CMV promoter
```

*Fig. 14A*

```
      510        520        530        540        550        560        570        580        590        600
       *          *          *          *          *          *          *          *          *          *
501 ATCTACGTATTAGTCATCGCTATTACCATGGTGATGCGGTTTTGGCAGTACACCAATGGGCGTGGATAGCGGTTTGACTCACGGGGATTTCCAAGTCTCC
    >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
    CMV promoter 610        620        630        640        650        660        670        680        690        700
       *          *          *          *          *          *          *          *          *          *
601 ACCCCATTGACGTCAATGGGAGTTTGTTTTGGCACCAAAATCAACGGGACTTTCCAAAATGTCGTAATAACCCCGCCCGTTGACGCAAATGGGCGGTAG
    >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
    CMV promoter 710        720        730        740        750        760        770        780        790        800
       *          *          *          *          *          *          *          *          *          *
701 GCGTGTACGGTGGGAGGTCTATATAAGCAGAGCTCGTTTAGTGAACCGTCAGATCACTAGAAGCTTTATTGCGGTAGTTTATCACAGTTAAATTGCTAAC
    >>>>>>>>>>>>>>>>>>>>>>>>>>>>>>>>>>>>>
    CMV promoter 810        820        830        840        850        860        870        880        890        900
       *          *          *          *          *          *          *          *          *          *
801 GCAGTCAGTGGGCCTCGGGCGGCCCAAGCTTGGCAATCCGGTACTGTTGGTAAAGCCACCATACCCTGTCACCGGATGTGCTTTCCGGTCTGATGAGTCCGT
                                                                              >>>>>>>>>>>>>>>>>>>>>>>>>>>>>
                                                                              Hammerhead ribozyme region 910        920        930        940        950        960        970        980        990       1000
       *          *          *          *          *          *          *          *          *          *
901 GAGGACGAAACAGGACTGTCAGTTCAGGTGGCCGAAAGCCACCACGTAAACTAGTGGATCCAACAGGACTGTCAGCTAGTCAGCTACCAGGTAATATACCAC
    >>>>>>>>>>>>>>>>>>>>        Stuffer insertion site                     Hairpin catalytic core complement
    Hammerhead ribozyme region  >>>>>>>>>>>
    >>>>>>>>>                   2nd D8 complement
    D8 complement               >>>>>
    >>>>>                                                                   2nd P5 complement
    P5 complement
```

*Fig. 14B*

```
        1010      1020      1030      1040      1050      1060      1070      1080      1090      1100
          *         *         *         *         *         *         *         *         *         *
1001 AACGTGTGTTCTCTGTTGACTTCTCTGTGTTGTGTCATTGGTTCCCGGATCTCGCATTAGCGGCGACGGGGTATCCTGCAGGAAGCTTGGATCCGT 1100
     >>>>>>>>>>>>>>>>>>>>>>>>                                                         >>>>>>>>>>>>>>>>
     Hairpin catalytic core complement                                                Multiple cloning site 1110      1120      1130      1140      1150      1160      1170      1180      1190      1200
          *         *         *         *         *         *         *         *         *         *
1101 CGACGCGGGCCGCGGATCGTCGGACTGTAGAACTCTGAACCCTTGGCACCCGAGAATTCCAGAATTCGGCGCGCCATACCCTGTCGGGTCGGCATGGCATCT 1200
     >>>>>>>>>>>>>>>>>>>>>>>>>>>>>>>>>>>>>>>>>>>>>>>>>>>>>>>>>>>>>>>>>>>>>>>>>>>>>>>>>>  >>>>>>>>>>>>>
     Multiple cloning site                                                                HDV negative strand ribozyme
                                           >>>>>>>>>>>>>>>>>>>>>>>>
                                           RT primer 1 complement
                 >>>>>>>>>>>>>>>>>>>>>>>
                 Primer 2 complement 1210      1220      1230      1240      1250      1260      1270      1280      1290      1300
          *         *         *         *         *         *         *         *         *         *
1201 CCACCTCCTCGCGGTCCGACCTGGGCATCCGAAGGAGGACAGACGTCCACTCGGATGGCTAAGGGAGAGCCAGGCCGCGACTCTAGAGTCGGGGGCCG 1300
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     HDV negative strand ribozyme 1310      1320      1330      1340      1350      1360      1370      1380      1390      1400
          *         *         *         *         *         *         *         *         *         *
1301 GCCGCTTCGAGCAGACATTGATAAGATACATTGATGAGTTTGGACAACCACAACTAGAATGCAGTGAAAAAAATGCTTTATTTGTGAAATTTGTGATGCT 1400
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     polyA signal sequence
```

*Fig. 14C*

```
       1410      1420      1430      1440      1450      1460      1470      1480      1490      1500
         *         *         *         *         *         *         *         *         *         *
1401 ATTGCTTTATTGTAACCATTATAAGCTGCAATAAACAAGTTAACAACAATTGCATTCATTTTATGTTTCAGGTTCAGGGGAGGTGTGGGAGGTTT 1500
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     polyA signal sequence 1510      1520      1530      1540      1550      1560      1570      1580      1590      1600
         *         *         *         *         *         *         *         *         *         *
1501 TTTAAGCAAGTAAAACCTCTACAAATGTGGTAAAATCGATAAGGATCCGTTTGCGTATTGGGCGCTCTTCCGCTTGATCTGCGCAGCACCATGGCCTGAA 1600
     >>>>>>>>>>>>>>>>>>>>>>>>>>>>>                                                >>>>>>>>>>>>>>>>>>>>>
     polyA signal sequence                                                        SV40 early enhancer/promoter 1610      1620      1630      1640      1650      1660      1670      1680      1690      1700
         *         *         *         *         *         *         *         *         *         *
1601 ATAACCCTCTGAAAGAGGAACTTGGTTAGCTACCTTCTGAGGCGGAAAGAACCAGCTGTGGAATGTGTGTCAGTTAGGGTGTGGAAAGTCCCCAGGCTCCC 1700
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     SV40 early enhancer/promoter 1710      1720      1730      1740      1750      1760      1770      1780      1790      1800
         *         *         *         *         *         *         *         *         *         *
1701 CAGCAGGCAGAAGTATGCAAAGCATGCATCTCAATTAGTCAGCAACCAGGTGTGGAAAGTCCCCAGCAGGCAGAAGTATGCAAAGCATGCA 1800
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     SV40 early enhancer/promoter 1810      1820      1830      1840      1850      1860      1870      1880      1890      1900
         *         *         *         *         *         *         *         *         *         *
1801 TCTCAATTAGTCAGCAACCATAGTCCCGCCCCTAACTCCGCCCATCCCGCCCCTAACTCCGCCCAGTTCCGCCCATTCTCCGCCCATGGCTGACTAATT 1900
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     SV40 early enhancer/promoter
```

*Fig. 14D*

```
      1910      1920      1930      1940      1950      1960      1970      1980      1990      2000
        *         *         *         *         *         *         *         *         *         *
1901 TTTTTTAATTTATGCAGAGGCCGAGGCCGCCTCTGAGCTCTGAGCTATTCCAGAAGTAGTGAGGAGGCTTTTTTGGAGGCCTAGGCTTTTTGCAAAAAGCTCG 2000
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     SV40 early enhancer/promoter 2010      2020      2030      2040      2050      2060      2070      2080      2090      2100
        *         *         *         *         *         *         *         *         *         *
2001 ATTCTTCTGACACTAGCGCCACCATGAAAGAAGCCCGAACTCACCGCTACCAGCGTTGAAAAATTTCTCATCGAGAAGTTCGACAGTGTGAGCGACCTGAT 2100
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
                         hygR 2110      2120      2130      2140      2150      2160      2170      2180      2190      2200
        *         *         *         *         *         *         *         *         *         *
2101 GCAGTTGTGTCGGAGGGCGAAGAGAGCCGAGCCCTTCAGCTTCGATGTCGGGGACGCGCTATGTACTGCGGGTGAATAGCTGCGCTGATGGCTTCTACAAA 2200
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     hygR 2210      2220      2230      2240      2250      2260      2270      2280      2290      2300
        *         *         *         *         *         *         *         *         *         *
2201 GACCGGCTACGTGTACCGGCCACTTCGCCAGCGCTGCACTACCATCCCGAAGTGTGTGGACATCGGCGAGTTCAGCGGAGAGCCTGACATACTGCATCAGTA 2300
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     hygR 2310      2320      2330      2340      2350      2360      2370      2380      2390      2400
        *         *         *         *         *         *         *         *         *         *
2301 GACGCGCCAAGGCGTTACTCTCCAAGACCTCCCCGAAACAGAGCTGCCTGCTGTGTTACAGCCTGTGCCGAAGCTATGATGATGCTATTGCCGCCGCCGA 2400
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     hygR
```

*Fig. 14E*

```
          2410      2420      2430      2440      2450      2460      2470      2480      2490      2500
            *         *         *         *         *         *         *         *         *         *
2401 CCTCAGTCAAAACCAGCGGCTTCGGCCCAATTCGGGCCCAGTACACAAACCTGGCCAGCCATTTGCGCCATTTGCGCCATTGCTGATCCCATGTC
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     hygR 2510      2520      2530      2540      2550      2560      2570      2580      2590      2600
            *         *         *         *         *         *         *         *         *         *
2501 TACCACTGGGCAGACCGTGATGGACGACACCGTGTCCGCCAGCGTAGCTCAAGCCCTGGACGAACTGATGCTGTGGGCCGAAGACTGTCCCGAGGTGCCGCC
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     hygR 2610      2620      2630      2640      2650      2660      2670      2680      2690      2700
            *         *         *         *         *         *         *         *         *         *
2601 ACCTCGTCATGCCGACTTCGGCCAGCAACATCCTGACCGACAACGCGATCACCGGCCGTAATCGACTGGTCCGAAGCTATGTTCGGGGACAGTCA
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     hygR 2710      2720      2730      2740      2750      2760      2770      2780      2790      2800
            *         *         *         *         *         *         *         *         *         *
2701 GTACGAGGTGGCCAACATCTTTCTGCGGCGCCCTGGCTGCCTGGCTTGCATGGAGCAGCAGACTCGCTACTTCGAGCGCCGGCCATCCCGAGCTGGCCGCAGC
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     hygR 2810      2820      2830      2840      2850      2860      2870      2880      2890      2900
            *         *         *         *         *         *         *         *         *         *
2801 CCTCGTCTGCGAGCCCTACATGCTGCCGATCGGCCTGGATCAGCTCTACCAGAGCCTCGTGACGGCAACTTCGACGATGCTGCCTGGGCTCAAGGCCCGCT
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     hygR
```

*Fig. 14F*

```
      2910       2920       2930       2940       2950       2960       2970       2980       2990       3000
         *          *          *          *          *          *          *          *          *          *
2901 GCGATGCCATCGTCCGGGGGCCAGCGGGGCACCCGTCGGTCGCACACAAATCGCTCGCCGGAGCGCAGCCGGCGTATGACCGACGGCTGCGTCGAGGTGCTGGC 3000
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     hygR 3010       3020       3030       3040       3050       3060       3070       3080       3090       3100
         *          *          *          *          *          *          *          *          *          *
3001 CGACAGGCGCAACCGCCGGCCCAGTACACGACCGGCGCTAAGGAGGTAGGTCGAGTTTAAACTCTAGAACCGGTCATGGCCGCAATAAAATATCTTTAT 3100
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>
     hygR 3110       3120       3130       3140       3150       3160       3170       3180       3190       3200
         *          *          *          *          *          *          *          *          *          *
3101 TTTCATTACATCTGTGTGTTGGTTTTTTGTGTGTTCGAACTAGATGTGTCGACCGATGCCCTTGAGAGCCTTCAACCCAGTCAGCTCCTTCCGGTGGGC 3200

3210       3220       3230       3240       3250       3260       3270       3280       3290       3300
         *          *          *          *          *          *          *          *          *          *
3201 GCGGGGGCATGACTGATCGTCGCCGCCACTTATGACTCGCTGTCTTCTTTATCATGCAACTCGTAGGACAGGTGCCGCTCTTCCTCGCTCACTGA 3300
                                                                                      >>>>>>>>>>>>>>>>>>
                                                                                      ColE1 origin from pBR322

3310       3320       3330       3340       3350       3360       3370       3380       3390       3400
         *          *          *          *          *          *          *          *          *          *
3301 CTCGCTGCGCTCGGTCGTTCGGCTGCGGCGAGCGGTATCAGCTCACTCAAAGGCGGTAATACGGTTATCCACAGAATCAGGGGATAACGCAGGAAAGAAC 3400
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     ColE1 origin from pBR322
```

*Fig. 14G*

```
          3410      3420      3430      3440      3450      3460      3470      3480      3490      3500
             *         *         *         *         *         *         *         *         *         *
3401  ATGTGAGCAAAAGGCCAGCAACCGTAAAAAGGCCGCGTTGCTGGCGTTTTTCCATAGGCTCCGCCCCCCTGACGAGCATCACAAAAATC  3500
      >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
      ColE1 origin from pBR322

3510      3520      3530      3540      3550      3560      3570      3580      3590      3600
             *         *         *         *         *         *         *         *         *         *
3501  GACGCTCAAGTCAGAGGTGGCGAAACCCGACAGGACTATAAAGATACCAGGCGTTTCCCCCTGGAAGCTCCCTCGTGCGCTCTCCTGTTCCGACCCTGCC  3600
      >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
      ColE1 origin from pBR322

3610      3620      3630      3640      3650      3660      3670      3680      3690      3700
             *         *         *         *         *         *         *         *         *         *
3601  GCTTACCGGATACCTGTCCGCCTTTCTCCCTTCGGGAAGCGTGGCGCTTTCTCATAGCTCACGCTGTAGGTATCTCAGTTCGGTGTAGGTCGTTCGCTCC  3700
      >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
      ColE1 origin from pBR322

3710      3720      3730      3740      3750      3760      3770      3780      3790      3800
             *         *         *         *         *         *         *         *         *         *
3701  AAGCTGGGCTGTGTGCACGAACCCCCCGTTCAGCCCGACCGCTGCGCCTTATCCGGTAACTATCGTCTTGAGTCCAACCCGGTAAGACACGACTTATCGC  3800
      >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
      ColE1 origin from pBR322

3810      3820      3830      3840      3850      3860      3870      3880      3890      3900
             *         *         *         *         *         *         *         *         *         *
3801  CACTGGCAGCAGCCACTGGTAACAGGATTAGCAGAGCGAGGTATGTAGGCGGTGCTACAGAGTTCTTGAAGTGGTGGCCTAACTACGGCTACACTAGAAG  3900
      >>>>>>
      ColE1 origin from pBR322
```

*Fig. 14H*

```
              3910       3920       3930       3940       3950       3960       3970       3980       3990       4000
                *          *          *          *          *          *          *          *          *          *
3901  AACAGTATTGGTATCTGCGCTGAAGCCAGTTACCTTCGGAAAAAGAGTTGGTAGCTCTTGATCCGGCAAACAAACCACCGCTGGTAGCGGTGGT  4000

4010       4020       4030       4040       4050       4060       4070       4080       4090       4100
                *          *          *          *          *          *          *          *          *          *
4001  TTTTTTGTTTGCAAGCAGCAGATTACGCGCAGAAAAAGGATCTCAAGAAGATCCTTTGATCTTTTCTACGGGGTCTGACGCTCAGTGGAACGAAAACT  4100

4110       4120       4130       4140       4150       4160       4170       4180       4190       4200
                *          *          *          *          *          *          *          *          *          *
4101  CACGTTAAGGGATTTTGGTCATGAGATTATCAAAAAGGATCTTCACCTAGATCCTTTTTAAATTAAAAATGAAGTTTTAAATCAATCTAAAGTATATATGA  4200

4210       4220       4230       4240       4250       4260       4270       4280       4290       4300
                *          *          *          *          *          *          *          *          *          *
4201  GTAAACTTGGTCTGACAGTTACCAATGCTTAATCAGTGAGGCACCTGTTGCTGACTCCCCGTCGTGTAGATAACTACGATACGGGAGGGCTTACCATCAGG  4300
                                                                                <<<<<<<<<<<<<<<<<<<<<<<<<<<<<<<<<<<<<
                                                                                                              ampR 4310       4320       4330       4340       4350       4360       4370       4380       4390       4400
                *          *          *          *          *          *          *          *          *          *
4301  CGTCCATAGTGGCCTGACTCCCCGTCGTGTAGATAACTACGATACGATTCGTGAGGGCTTACCATCAGGCCCCAGCGCAGCAATGATGCCGCGAGAGCCGGTTC  4400
      <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
      ampR 4410       4420       4430       4440       4450       4460       4470       4480       4490       4500
                *          *          *          *          *          *          *          *          *          *
4401  ACCGGCTCCAGATTTGTCAGCAATGAACCAGCCAGCAGGGAGGGCCGAGCGCAGAAGTGGTCCTGCTACTTTGTCCGCCTCCATCCAGTCTATGAGCTGC  4500
      <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
      ampR
```

*Fig. 14I*

```
      4510      4520      4530      4540      4550      4560      4570      4580      4590      4600
        *         *         *         *         *         *         *         *         *         *
4501 TGTCGTGATGCTAGAGTAAGAAGTTCGCCAGTAGTTCCGAAGAGTTGTGGCATTGCTACTGGCATCGTGGTATCACGCTCGTCGTTCGTTGG
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 4610      4620      4630      4640      4650      4660      4670      4680      4690      4700
        *         *         *         *         *         *         *         *         *         *
4601 CTTCGTTCAACTCTGGTTCCCAGGGTCAAGCGGGTCACATGATCACCCATATTATGAAGAAATGCAGTCAGCTCCTTAGGGCCTCCGATCGTTGTCAG
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 4710      4720      4730      4740      4750      4760      4770      4780      4790      4800
        *         *         *         *         *         *         *         *         *         *
4701 AAGTAAGTTGGCCGCGGTGTTGTCGCTCATGGTAATGCAGCACTACACAATTCTCTTACCGTCATGCCATCCGTAAGATGCTTTTCCGTGACCGGCGAG
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 4810      4820      4830      4840      4850      4860      4870      4880      4890      4900
        *         *         *         *         *         *         *         *         *         *
4801 TACTCAACCAAGTCGTTTTGTGAGTAGTGTATACGGGCGACCAAGTCTGCTCTTGCCCGGGCGTCTATACGGACAAACACCGCGCCACATAGCAGTACTTTGA
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 4910      4920      4930      4940      4950      4960      4970      4980      4990      5000
        *         *         *         *         *         *         *         *         *         *
4901 AAGTGCTCATCATCGGGAATCGTTCTTCGGGGGGGAAAGACTCAAGGATCTTGCCGCGTATTGAGAATCTTGGATATAGCCCACTCTTGCACCCAGTTG
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR
```

*Fig. 14J*

```
              5010       5020       5030       5040       5050       5060       5070       5080       5090       5100
                *          *          *          *          *          *          *          *          *          *
5001 ATCTTCAGCATCTTTTACTTTCACCAGCGTTTCGGGGTGTGCAAAAACAGGCAAGCAAGAAGGGAATGAGTGCGACACGAAAATGTTGG
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 5110       5120       5130       5140       5150       5160       5170       5180       5190       5200
                *          *          *          *          *          *          *          *          *          *
5101 ATGCTCATACTCGTCCTTTTCAATATATTGAAGCATTTATCAGGGTTACTAGTAGTCTCTCAAGGATAAGTAAGTAATATTAAGGTACGGGGAGGTAT
     <<<<<<<
     ampR 5210       5220       5230       5240       5250       5260       5270       5280       5290       5300
                *          *          *          *          *          *          *          *          *          *
5201 TGGACAGGCCCGCCAATAAAATATCTTTATTTTCATTACATCTGTGTGTTTTGTGGTTTTTTGTGTGAATCGATAGTACTAACATACGCTCTCCATCAAAACAAAA
                                        >>>>>>>>>>>>>>>>>>>>>>>>>>>>>>>>>>>>>
                                         polyA signal sequence 5310       5320       5330       5340       5350       5360
                *          *          *          *          *          *
5301 CGAAACAAAACAAACTAGCAAAATAGGCTGTCCCCAGTGCAAGTGCAGGTGCCAGAACATTTCTCT 5366
```

*Fig. 14K*

SEQUENCE LISTING

<160> NUMBER OF SEQ ID NOS: 11

<210> SEQ ID NO 1
<211> LENGTH: 413
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (8)..(55)
<223> OTHER INFORMATION: Hammerhead ribozyme region
<220> FEATURE:
<221> NAME/KEY: misc_feature
<222> LOCATION: (51)..(58)
<223> OTHER INFORMATION: D8 complement
<220> FEATURE:
<221> NAME/KEY: misc_feature
<222> LOCATION: (59)..(63)
<223> OTHER INFORMATION: P5 complement
<220> FEATURE:
<221> NAME/KEY: misc_feature
<222> LOCATION: (93)..(98)
<223> OTHER INFORMATION: Stuffer insertion site
<220> FEATURE:
<221> NAME/KEY: misc_feature
<222> LOCATION: (99)..(106)
<223> OTHER INFORMATION: 2nd D8 complement
<220> FEATURE:
<221> NAME/KEY: misc_feature
<222> LOCATION: (107)..(111)
<223> OTHER INFORMATION: 2nd P5 complement
<220> FEATURE:
<221> NAME/KEY: misc_feature
<222> LOCATION: (126)..(172)
<223> OTHER INFORMATION: Hairpin catalytic core complement
<220> FEATURE:
<221> NAME/KEY: misc_feature
<222> LOCATION: (221)..(315)
<223> OTHER INFORMATION: Multiple cloning site
<220> FEATURE:
<221> NAME/KEY: primer_bind
<222> LOCATION: (255)..(280)
<223> OTHER INFORMATION: Primer 2 complement
<220> FEATURE:
<221> NAME/KEY: primer_bind
<222> LOCATION: (281)..(301)
<223> OTHER INFORMATION: RT primer 1 complement
<220> FEATURE:
<221> NAME/KEY: misc_feature
<222> LOCATION: (326)..(413)
<223> OTHER INFORMATION: HDV negative strand ribozyme

<400> SEQUENCE: 1
ataccctgtc accggatgtg ctttccggtc tgatgagtcc gtgaggacga acaggactg      60 tcaggtggcc gaaagccacc acgtaaacta gtggatccaa caggactgtc agctagtcaa    120
ggcgtaccag gtaatatacc acaacgtgtg tttctctggt tgacttctct gtttgttgtg    180
tcattggttc ccggatctcg cattagcggc gacggggtat cctgcaggaa gcttggatcc    240
gtcgacgcgg ccgcgatcgt cggactgtag aactctgaac ccttggcacc cgagaattcc    300
agaattcggc gcgccatacc ctgtcgggtc ggcatggcat ctccacctcc tcgcggtccg    360
acctgggcat ccgaaggagg acagacgtcc actcggatgg ctaagggaga gcc           413

<210> SEQ ID NO 2

<400> SEQUENCE: 2

000

<210> SEQ ID NO 3

-continued

```
<211> LENGTH: 48
<212> TYPE: DNA
<213> ORGANISM: Satellite tobacco ringspot virus

<400> SEQUENCE: 3
gacagagaag tcaaccagag aaacacacgt tgtggtatat tacctggt         48

<210> SEQ ID NO 4
<211> LENGTH: 50
<212> TYPE: DNA
<213> ORGANISM: Satellite arabis mosaic virus

<400> SEQUENCE: 4
gacagcgaag tcaaacggcg aaacacacct tgtgtggtat attacccgtt       50

<210> SEQ ID NO 5
<211> LENGTH: 50
<212> TYPE: DNA
<213> ORGANISM: Satellite chicory yellow mottle virus

<400> SEQUENCE: 5
gacagcgaag tcagccaggg aaacacacca tgtgtggtat attatctggc       50

<210> SEQ ID NO 6
<211> LENGTH: 13
<212> TYPE: DNA
<213> ORGANISM: Artificial Sequence
<220> FEATURE:
<223> OTHER INFORMATION: Synthetic DNA

<400> SEQUENCE: 6
tgaccgtcct gtc                                               13

<210> SEQ ID NO 7
<211> LENGTH: 13
<212> TYPE: RNA
<213> ORGANISM: Artificial Sequence
<220> FEATURE:
<223> OTHER INFORMATION: Synthetic RNA
<220> FEATURE:
<221> NAME/KEY: misc_feature
<223> OTHER INFORMATION: n=A, C, G or U
<220> FEATURE:
<221> NAME/KEY: misc_feature
<222> LOCATION: (1)..(5)
<223> OTHER INFORMATION: n is a, c, g, or u
<220> FEATURE:
<221> NAME/KEY: misc_feature
<222> LOCATION: (9)..(13)
<223> OTHER INFORMATION: n is a, c, g, or u

<400> SEQUENCE: 7
nnnnngucnn nnn                                               13

<210> SEQ ID NO 8
<211> LENGTH: 50
<212> TYPE: RNA
<213> ORGANISM: Artificial Sequence
<220> FEATURE:
<223> OTHER INFORMATION: Synthetic RNA
<220> FEATURE:
<221> NAME/KEY: misc_feature
<223> OTHER INFORMATION: n=A, C, G, or U; m=A or C
<220> FEATURE:
<221> NAME/KEY: misc_feature
<222> LOCATION: (1)..(5)
<223> OTHER INFORMATION: n is a, c, g, or u
<220> FEATURE:
<221> NAME/KEY: misc_feature
```

```
<222> LOCATION: (10)..(18)
<223> OTHER INFORMATION: n is a, c, g, or u
<220> FEATURE:
<221> NAME/KEY: misc_feature
<222> LOCATION: (26)..(36)
<223> OTHER INFORMATION: n is a, c, g, or u
<220> FEATURE:
<221> NAME/KEY: misc_feature
<222> LOCATION: (46)..(50)
<223> OTHER INFORMATION: n is a, c, g, or u

<400> SEQUENCE: 8
nnnnnmgaan nnnnnnnnag aaacannnnn nnnnnnguau auuacnnnnn          50

<210> SEQ ID NO 9
<211> LENGTH: 2190
<212> TYPE: DNA
<213> ORGANISM: Artificial Sequence
<220> FEATURE:
<223> OTHER INFORMATION: Synthetic DNA
<220> FEATURE:
<221> NAME/KEY: promoter
<222> LOCATION: (6)..(23)
<223> OTHER INFORMATION: T7 RNA promoter
<220> FEATURE:
<221> NAME/KEY: misc_feature
<222> LOCATION: (38)..(85)
<223> OTHER INFORMATION: Hammerhead ribozyme region
<220> FEATURE:
<221> NAME/KEY: misc_feature
<222> LOCATION: (81)..(88)
<223> OTHER INFORMATION: D8 complement
<220> FEATURE:
<221> NAME/KEY: misc_feature
<222> LOCATION: (89)..(93)
<223> OTHER INFORMATION: P5 complement
<220> FEATURE:
<221> NAME/KEY: misc_feature
<222> LOCATION: (123)..(128)
<223> OTHER INFORMATION: Stuffer insertion site
<220> FEATURE:
<221> NAME/KEY: misc_feature
<222> LOCATION: (129)..(136)
<223> OTHER INFORMATION: 2nd D8 complement
<220> FEATURE:
<221> NAME/KEY: misc_feature
<222> LOCATION: (137)..(141)
<223> OTHER INFORMATION: 2nd P5 complement
<220> FEATURE:
<221> NAME/KEY: misc_feature
<222> LOCATION: (156)..(202)
<223> OTHER INFORMATION: Hairpin catalytic core complement
<220> FEATURE:
<221> NAME/KEY: misc_feature
<222> LOCATION: (252)..(345)
<223> OTHER INFORMATION: Multiple cloning site
<220> FEATURE:
<221> NAME/KEY: primer_bind
<222> LOCATION: (285)..(310)
<223> OTHER INFORMATION: Primer 2 complement
<220> FEATURE:
<221> NAME/KEY: primer_bind
<222> LOCATION: (311)..(330)
<223> OTHER INFORMATION: RT primer 1 complement
<220> FEATURE:
<221> NAME/KEY: misc_feature
<222> LOCATION: (357)..(442)
<223> OTHER INFORMATION: HDV negative strand ribozyme
<220> FEATURE:
<221> NAME/KEY: rep_origin
<222> LOCATION: (451)..(1065)
<223> OTHER INFORMATION: pMB1 origin of replication in the reverse
      orientation
<220> FEATURE:
<221> NAME/KEY: primer_bind
<222> LOCATION: (502)..(525)
<223> OTHER INFORMATION: Seq2 primer binding site in the reverse
```

```
            orientation
<220> FEATURE:
<221> NAME/KEY: gene
<222> LOCATION: (1225)..(2085)
<223> OTHER INFORMATION: beta-lactamase gene in the reverse orientation
<220> FEATURE:
<221> NAME/KEY: promoter
<222> LOCATION: (2086)..(2190)
<223> OTHER INFORMATION: beta-lactamase promoter in reverse orientation
<220> FEATURE:
<221> NAME/KEY: primer_bind
<222> LOCATION: (2092)..(2121)
<223> OTHER INFORMATION: Seq1 primer binding site

<400> SEQUENCE: 9
agatctaata gcactcacta tagggatct ataccctgtc accggatgtg ctttccggtc      60
tgatgagtcc gtgaggacga aacaggactg tcaggtggcc gaaagccacc acgtaaacta    120
gtggatccaa caggactgtc agctagtcaa ggcgtaccag gtaatatacc acaacgtgtg    180
tttctctggt tgacttctct gtttgttgtg tcattggttc ccggatctcg cattagcggc    240
gacggggtat cctgcaggaa gcttggatcc gtcgacgcgg ccgcgatcgt cggactgtag    300
aactctgaac ccttggcacc cgagaattcc agaattcggc gcgccatacc ctgtcgggtc    360
ggcatggcat ctccacctcc tcgcggtccg acctgggcat ccgaaggagg acagacgtcc    420
actcggatgg ctaagggaga gccatctaga cgcgttgctg gcgttttttcc ataggctccg    480 ccccctgac gagcatcaca aaaatcgacg ctcaagtcag aggtggcgaa acccgacagg    540
actataaaga taccaggcgt ttcccctgg aagctccctc gtgcgctctc ctgttccgac    600
cctgccgctt accggatacc tgtccgcctt tctcccttcg ggaagcgtgg cgctttctca    660
tagctcacgc tgtaggtatc tcagttcggt gtaggtcgtt cgctccaagc tgggctgtgt    720
gcacgaaccc cccgttcagc ccgaccgctg cgccttatcc ggtaactatc gtcttgagtc    780
caacccggta agacacgact tatcgccact ggcagcagcc actggtaaca ggattagcag    840
agcgaggtat gtaggcggtg ctacagagtt cttgaagtgg tggcctaact acggctacac    900
tagaagaaca gtatttggta tctgcgctct gctgaagcca gttaccttcg gaaaaagagt    960
tggtagctct tgatccggca acaaaccac cgctggtagc ggtggttttt tgtttgcaa    1020 gcagcagatt acgcgcagaa aaaaaggatc tcaagaagat cctttgatct tttctacggg   1080
gtctgacgct cagtggaacg aaaactcacg ttaagggatt ttggtcatga gattatcaaa   1140
aaggatcttc acctagatcc ttttaaatta aaaatgaagt tttaaatcaa tctaaagtat   1200
atatgagtaa acttggtctg acagttacca atgcttaatc agtgaggcac ctatctcagc   1260
gatctgtcta tttcgttcat ccatagttgc ctgactcccc gtcgtgtaga taactacgat   1320
acgggagggc ttaccatctg gccccagtgc tgcaatgata ccgcgagacc cacgctcacc   1380
ggctccagat ttatcagcaa taaaccagcc agccggaagg gccgagcgca gaagtggtcc   1440
tgcaacttta tccgcctcca tccagtctat taattgttgc cgggaagcta gagtaagtag   1500
ttcgccagtt aatagtttgc gcaacgttgt tgccattgct acaggcatcg tggtgtcacg   1560
ctcgtcgttt ggtatggctt cattcagctc cggttcccaa cgatcaaggc gagttacatg   1620 atccccccatg ttgtgcaaaa aagcggttag ctccttcggt cctccgatcg ttgtcagaag   1680
taagttggcc gcagtgttat cactcatggt tatggcagca ctgcataatt ctcttactgt   1740
catgccatcc gtaagatgct tttctgtgac tggtgagtac tcaaccaagt cattctgaga   1800
atagtgtatg cggcgaccga gttgctcttg cccggcgtca atacgggata ataccgcgcc   1860
acatagcaga actttaaaag tgctcatcat tggaaaacgt tcttcggggc gaaaactctc   1920
```

```
aaggatctta ccgctgttga gatccagttc gatgtaaccc actcgtgcac ccaactgatc    1980
ttcagcatct tttactttca ccagcgtttc tgggtgagca aaaacaggaa ggcaaaatgc    2040
cgcaaaaaag ggaataaggg cgacacggaa atgttgaata ctcatactct tcctttttca    2100
atattattga agcatttatc agggttattg tctcatgagc ggatacatat ttgaatgtat    2160
ttagaaaaat aaacaaatag gggttccgcg                                     2190
```

<210> SEQ ID NO 10
<211> LENGTH: 8313
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)..(161)
<223> OTHER INFORMATION: T-DNA right border
<220> FEATURE:
<221> NAME/KEY: promoter
<222> LOCATION: (470)..(782)
<223> OTHER INFORMATION: CaMV 35S promoter
<220> FEATURE:
<221> NAME/KEY: misc_feature
<222> LOCATION: (793)..(840)
<223> OTHER INFORMATION: Hammerhead ribozyme region
<220> FEATURE:
<221> NAME/KEY: misc_feature
<222> LOCATION: (836)..(843)
<223> OTHER INFORMATION: D8 complement
<220> FEATURE:
<221> NAME/KEY: misc_feature
<222> LOCATION: (844)..(848)
<223> OTHER INFORMATION: P5 complement
<220> FEATURE:
<221> NAME/KEY: misc_feature
<222> LOCATION: (878)..(883)
<223> OTHER INFORMATION: Stuffer insertion site
<220> FEATURE:
<221> NAME/KEY: misc_feature
<222> LOCATION: (884)..(891)
<223> OTHER INFORMATION: 2nd D8 complement
<220> FEATURE:
<221> NAME/KEY: misc_feature
<222> LOCATION: (892)..(896)
<223> OTHER INFORMATION: 2nd P5 complement
<220> FEATURE:
<221> NAME/KEY: misc_feature
<222> LOCATION: (911)..(957)
<223> OTHER INFORMATION: Hairpin catalytic core complement
<220> FEATURE:
<221> NAME/KEY: misc_feature
<222> LOCATION: (1007)..(1100)
<223> OTHER INFORMATION: Multiple cloning site
<220> FEATURE:
<221> NAME/KEY: primer_bind
<222> LOCATION: (1040)..(1065)
<220> FEATURE:
<221> NAME/KEY: primer_bind
<222> LOCATION: (1066)..(1085)
<220> FEATURE:
<221> NAME/KEY: misc_feature
<222> LOCATION: (1066)..(1085)
<223> OTHER INFORMATION: HDV negative strand ribozyme
<220> FEATURE:
<221> NAME/KEY: terminator
<222> LOCATION: (1200)..(1897)
<223> OTHER INFORMATION: CaMV 35S terminator
<220> FEATURE:
<221> NAME/KEY: gene
<222> LOCATION: (2235)..(3029)
<223> OTHER INFORMATION: neomycin phosphotransferase II gene
<220> FEATURE:
<221> NAME/KEY: rep_origin
<222> LOCATION: (2235)..(3029)

```
<223> OTHER INFORMATION: ColE1 origin of replication from pBR322
<220> FEATURE:
<221> NAME/KEY: misc_feature
<222> LOCATION: (3711)..(3857)
<223> OTHER INFORMATION: T-DNA left border in the reverse orientation
<220> FEATURE:
<221> NAME/KEY: rep_origin
<222> LOCATION: (4164)..(4779)
<223> OTHER INFORMATION: OriV from pRK2 in the reverse orientation
<220> FEATURE:
<221> NAME/KEY: gene
<222> LOCATION: (4878)..(6026)
<223> OTHER INFORMATION: trfA gene in the reverse orientation
<220> FEATURE:
<221> NAME/KEY: gene
<222> LOCATION: (6325)..(7119)
<223> OTHER INFORMATION: neomycin phosphotransferase III gene in the
      reverse orientation

<400> SEQUENCE: 10
cctgtggttg gcatgcacat acaaatggac gaacggataa accttttcac gccctttta       60 atatccgatt attctaataa acgctctttt ctcttaggtt tacccgccaa tatatcctgt      120
caaacactga tagtttgtga accatcaccc aaatcaagtt ttttggggtc gaggtgccgt      180
aaagcactaa atcggaaccc taagggagc ccccgattta gagcttgacg gggaaagccg       240
gcgaacgtgg cgagaaagga agggaagaaa gcgaaaggag cgggcgccat tcaggctgcg      300
caactgttgg aagggcgat cggtgcgggc ctcttcgcta ttacgccagc tggcgaaagg       360
gggatgtgct gcaaggcgat taagttgggt aacgccaggg ttttcccagt cacgacgttg      420
taaaacgacg gccagtgaat tgttaattaa gaattcgagc tccaccgcgg aaacctcctc      480
ggattccatt gcccagctat ctgtcacttt attgagaaga tagtggaaaa ggaaggtggc      540
tcctacaaat gccatcattg cgataaagga aaggccatcg ttgaagatgc ctctgccgac      600
agtggtccca agatggacc cccacccacg aggagcatcg tggaaaaaga agacgttcca       660
accacgtctt caaagcaagt ggattgatgt gatatctcca ctgacgtaag ggatgacgca      720
caatcccact atccttcgca agacccttcc tctatataag gaagttcatt tcatttggag      780
agggtatacc ctgtcaccgg atgtgctttc cggtctgatg agtccgtgag gacgaaacag      840
gactgtcagg tggccgaaag ccaccacgta aactagtgga tccaacagga ctgtcagcta      900
gtcaaggcgt accaggtaat ataccacaac gtgtgtttct ctggttgact tctctgtttg      960
ttgtgtcatt ggttcccgga tctcgcatta gcggcgacgg ggtatcctgc aggaagcttg     1020
gatccgtcga cgcggccgcg atcgtcggac tgtagaactc tgaaccctg gcacccgaga     1080 attccagaat tcggcgcgcc ataccctgtc gggtcggcat ggcatctcca cctcctcgcg     1140
gtccgacctg gcatccgaa ggaggacaga cgtccactcg gatggctaag ggagagccat     1200
cgaattcgct gaaatcacca gtctctctct acaaatctat ctctctctat tttctccata     1260
aataatgtgt gagtagtttc ccgataaggg aaattagggt tcttataggg tttcgctcat     1320
gtgttgagca tataagaaac ccttagtatg tatttgtatt tgtaaaatac ttctatcaat     1380
aaaatttcta attcctaaaa ccaaaatcca gtactaaaat ccagatctcc taaagtccct     1440
atagatcttt gtcgtgaata taaaccagac acgagacgac taaacctgga gcccagacgc     1500
cgttcgaagc tagaagtacc gcttaggcag gaggccgtta gggaaaagat gctaaggcag     1560
ggttggttac gttgactccc ccgtaggttt ggtttaaata tgatgaagtg gacggaagga     1620
aggaggaaga caaggaagga taaggttgca ggccctgtgc aaggtaagaa gatggaaatt     1680
tgatagaggt acgctactat acttatacta tacgctaagg gaatgcttgt atttatccc      1740
```

```
tataccccct aataacccct tatcaatttta agaaataatc cgcataagcc cccgcttaaa    1800
aattggtatc agagccatga ataggtctat gaccaaaact caagaggata aaacctcacc    1860
aaaatacgaa agagttctta actctaaaga taaaagatgg cgcgtggccg gcctacagta    1920
tgagcggaga attaagggag tcacgttatg accccgccg atgacgcggg acaagccgtt     1980
ttacgtttgg aactgacaga accgcaacgt tgaaggagcc actcagccgc gggtttctgg    2040
agtttaatga gctaagcaca tacgtcagaa accattattg cgcgttcaaa agtcgcctaa    2100
ggtcactatc agctagcaaa tatttcttgt caaaaatgct ccactgacgt tccataaatt    2160
cccctcggta tccaattaga gtctcatatt cactctcaat ccaaataatc tgcaccggat    2220
ctggatcgtt tcgcatgatt gaacaagatg gattgcacgc aggttctccg gccgcttggg    2280
tggagaggct attcggctat gactgggcac aacagacaat cggctgctct gatgccgccg    2340
tgttccggct gtcagcgcag gggcgcccgg ttcttttttgt caagaccgac ctgtccggtg    2400
ccctgaatga actgcaggac gaggcagcgc ggctatcgtg gctggccacg acgggcgttc    2460
cttgcgcagc tgtgctcgac gttgtcactg aagcgggaag ggactggctg ctattgggcg    2520
aagtgccggg gcaggatctc ctgtcatctc accttgctcc tgccgagaaa gtatccatca    2580
tggctgatgc aatgcggcgg ctgcatacgc ttgatccggc tacctgccca ttcgaccacc    2640
aagcgaaaca tcgcatcgag cgagcacgta ctcggatgga agccggtctt gtcgatcagg    2700
atgatctgga cgaagagcat caggggctcg cgccagccga actgttcgcc aggctcaagg    2760
cgcgcatgcc cgacggcgat gatctcgtcg tgacccatgg cgatgcctgc ttgccgaata    2820
tcatggtgga aaatggccgc ttttctggat tcatcgactg tggccggctg ggtgtggcgg    2880
accgctatca ggacatagcg ttggctaccc gtgatattgc tgaagagctt ggcggcgaat    2940
gggctgaccg cttcctcgtg ctttacggta tcgccgctcc cgattcgcag cgcatcgcct    3000
tctatcgcct tcttgacgag ttcttctgag cgggactctg gggttcgaaa tgaccgacca    3060
agcgacgccc aacctgccat cacgagattt cgattccacc gccgccttct atgaaaggtt    3120
gggcttcgga atcgttttcc gggacgccgg ctggatgatc ctccagcgcg ggatctcat    3180 gctggagttc ttcgcccacg gatctctgc ggaacaggcg gtcgaaggtg ccgatatcat    3240
tacgacagca acggccgaca agcacaacgc cacgatcctg agcgacaata tgatcgcggc    3300
gtccacatca acggcgtcgg cggcgactgc ccaggcaaga ccgagatgca ccgcgatatc    3360
ttgctgcgtt cggatatttt cgtggagttc ccgccacaga cccggatgat ccccgatcgt    3420
tcaaacattt ggcaataaag tttcttaaga ttgaatcctg ttgccggtct tgcgatgatt    3480
atcatataat ttctgttgaa ttacgttaag catgtaataa ttaacatgta atgcatgacg    3540
ttatttatga gatgggtttt tatgattaga gtcccgcaat tatacattta atacgcgata    3600
gaaaacaaaa tatagcgcgc aaactaggat aaattatcgc gcgcggtgtc atctatgtta    3660
ctagatcggg actgtaggcc ggccctcact ggtgaaaaga aaaccaccc cagtacatta    3720 aaaacgtccg caatgtgtta ttaagttgtc taagcgtcaa tttgtttaca ccacaatata    3780
tcctgccacc agccagccaa cagctccccg accggcagct cggcacaaaa tcaccactcg    3840
atacaggcag cccatcagtc cgggacggcg tcagcgggag agccgttgta aggcggcaga    3900
ctttgctcat gttaccgatg ctattcggaa gaacggcaac taagctgccg ggtttgaaac    3960
acggatgatc tcgcggaggg tagcatgttg attgtaacga tgacagagcg ttgctgcctg    4020
tgatcaaata tcatctcccct cgcagagatc cgaattatca gccttcttat tcatttctcg    4080
cttaaccgtg acagagtaga caggctgtct cgcggccgag gggcgcagcc cctgggggggg    4140
```

```
atgggaggcc cgcgttagcg ggccgggagg gttcgagaag ggggggcacc ccccttcggc    4200
gtgcgcggtc acgcgcacag ggcgcagccc tggttaaaaa caaggtttat aaatattggt    4260
ttaaaagcag gttaaaagac aggttagcgg tggccgaaaa acgggcggaa acccttgcaa    4320
atgctggatt ttctgcctgt ggacagcccc tcaaatgtca ataggtgcgc ccctcatctg    4380
tcagcactct gcccctcaag tgtcaaggat cgcgcccctc atctgtcagt agtcgcgccc    4440
ctcaagtgtc aataccgcag ggcacttatc cccaggcttg tccacatcat ctgtgggaaa    4500
ctcgcgtaaa atcaggcgtt ttcgccgatt tgcgaggctg gccagctcca cgtcgccggc    4560
cgaaatcgag cctgcccctc atctgtcaac gccgcgccgg gtgagtcggc ccctcaagtg    4620
tcaacgtccg cccctcatct gtcagtgagg gccaagtttt ccgcgaggta tccacaacgc    4680
cggcggccgc ggtgtctcgc acacggcttc gacggcgttt ctggcgcgtt tgcagggcca    4740
tagacggccg ccagcccagc ggcgagggca accagcccgg tgagcgtcgg aaaggcgctc    4800
ggtcttgcct tgctcgtcgg tgatgtacac tagtcgctgg ctgctgaacc cccagccgga    4860
actgacccca caaggcccta gcgtttgcaa tgcaccaggt catcattgac ccaggcgtgt    4920
tccaccaggc cgctgcctcg caactcttcg caggcttcgc cgacctgctc gcgccacttc    4980
ttcacgcggg tggaatccga tccgcacatg aggcggaagg tttccagctt gagcgggtac    5040
ggctcccggt gcgagctgaa atagtcgaac atcgtcgggg ccgtcggcga cagcttgcgg    5100
tacttctccc atatgaattt cgtgtagtgg tcgccagcaa acagcacgac gatttcctcg    5160
tcgatcagga cctggcaacg ggacgttttc ttgccacggt ccaggacgcg gaagcggtgc    5220
agcagcgaca ccgattccag gtgcccaacg cggtcggacg tgaagcccat cgccgtcgcc    5280
tgtaggcgcg acaggcattc ctcggccttc gtgtaatacc ggccattgat cgaccagccc    5340
aggtcctggc aaagctcgta gaacgtgaag gtgatcggct cgccgatagg ggtgcgcttc    5400
gcgtactcca cacctgctg ccacaccagt tcgtcatcgt cggcccgcag ctcgacgccg    5460
gtgtaggtga tcttcacgtc cttgttgacg tggaaaatga ccttgttttg cagcgcctcg    5520
cgcgggattt tcttgttgcg cgtggtgaac agggcagagc gggccgtgtc gtttggcatc    5580
gctcgcatcg tgtccggcca cggcgcaata tcgaacaagg aaagctgcat ttccttgatc    5640
tgctgcttcg tgtgtttcag caacgcggcc tgcttggcct cgctgacctg ttttgccagg    5700
tcctcgccgg cggttttttcg cttcttggtc gtcatagttc ctcgcgtgtc gatggtcatc    5760
gacttcgcca aacctgccgc ctcctgttcg agacgacgcg aacgctccac ggcggccgat    5820
ggcgcgggca gggcagggg agccagttgc acgctgtcgc gctcgatctt ggccgtagct    5880
tgctggacca tcgagccgac ggactggaag gtttcgcggg gcgcacgcat gacggtgcgg    5940
cttgcgatgg tttcggcatc ctcggcggaa aaccccgcgt cgatcagttc ttgcctgtat    6000
gccttccggt caaacgtccg attcattcac cctccttgcg ggattgcccc gactcacgcc    6060
ggggcaatgt gcccttattc ctgatttgac ccgcctggtg ccttggtgtc cagataatcc    6120
accttatcgg caatgaagtc ggtcccgtag accgtctggc cgtccttctc gtacttggta    6180
ttccgaatct tgccctgcac gaataccagc gacccctttgc ccaaatactt gccgtgggcc    6240
tcggcctgag agccaaaaca cttgatgcgg aagaagtcgg tgcgctcctg cttgtcgccg    6300
gcatcgttgc gccacatcta ggtactaaaa caattcatcc agtaaaatat aatattttat    6360
tttctcccaa tcaggcttga tccccagtaa gtcaaaaaat agctgacat actgttcttc    6420 cccgatatcc tccctgatcg accggacgca gaaggcaatg tcataccact tgtccgccct    6480
```

-continued

```
gccgcttctc caagatcaa taaagccact tactttgcca tctttcacaa agatgttgct      6540
gtctcccagg tcgccgtggg aaaagacaag ttcctcttcg ggcttttccg tctttaaaaa      6600
atcatacagc tcgcgcggat ctttaaatgg agtgtcttct tcccagtttt cgcaatccac      6660
atcggccaga tcgttattca gtaagtaatc caattcggct aagcggctgt ctaagctatt      6720
cgtataggga caatccgata tgtcgatgga gtgaaagagc ctgatgcact ccgcatacag      6780
ctcgataatc ttttcagggc tttgttcatc ttcatactct tccgagcaaa ggacgccatc      6840
ggcctcactc atgagcagat tgctccagcc atcatgccgt tcaaagtgca ggacctttgg      6900
aacaggcagc tttccttcca gccatagcat catgtccttt tcccgttcca catcataggt      6960 ggtccccttta taccggctgt ccgtcatttt taaatatagg ttttcattttt ctcccaccag      7020 cttatatacc ttagcaggag acattccttc cgtatctttt acgcagcggt attttttcgat      7080 cagttttttc aattccggtg atattctcat tttagccatt tattatttcc ttcctcttttt      7140 ctacagtatt taaagatacc ccaagaagct aattataaca agacgaactc caattcactg      7200
ttccttgcat tctaaaacct taaataccag aaaacagctt tttcaaagtt gttttcaaag      7260
ttggcgtata acatagtatc gacggagccg attttgaaac cacaattatg ggtgatgctg      7320
ccaacttact gatttagtgt atgatggtgt ttttgaggtg ctccagtggc ttctgtttct      7380
atcagctgtc cctcctgttc agctactgac ggggtggtgc gtaacggcaa aagcaccgcc      7440
ggacatcagc gctatctctg ctctcactgc cgtaaaacat ggcaactgca gttcacttac      7500
accgcttctc aacccggtac gcaccagaaa atcattgata tggccatgaa tggcgttgga      7560
tgccgggcaa cagcccgcat tatgggcgtt ggcctcaaca cgattttacg tcacttaaaa      7620
aactcaggcc gcagtcggta actatgcggt gtgaaatacc gcacagatgc gtaaggagaa      7680
aataccgcat caggcgctct tccgcttcct cgctcactga ctcgctgcgc tcggtcgttc      7740
ggctgcggcg agcggtatca gctcactcaa aggcggtaat acggttatcc acagaatcag      7800
gggataacgc aggaaagaac atgtgagcaa aaggccagca aaaggccagg aaccgtaaaa      7860
aggccgcgtt gctggcgttt ttccataggc tccgcccccc tgacgagcat cacaaaaatc      7920
gacgctcaag tcagaggtgg cgaaacccga caggactata aagataccag gcgtttcccc      7980
ctggaagctc cctcgtgcgc tctcctgttc cgaccctgcc gcttaccgga tacctgtccg      8040
cctttctccc ttcgggaagc gtggcgcttt ctcatagctc acgctgtagg tatctcagtt      8100
cggtgtaggt cgttcgctcc aagctgggct gtgtgcacga accccccgtt cagcccgacc      8160
gctgcgcctt atccggtaac tatcgtcttg agtccaaccc ggtaagacac gacttatcgc      8220
cactggcagc aggtaacctc gcgcatacag ccgggcagtg acgtcatcgt ctgcgcggaa      8280
atggacgggc ccccggcgcc agatctgggg aac                                  8313
```

<210> SEQ ID NO 11
<211> LENGTH: 5366
<212> TYPE: DNA
<213> ORGANISM: Artificial Sequence
<220> FEATURE:
<223> OTHER INFORMATION: Synthetic DNA
<220> FEATURE:
<221> NAME/KEY: promoter
<222> LOCATION: (15)..(754)
<223> OTHER INFORMATION: CMV promoter
<220> FEATURE:
<221> NAME/KEY: misc_feature
<222> LOCATION: (866)..(913)
<223> OTHER INFORMATION: Hammerhead ribozyme region
<220> FEATURE:
<221> NAME/KEY: misc_feature

```
<222> LOCATION: (909)..(916)
<223> OTHER INFORMATION: D8 complement
<220> FEATURE:
<221> NAME/KEY: misc_feature
<222> LOCATION: (917)..(921)
<223> OTHER INFORMATION: P5 complement
<220> FEATURE:
<221> NAME/KEY: misc_feature
<222> LOCATION: (951)..(956)
<223> OTHER INFORMATION: Stuffer insertion site
<220> FEATURE:
<221> NAME/KEY: misc_feature
<222> LOCATION: (957)..(964)
<223> OTHER INFORMATION: 2nd D8 complement
<220> FEATURE:
<221> NAME/KEY: misc_feature
<222> LOCATION: (965)..(969)
<223> OTHER INFORMATION: 2nd P5 complement
<220> FEATURE:
<221> NAME/KEY: misc_feature
<222> LOCATION: (984)..(1030)
<223> OTHER INFORMATION: Hairpin catalytic core complement
<220> FEATURE:
<221> NAME/KEY: misc_feature
<222> LOCATION: (1080)..(1173)
<223> OTHER INFORMATION: Multiple cloning site
<220> FEATURE:
<221> NAME/KEY: primer_bind
<222> LOCATION: (1113)..(1138)
<223> OTHER INFORMATION: Primer 2 complement
<220> FEATURE:
<221> NAME/KEY: primer_bind
<222> LOCATION: (1139)..(1158)
<223> OTHER INFORMATION: RT primer 1 complement
<220> FEATURE:
<221> NAME/KEY: misc_feature
<222> LOCATION: (1185)..(1270)
<223> OTHER INFORMATION: HDV negative strand ribozyme
<220> FEATURE:
<221> NAME/KEY: polyA_signal
<222> LOCATION: (1313)..(1532)
<223> OTHER INFORMATION: polyA signal sequence
<220> FEATURE:
<221> NAME/KEY: promoter
<222> LOCATION: (1582)..(1998)
<223> OTHER INFORMATION: SV40 early enhancer/promoter
<220> FEATURE:
<221> NAME/KEY: gene
<222> LOCATION: (2024)..(3061)
<223> OTHER INFORMATION: hygromycin resistance gene
<220> FEATURE:
<221> NAME/KEY: rep_origin
<222> LOCATION: (3274)..(3812)
<223> OTHER INFORMATION: ColE1 origin of replication from pBR322
<220> FEATURE:
<221> NAME/KEY: gene
<222> LOCATION: (4248)..(5108)
<223> OTHER INFORMATION: beta-lactamase gene in the reverse orientation
<220> FEATURE:
<221> NAME/KEY: polyA_signal
<222> LOCATION: (5213)..(5260)
<223> OTHER INFORMATION: polyA signal sequence

<400> SEQUENCE: 11
ggcctaactg gcctcaatat tggccattag ccatattatt cattggttat atagcataaa      60
tcaatattgg ctattggcca ttgcatacgt tgtatctata tcataatatg tacatttata     120
ttggctcatg tccaatatga ccgccatgtt ggcattgatt attgactagt tattaatagt     180
aatcaattac ggggtcatta gttcatagcc catatatgga gttccgcgtt acataactta     240
cggtaaatgg cccgcctggc tgaccgccca acgacccccg cccattgacg tcaataatga     300
cgtatgttcc catagtaacg ccaatagggA ctttccattg acgtcaatgg gtggagtatt     360
tacggtaaac tgcccacttg gcagtacatc aagtgtatca tatgccaagt ccgcccccta     420
```

```
ttgacgtcaa tgacggtaaa tggcccgcct ggcattatgc ccagtacatg accttacggg    480
actttcctac ttggcagtac atctacgtat tagtcatcgc tattaccatg gtgatgcggt    540
tttggcagta caccaatggg cgtggatagc ggtttgactc acggggattt ccaagtctcc    600
accccattga cgtcaatggg agtttgtttt ggcaccaaaa tcaacgggac tttccaaaat    660
gtcgtaataa ccccgccccg ttgacgcaaa tgggcggtag gcgtgtacgg tgggaggtct    720
atataagcag agctcgttta gtgaaccgtc agatcactag aagctttatt gcggtagttt    780
atcacagtta aattgctaac gcagtcagtg ggcctcggcg gccaagcttg gcaatccggt    840
actgttggta aagccaccat accctgtcac cggatgtgct ttccggtctg atgagtccgt    900
gaggacgaaa caggactgtc aggtggccga aagccaccac gtaaactagt ggatccaaca    960
ggactgtcag ctagtcaagg cgtaccaggt aatataccac aacgtgtgtt tctctggttg    1020
acttctctgt ttgttgtgtc attggttccc ggatctcgca ttagcggcga cggggtatcc    1080
tgcaggaagc ttggatccgt cgacgcggcc gcgatcgtcg gactgtagaa ctctgaaccc    1140
ttggcacccg agaattccag aattcggcgc gccatacct gtcgggtcgg catggcatct    1200
ccacctcctc gcggtccgac ctgggcatcc gaaggaggac agacgtccac tcggatggct    1260
aagggagagc caggccgcga ctctagagtc ggggcggccg gccgcttcga gcagacatga    1320
taagatacat tgatgagttt ggacaaacca aactagaat gcagtgaaaa aaatgcttta    1380
tttgtgaaat ttgtgatgct attgctttat ttgtaaccat tataagctgc aataaacaag    1440
ttaacaacaa caattgcatt cattttatgt ttcaggttca gggggaggtg tgggaggttt    1500
tttaaagcaa gtaaacctc tacaaatgtg gtaaatcga taaggatccg tttgcgtatt    1560
gggcgctctt ccgctgatct gcgcagcacc atggcctgaa ataacctctg aaagaggaac    1620
ttggttagct accttctgag gcggaaagaa ccagctgtgg aatgtgtgtc agttagggtg    1680
tggaaagtcc ccaggctccc cagcaggcag aagtatgcaa agcatgcatc tcaattagtc    1740
agcaaccagg tgtggaaagt ccccaggctc cccagcaggc agaagtatgc aaagcatgca    1800
tctcaattag tcagcaacca tagtcccgcc cctaactccg cccatcccgc cctaactcc    1860 gcccagttcc gcccattctc cgccccatgg ctgactaatt ttttttattt atgcagaggc    1920
cgaggccgcc tctgcctctg agctattcca gaagtagtga ggaggctttt ttggaggcct    1980
aggcttttgc aaaaagctcg attcttctga cactagcgcc accatgaaga gcccgaact    2040 caccgctacc agcgttgaaa aatttctcat cgagaagttc gacagtgtga gcgacctgat    2100
gcagttgtcg gagggcgaag agagccgagc cttcagcttc gatgtcggcg gacgcggcta    2160
tgtactgcgg gtgaatagct gcgctgatgg cttctacaaa gaccgctacg tgtaccgcca    2220
cttcgccagc gctgcactac ccatccccga agtgttggac atcggcgagt tcagcgagag    2280
cctgacatac tgcatcagta gacgcgccca aggcgttact ctccaagacc tccccgaaac    2340
agagctgcct gctgtgttac agcctgtcgc gaagctatg gatgctattg ccgccgccga    2400
cctcagtcaa accagcggct tcgggcccatt cgggccccaa ggcatcggcc agtacacaac    2460
ctggcgggat ttcatttgcg ccattgctga tccccatgtc taccactggc agaccgtgat    2520
ggacgacacc gtgtccgcca gcgtagctca agccctggac gaactgatgc tgtgggccga    2580
agactgtccc gaggtgcgcc acctcgtcca tgccgacttc ggcagcaaca acgtcctgac    2640
cgacaacggc cgcatcaccg ccgtaatcga ctggtccgaa gctatgttcg gggacagtca    2700
gtacgaggtg gccaacatct tcttctggcg gccctggctg gcttgcatgg agcagcagac    2760
tcgctacttc gagcgccggc atcccgagct ggccggcagc cctcgtctgc gagcctacat    2820
```

```
gctgcgcatc ggcctggatc agctctacca gagcctcgtg gacggcaact tcgacgatgc    2880
tgcctgggct caaggccgct gcgatgccat cgtccgcagc ggggccggca ccgtcggtcg    2940
cacacaaatc gctcgccgga gcgcagccgt atggaccgac ggctgcgtcg aggtgctggc    3000
cgacagcggc aaccgccggc ccagtacacg accgcgcgct aaggaggtag gtcgagttta    3060
aactctagaa ccggtcatgg ccgcaataaa atatctttat tttcattaca tctgtgtgtt    3120
ggttttttgt gtgttcgaac tagatgctgt cgaccgatgc ccttgagagc cttcaaccca    3180
gtcagctcct tccggtgggc gcggggcatg actatcgtcg ccgcacttat gactgtcttc    3240
tttatcatgc aactcgtagg acaggtgccg gcagcgctct tccgcttcct cgctcactga    3300
ctcgctgcgc tcggtcgttc ggctgcggcg agcggtatca gctcactcaa aggcggtaat    3360
acggttatcc acagaatcag gggataacgc aggaaagaac atgtgagcaa aaggccagca    3420
aaaggccagg aaccgtaaaa aggccgcgtt gctggcgttt ttccataggc tccgcccccc    3480
tgacgagcat cacaaaaatc gacgctcaag tcagaggtgg cgaaacccga caggactata    3540
aagataccag gcgtttcccc ctggaagctc cctcgtgcgc tctcctgttc cgaccctgcc    3600
gcttaccgga tacctgtccg cctttctccc ttcgggaagc gtggcgcttt ctcatagctc    3660
acgctgtagg tatctcagtt cggtgtaggt cgttcgctcc aagctgggct gtgtgcacga    3720
accccccgtt cagcccgacc gctgcgcctt atccggtaac tatcgtcttg agtccaaccc    3780
ggtaagacac gacttatcgc cactggcagc agccactggt aacaggatta gcagagcgag    3840
gtatgtaggc ggtgctacag agttcttgaa gtggtggcct aactacggct acactagaag    3900
aacagtattt ggtatctgcg ctctgctgaa gccagttacc ttcggaaaaa gagttggtag    3960
ctcttgatcc ggcaaacaaa ccaccgctgg tagcggtggt ttttttgttt gcaagcagca    4020
gattacgcgc agaaaaaaag gatctcaaga agatcctttg atcttttcta cggggtctga    4080
cgctcagtgg aacgaaaact cacgttaagg gattttggtc atgagattat caaaaaggat    4140
cttcacctag atccttttaa attaaaaatg aagttttaaa tcaatctaaa gtatatatga    4200
gtaaacttgg tctgacagcg gccgcaaatg ctaaaccact gcagtggtta ccagtgcttg    4260
atcagtgagg caccgatctc agcgatctgc ctatttcgtt cgtccatagt ggcctgactc    4320
cccgtcgtgt agatcactac gattcgtgag ggcttaccat caggcccag cgcagcaatg     4380 atgccgcgag agccgcgttc accggccccc gatttgtcag caatgaacca gccagcaggg    4440
agggccgagc gaagaagtgg tcctgctact ttgtccgcct ccatccagtc tatgagctgc    4500
tgtcgtgatg ctagagtaag aagttcgcca gtgagtagtt tccgaagagt tgtggccatt    4560
gctactggca tcgtggtatc acgctcgtcg ttcggtatgg cttcgttcaa ctctggttcc    4620
cagcggtcaa gccgggtcac atgatcaccc atattatgaa gaaatgcagt cagctcctta    4680
gggcctccga tcgttgtcag aagtaagttg gccgcggtgt tgtcgctcat ggtaatggca    4740
gcactacaca attctcttac cgtcatgcca tccgtaagat gcttttccgt gaccggcgag    4800
tactcaacca gtcgtttttg tgagtagtgt atacggcgac caagctgctc ttgcccggcg    4860
tctatacggg acaacaccgc gccacatagc agtactttga aagtgctcat catcgggaat    4920
cgttcttcgg ggcggaaaga ctcaaggatc ttgccgctat tgagatccag ttcgatatag    4980
cccactcttg cacccagttg atcttcagca tctttactt tcaccagcgt ttcggggtgt     5040
gcaaaaacag gcaagcaaaa tgccgcaaag aagggaatga gtgcgacacg aaaatgttgg    5100
atgctcatac tcgtcctttt tcaatattat tgaagcattt atcagggtta ctagtacgtc    5160
```

```
tctcaaggat aagtaagtaa tattaaggta cgggaggtat tggacaggcc gcaataaaat    5220
atctttattt tcattacatc tgtgtgttgg tttttttgtgt gaatcgatag tactaacata    5280
cgctctccat caaaacaaaa cgaaacaaaa caaactagca aaataggctg tccccagtgc    5340
aagtgcaggt gccagaacat ttctct                                         5366
```

METHODS FOR RNA PROMOTER IDENTIFICATION

CROSS-REFERENCE TO RELATED APPLICATIONS

This application is the U.S. National Phase under 35 U.S.C. § 371 of Intl. Appl. No. PCT/US2016/038802, filed on Jun. 22, 2016, which claims the benefit under 35 U.S.C. § 119(e) of U.S. Provisional Application No. 62/185,060, filed on Jun. 26, 2015, which are hereby incorporated herein by reference in their entireties for all purposes.

FIELD

Provided are constructs and methods for RNA promoter identification.

BACKGROUND

Currently available technologies for identifying RNA promoters consist of individual research into viral genomic and subgenomic promoters with unknown promoters being identified by bioinformatics analysis of sequenced viral genomes to find similar regions. Generally, the sequence flanking the 5'end of an expressed subgenomic sequence is "identified" as the promoter. These methods do not yield the cloned promoter or allow promoter mutations to be evaluated.

SUMMARY

In one aspect, provided is a DNA construct. In some embodiments, DNA construct comprises the following operably linked polynucleotide elements in the 5' to 3' direction:
 i) a promoter;
 ii) a hammerhead ribozyme cleavage site;
 iii) a hammerhead ribozyme catalytic core;
 iv) a first hairpin ribozyme cleavage site in the antisense orientation;
 v) a non-functional or stuffer polynucleotide;
 vi) a second hairpin ribozyme cleavage site in the antisense orientation;
 vii) a hairpin ribozyme catalytic core in the antisense orientation;
 viii) reverse and forward primer annealing sites in the antisense orientation;
 ix) an inserted polynucleotide suspected of comprising a RNA promoter; and
 x) a third ribozyme catalytic core, wherein the third ribozyme catalytic core is in the sense orientation, is not a hairpin ribozyme catalytic core and does not comprise a hairpin ribozyme cleavage site. In some embodiments, the promoter is functional in a prokaryotic cell. In varying embodiments, the promoter functional in a prokaryotic cell comprises a bacteriophage promoter selected from the group consisting of T7, T3 and SP6. In some embodiments, the promoter is functional in a eukaryotic cell. In some embodiments, the third ribozyme catalytic core comprises a hammerhead ribozyme catalytic core without a hairpin cleavage site at its 3' end. In some embodiments, the third ribozyme catalytic core comprises a positive or negative strand hepatitis delta virus (HDV) ribozyme catalytic core. In some embodiments, the DNA construct has a length of from about 600 bp to about 1600 bp. In varying embodiments, the DNA construct has a polynucleotide sequence having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO:1. In varying embodiments, the DNA construct has a polynucleotide sequence having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO:9. In varying embodiments, the DNA construct has a polynucleotide sequence having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO:10. In varying embodiments, the DNA construct has a polynucleotide sequence having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO:11.

In a further aspect, provided is a RNA construct. In some embodiments, RNA construct comprises the following operably linked polynucleotide elements in the 5' to 3' direction:
 i) a hammerhead ribozyme catalytic core;
 ii) a first hairpin ribozyme cleavage site in the antisense orientation;
 iii) a non-functional or stuffer polynucleotide;
 iv) a second hairpin ribozyme cleavage site in the antisense orientation;
 v) a hairpin ribozyme catalytic core in the antisense orientation;
 vi) reverse and forward primer annealing sites in the antisense orientation; and
 vii) an inserted polynucleotide suspected of comprising a RNA promoter.

With respect to embodiments of the DNA and RNA constructs, in some embodiments, the hammerhead ribozyme catalytic core is from a hammerhead ribozyme selected from the group consisting of Type I, Type II, Type III, HH9 and HH10. In varying embodiments, the hammerhead ribozyme catalytic core is from a Type III hammerhead ribozyme. In varying embodiments, the first and/or second hairpin ribozyme cleavage sites have a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO:7. In varying embodiments, the first and/or second hairpin ribozyme cleavage sites have a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO:6. In varying embodiments, the non-functional or stuffer polynucleotide does not comprise any one of a functional RNA promoter, a primer annealing site, or a transcription modifying sequence. In varying embodiments, wherein non-functional or stuffer polynucleotide comprises from about 200 base pairs (bp) to 1000 base pairs. In varying embodiments, the hairpin ribozyme catalytic core is or is derived from (e.g., is a variant of) the negative strand self-cleavage domain of a plant virus satellite RNA selected from the group consisting of the satellite RNA of tobacco ringspot virus (sTRSV), the satellite RNA of *arabis* mosaic virus (sArMV), and the satellite RNA of chicory yellow mottle virus (sCYMV). In varying embodiments, the hairpin ribozyme catalytic core is derived from the negative strand self-cleavage domain of the satellite RNA of tobacco ringspot virus (sTRSV). In varying embodiments, the hairpin ribozyme catalytic core comprises a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO:8. In varying embodiments, the hairpin ribozyme catalytic core comprises a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO:3. In varying embodiments, the hairpin ribozyme catalytic core comprises a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO:4. In varying embodiments, the hairpin ribozyme catalytic core comprises a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO:5. In varying embodiments, the inserted polynucleotide suspected of comprising a RNA promoter is from a library of randomized chemically synthesized DNA sequences. In varying embodiments, the inserted polynucleotide suspected of comprising a RNA promoter is from cDNA of a RNA virus genome. In varying embodiments, the inserted polynucleotide suspected of comprising a RNA promoter is fragmented genomic DNA, e.g., from an organism. In some embodiments, the inserted polynucleotide suspected of comprising a RNA promoter comprises a mutagenized RNA promoter. In varying embodiments, the inserted polynucleotide suspected of comprising a RNA promoter is from about 50 bp to about 200 bp.

In a further aspect, provided is a DNA plasmid comprising the DNA construct as described above and herein. In some embodiments, the plasmid has a size of from about 3000 bp to about 15000 bp.

In a further aspect, provided is a polynucleotide library comprising a population of the DNA or RNA constructs described above and herein, wherein each member of the population comprises a unique insert suspected of comprising a RNA promoter.

In a further aspect, provided is a host cell comprising the DNA or RNA construct or the DNA plasmid as described above and herein. In some embodiments, the host cell expresses a RNA dependent RNA polymerase. In varying embodiments, the host cell is transfected with a polynucleotide that encodes an exogenous RNA-dependent RNA polymerase. In some embodiments, the host cell is infected with a RNA virus. In some embodiments, the host cell is infected with a RNA virus from a virus taxonomic Order selected from the group consisting of Mononegavirales, Nidovirales, Picornavirales, and Tymovirales. In varying embodiments, the host cell is infected with a RNA virus from a virus taxonomic Group selected from the group of arenaviridae, astroviridae, barnaviridae, benyviridae, bromoviridae, bunyaviridae, caliciviridae, carmotetraviridae, closteroviridae, Flaviviridae, hepeviridae, leviviridae, luteoviridae, narnaviridae, nodaviridae, ophioviridae, orthomyxoviridae, permutotetraviridae, potyviridae, togaviridae, tombusviridae, virgaviridae. In varying embodiments, the host cell is infected with a RNA virus from a virus taxonomic Family selected from a group of celivirus, deltavirus, emaravirus, higrevirus, idaeovirus, ourmiavirus, polemovirus, sobemovirus, tenuivirus, umbravirus, or varicosavirus. In varying embodiments, the host cell is a prokaryotic cell or a eukaryotic cell. In varying embodiments, the host cell is selected from the group consisting of an archaeal cell, a bacterial cell, an animal cell (e.g., a mammalian cell or an insect cell), a plant cell or a fungal cell.

In a further aspect, provided is a method of identifying a RNA promoter. In some embodiments, the methods comprise the steps of:
a) transfecting a host cell with the DNA or RNA construct as described above and herein, wherein the 5' promoter is capable of promoting transcription in the host cell; wherein the host cell expresses a RNA-dependent RNA polymerase and rolling circle transcription of the RNA construct or RNA transcribed from the DNA construct within the host cell when the inserted polynucleotide comprises a functional RNA promoter yields a circularized RNA comprising:
  i) a hammerhead ribozyme catalytic core in the antisense orientation;
  ii) a hairpin ribozyme cleavage site;
  iii) a hairpin ribozyme catalytic core;
  iv) reverse and forward primer annealing sites; and
  v) the inserted polynucleotide comprising a functional RNA promoter;
b) isolating the circularized RNA;
c) amplifying the inserted polynucleotide comprising a functional RNA promoter; and
d) sequencing the inserted polynucleotide comprising a functional RNA promoter, thereby identifying the RNA promoter.

In another aspect, provided is a method of identifying a RNA promoter. In some embodiments, the method comprises the steps of:
a) transcribing in vitro into RNA the DNA construct as described above and herein, thereby producing a RNA transcript of the DNA construct;
b) transfecting a host cell with the RNA transcript, wherein the host cell expresses a RNA-dependent RNA polymerase and rolling circle transcription of the RNA construct within the host cell when the inserted polynucleotide comprises a functional RNA promoter yields a circularized RNA comprising:
  i) a hammerhead ribozyme catalytic core in the antisense orientation;
  ii) a ribozyme cleavage site;
  iii) a hairpin ribozyme catalytic core;
  iv) reverse and forward primer annealing sites; and
  v) the inserted polynucleotide comprising a functional RNA promoter;
c) isolating the circularized RNA;
d) amplifying the inserted polynucleotide comprising a functional RNA promoter; and
e) sequencing the inserted polynucleotide comprising a functional RNA promoter, thereby identifying the RNA promoter.

With respect to embodiments of the methods, in some embodiments, the host cell is infected with a RNA virus. In some embodiments, the host cell is infected with a RNA virus from a virus taxonomic Order selected from the group consisting of Mononegavirales, Nidovirales, Picornavirales, and Tymovirales. In varying embodiments, the host cell is transfected with a polynucleotide that encodes an exogenous RNA-dependent RNA polymerase. In varying embodiments, the host cell is infected with a RNA virus from a virus taxonomic Group selected from the group of arenaviridae, astroviridae, barnaviridae, benyviridae, bromoviridae, bunyaviridae, caliciviridae, carmotetraviridae, closteroviridae, flaviviridae, hepeviridae, leviviridae, luteoviridae, narnaviridae, nodaviridae, ophioviridae, orthomyxoviridae, permutotetraviridae, potyviridae, togaviridae, tombusviridae, virgaviridae. In varying embodiments, the host cell is infected with a RNA virus from a virus taxonomic Family selected from a group of celivirus, deltavirus, emaravirus, higrevirus, idaeovirus, ourmiavirus, polemovirus, sobemovirus, tenuivirus, umbravirus, or varicosavirus. In varying embodiments, the host cell is a prokaryotic cell or a eukaryotic cell. In varying embodiments, the host cell is selected from the group consisting of an archaeal cell, a bacterial cell, an animal cell (e.g., a mammalian cell or an insect cell), a plant cell or a fungal cell. In some embodiments, the sequencing comprises deep sequencing.

DEFINITIONS

The term "RNA promoter" refers to a promoter in a polyribonucleotide that binds to a RNA dependent RNA polymerase and leads to production of a complementary RNA transcript.

The term "ribozyme catalytic core" refers to the subsequence of a ribozyme capable of carrying out cleavage of a RNA molecule.

The term "ribozyme cleavage site" refers to the sequences recognized and cleaved by a ribozyme catalytic core.

The term "mini-monomer cassette" refers to a polynucleotide sequence comprising a ribozyme catalytic core and upstream and downstream ribozyme cleavage sites, such that when transcribed into RNA, the ribozyme catalytic core self-cleaves the mini-monomer cassette at the upstream and downstream ribozyme cleavage sites out of the context of a longer polynucleotide. The 5' and 3' ends of the excised polynucleotide ligate to form a circularized polynucleotide.

The terms "identical" or percent "identity," and variants thereof in the context of two or more polynucleotide or two or more amino acid sequences, refer to two or more sequences or subsequences that are the same. Sequences are "substantially identical" if they have a specified percentage of nucleic acid residues or amino acid residues that are the same (i.e., at least 60% identity, optionally at least 65%, 70%, 75%, 80%, 85%, 90%, 95%, 96%, 97%, 98%, or 99% identity to a reference sequence (e.g., SEQ ID NOs: 1-8) over a specified region (or the whole reference sequence when not specified)), when compared and aligned for maximum correspondence over a comparison window, or designated region as measured using any sequence comparison algorithm known in the art (GAP, BESTFIT, BLAST, Align, FASTA, and TFASTA in the Wisconsin Genetics Software Package, Genetics Computer Group (GCG), 575 Science Dr., Madison, Wis.), Karlin and Altschul Proc. Natl. Acad. Sci. (U.S.A.) 87:2264-2268 (1990) set to default settings, or by manual alignment and visual inspection (see, e.g., Ausubel et al., Current Protocols in Molecular Biology (1995-2014). Optionally, the identity exists over a region that is at least about 100, 200, 300, 400, 500, 600, 800, 1000, or more, nucleic acids in length, or over the full-length of the sequence.

BRIEF DESCRIPTION OF THE DRAWINGS

FIGS. 8A-B illustrate a text map of a mini-monomer cassette sequence for RNA promoter selection.

FIGS. 10A-E illustrate a text map of an in vitro production construct for MiniM cassette production for RNA promoter selection.

FIGS. 12A-P illustrate a text map of an in planta production construct for MiniM cassette production for RNA promoter selection.

FIGS. 14A-K illustrate a text map of an animal cell production construct for MiniM cassette production for RNA promoter selection.

DETAILED DESCRIPTION

1. Introduction

Provided are constructs and methods that employ hairpin ribozyme catalytic cores, e.g., such as the satellite RNA of tobacco ringspot virus (sTRSV) for identification of RNA promoters. sTRSV is a linear, 359 nucleotide, single stranded RNA which parasitizes the virus infections of its helper virus tobacco ringspot virus (TRSV). When present, it ameliorates the symptoms caused by the virus infection. It is encapsidated as a linear molecule in the virus capsid protein and uses the virus-encoded replication machinery to replicate. It has a complex secondary structure, shown in FIG. 1A that has a high degree of secondary structure.

Figure 2:
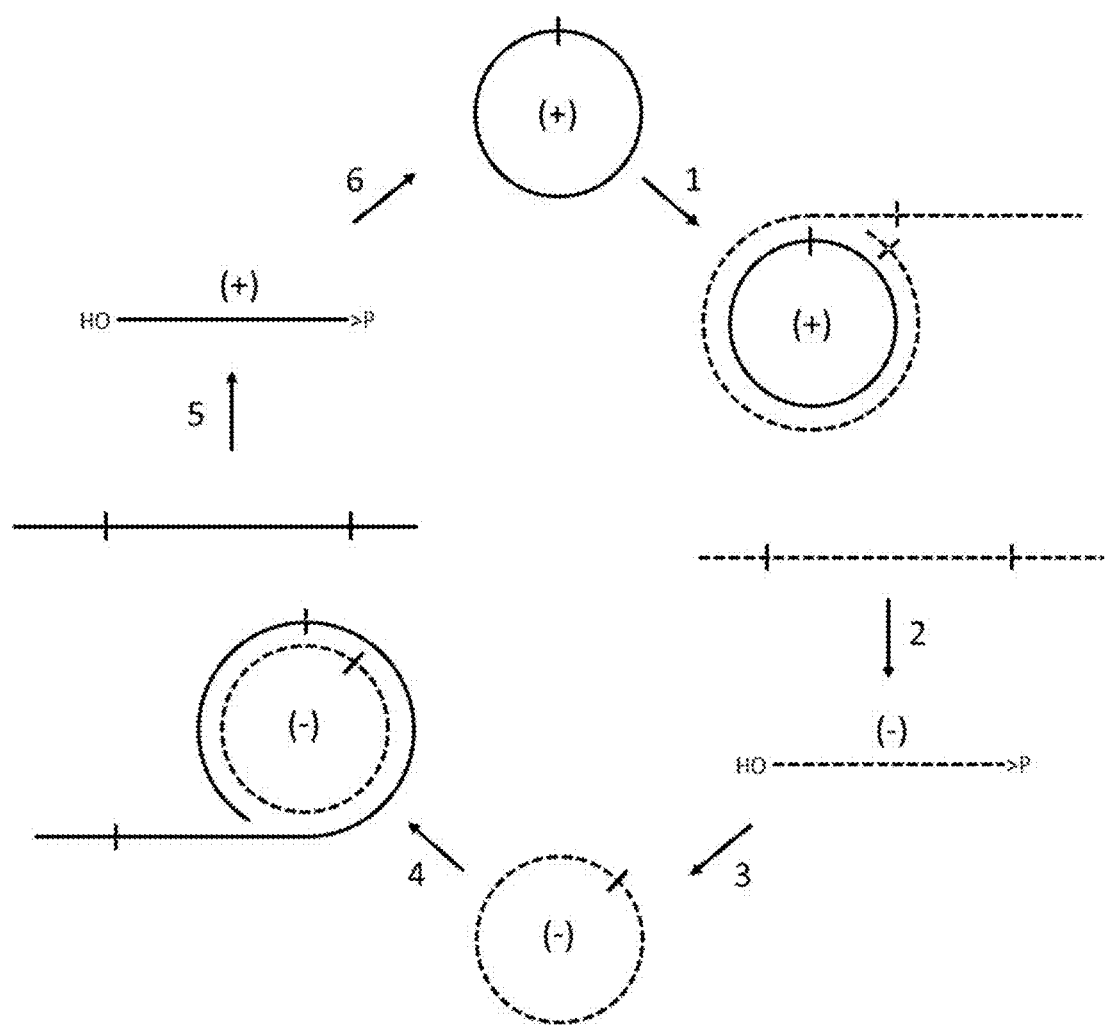
FIG. 2 illustrates the symmetrical rolling circle scheme for sTRSV replication. All sequences are RNA. The solid lines are the positive (+) strand and the dotted lines are the negative (−) strand. The positive strand is defined as that which is predominantly found in encapsidated in the viral capsids.

Within the secondary structure are two of the known ribozyme motifs—a hammerhead ribozyme (the filled box in FIG. 1A) in the positive (+) strand and a hairpin ribozyme (the unfilled boxes in FIG. 1A) in the negative (−) strand. Each is inactive when found in the complementary strand. One should also notice two things about these ribozymes, one, that while the hammerhead ribozyme is a contiguous region, the hairpin ribozyme is in two regions—the P and D regions, which function as the substrate for the more distant E region, which is the ribozyme core, and two, that the hammerhead and D region overlap by 5 nucleotides. These ribozymes play essential roles in sTRSV replication.

sTRSV replicates via a symmetrical rolling circle replication scheme as shown in FIG. 2. Linear (+) monomer sTRSV RNAs are found in the viral capsids. Inside cells this linear RNA is converted to a circular template by the action of a cellular enzyme (see, Chay, Guan and Bruening, *Virology*. (1997) 239(2):413-25) (step 6 in FIG. 2). This circular (+) sTRSV RNA is used by the TRSV helper virus RNA replication machinery as a template for rolling circle replication. Multimeric (−) sTRSV RNAs are produced (step 1 in FIG. 2). The hairpin ribozyme then cleaves these multimeric (−) sTRSV RNAs into linear (−) sTRSV monomers (step 2 in FIG. 2). Again through the reversible action of the hairpin ribozyme, the linear (−) sTRSV monomers are circularized (step 3 in FIG. 2). The circular (−) sTRSV RNAs are then used by the viral RNA replication machinery are then used for rolling circle replication producing multimeric (+) sTRSV RNA (step 4 in FIG. 2). The hammerhead ribozyme in the (+) sTRSV RNA then cleaves the multimeric (+) sTRSV RNA into monomers (step 5 in FIG. 2), completing the cycle.

Figure 1:
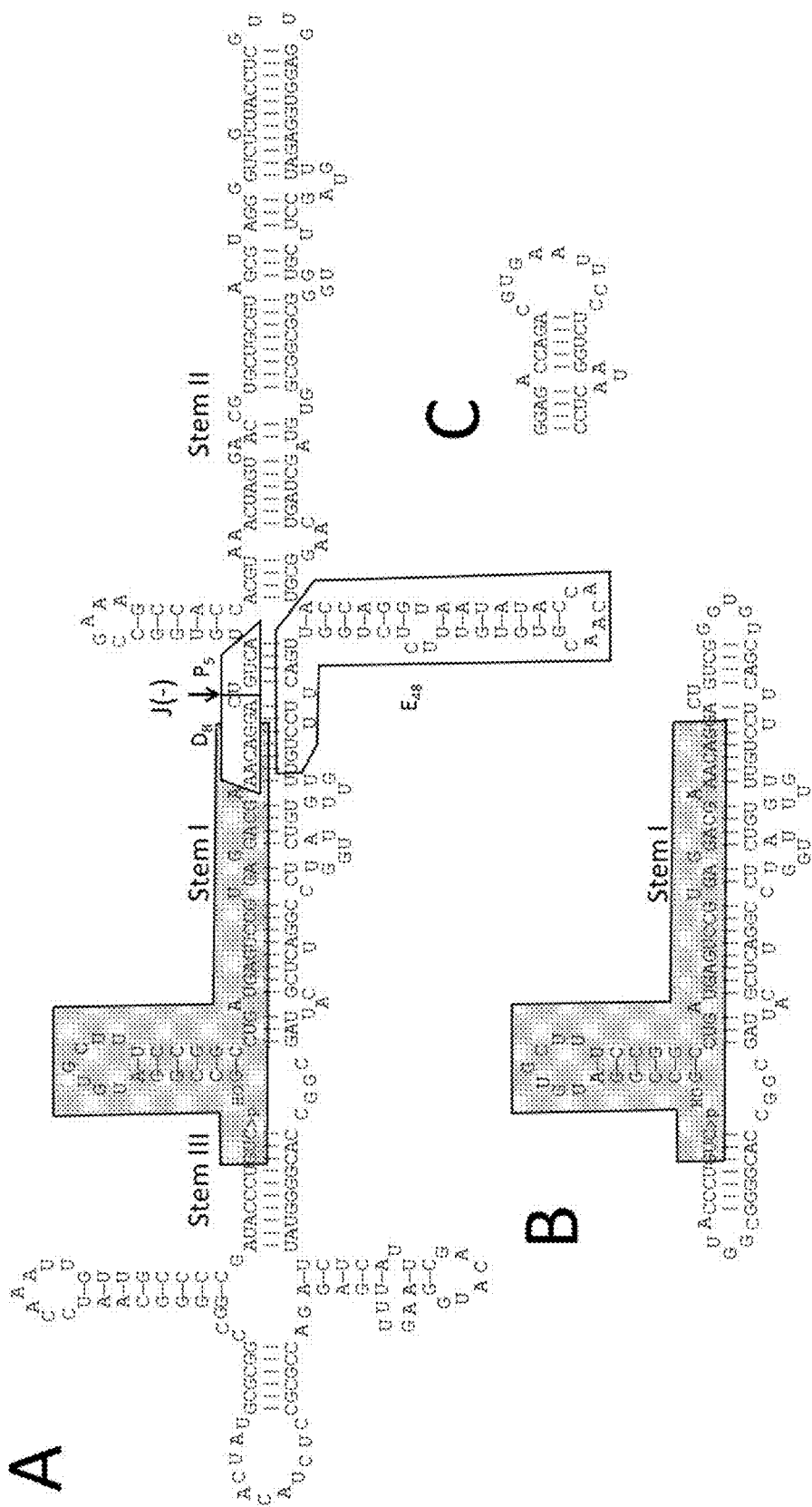
FIGS. 1A-C. A, Secondary structure of sTRSV. The filled box represents the region of the RNA encoding the hammerhead ribozyme. The unfilled box represents the region of the RNA, which in the negative strand encodes the hairpin ribozyme. B, A 126 nucleotide minimal sTRSV construct that is still capable of hammerhead ribozyme cleavage and which can be circularized by enzymatic action within cells. C, The proposed secondary structure of the Stem II region of a related satellite RNA from *arabis* mosaic virus (sArMV).
Figure 3:
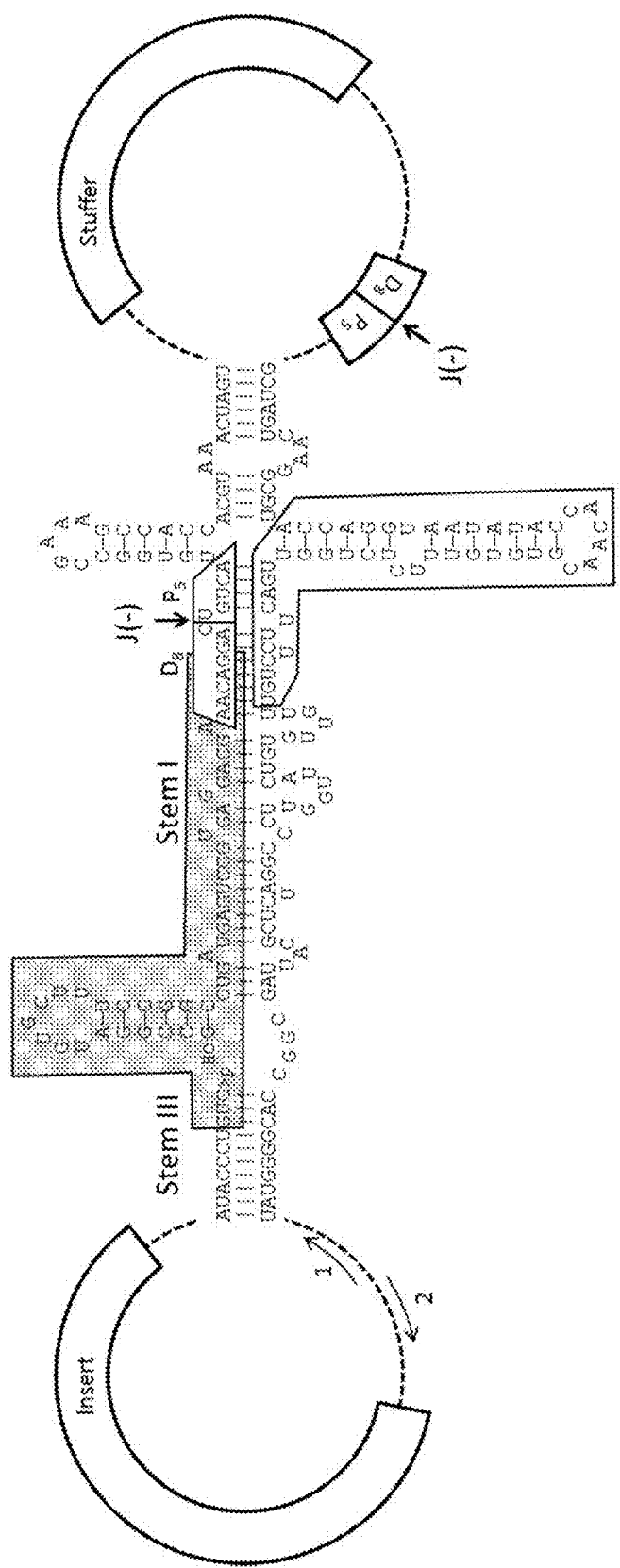
FIG. 3 illustrates a molecule for selecting RNA promoters from either viral or random sequences.

Chay, Guan and Bruening found that a much smaller construct containing the entire hammerhead region, but little else was capable of being efficiently circularized when produced inside cells (FIG. 1B). One should notice that the hairpin ribozyme core has been entirely deleted from this minimal circularizable (+) sTRSV RNA. Using this information and the smaller structure of Stem II from another related satellite RNA from *arabis* mosaic virus (sArMV) as shown in FIG. 1C, a molecule with the structure shown in FIG. 3 is constructed.

This molecule contains sequences for both ribozymes to function as well as the entire sequence of Stem III compared to the truncated Stem III sequence in the minimal circularizable (+) sTRSV RNA (FIG. 1B) and a truncated Stem II consistent with the structure of the sArMV sTRSV Stem II. New structures are attached to these Stem II and Stem III to form enlarged loops. The loop of the truncated Stem II contains a stuffer RNA sequence, which increases the overall size of the RNA, but provides no other function, and a second copy of the P and D regions of the hairpin ribozyme, the regions that are acted on by the ribozyme core. The loop of Stem III contains an insert sequence, which can either be fragments of viral RNA, organismal genomic or random sequences, for example 50 random nucleotides (50 Ns, where N could be any nucleotide) and primer binding sites for reverse transcriptase-polymerase chain reaction.

Figure 4:
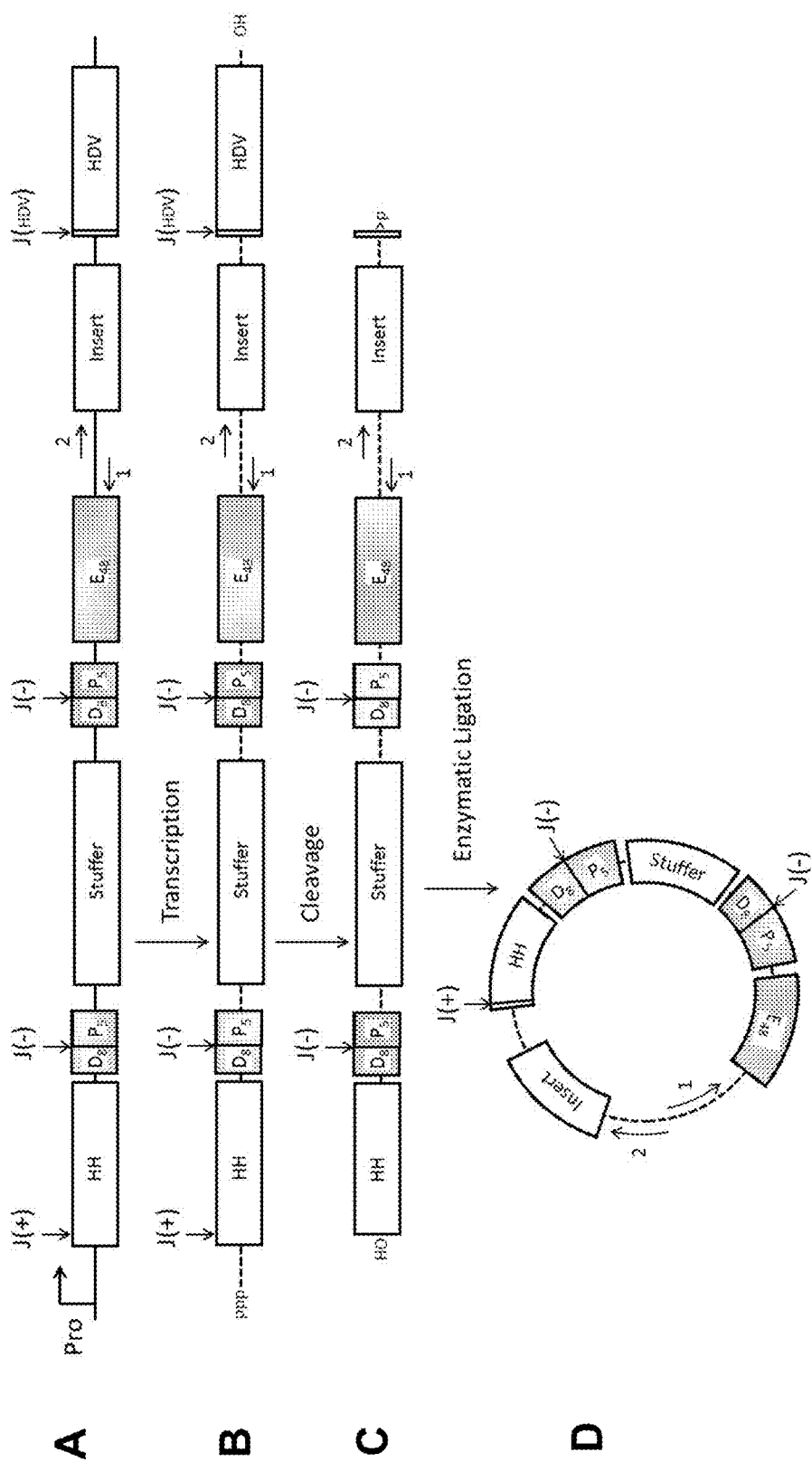
FIGS. 4A-D illustrate construct and production of molecule for selection of RNA promoters from any source, e.g., from viral cDNA, viral genomic, organismal genomic or random sequences. The uppermost line is an insert into a plasmid appropriate for either in vitro or in vivo production of RNA. Appropriate sequences for the plasmid necessary for either in vitro or in vivo use are included as appropriate or desired, for example, T-DNA borders for use in plants. DNA molecules are shown as solid lines while RNA sequences are shown as dotted lines. The promoter (Pro) could be for in vitro production, for example, the T7 RNA polymerase promoter, or for in vivo production, for example, a plant promoter for production of the desired molecules inside plant cells. The HDV ribozyme (HDV) would be substituted for what would normally be another hammerhead ribozyme (HH). The sequences that are shaded are not functional as they are the complements of the active sequences.

This molecule is produced from the construct shown in FIG. 4. This construct can be used for in vitro production of the linear molecule shown after cleavage or the in vivo production of the circular molecule shown after enzymatic ligation. In vitro produced linear molecules are circularized by introduction into cells. Another known ribozyme, one of the two found in the hepatitis delta virus (HDV) sequence would substitute for a second hammerhead ribozyme to produce the 3' termini of the molecule. This embodiment removes the D region that is found overlapping with the hammerhead ribozyme sequence to prevent accidental formation of negative circular RNAs from spurious transcription in the opposite direction of the promoter shown (Pro) by sequences outside those shown. Transcription produces the unprocessed primary transcript followed by hammerhead and HDV ribozyme cleavage to generate the appropriate 5' and 3' termini respectively.

Figure 5:
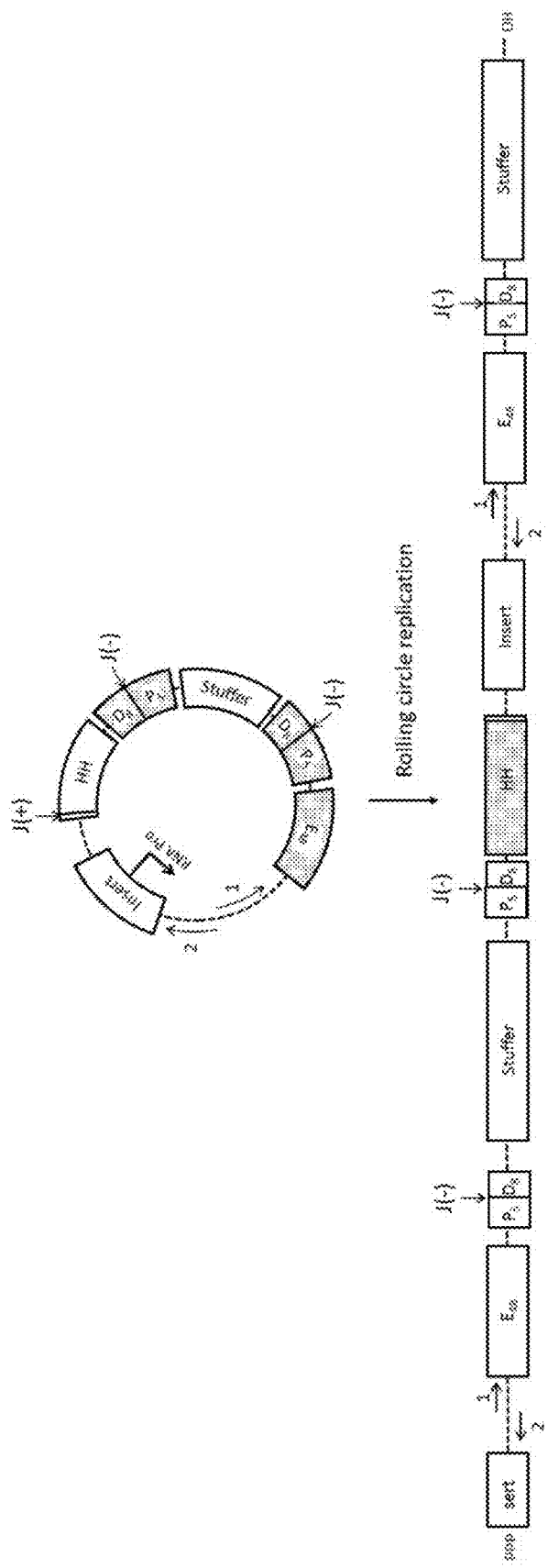
FIG. 5 illustrates rolling circle replication of the molecule for selection of RNA promoters. In the circular molecule, the 5' to 3' direction is clockwise on the circle. In the linear multimer produced by replication of the circular molecule the 5' to 3' direction is from left to right. The 5' most sequence of the new RNA synthesized is a fragment of the insert sequence. While the newly synthesized RNA is shown only through the second stuffer sequence, it is shown this way for convenience only and should be longer than this depending on the ability of the viral replication machinery to synthesize longer RNAs. Notice that in the newly synthesized RNA the hammerhead sequences (HH) are shaded (non-functional due to being the complementary sequence) and the E, P and D sequences are not shaded (functional).
Figure 6:
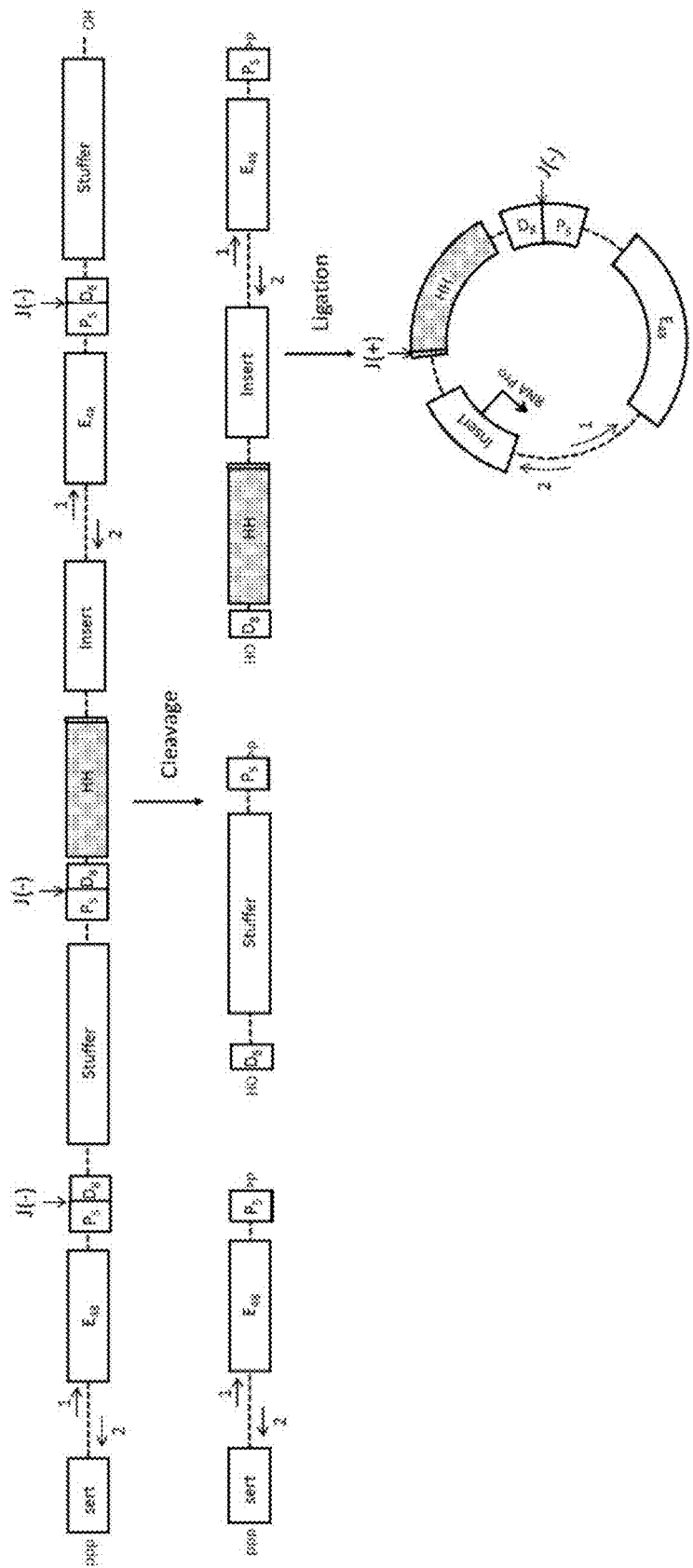
FIG. 6 illustrates processing of the newly synthesized primary transcript. The primary transcript is shown at the top with the fully processed products are below it. For every one of the 5' most fragment, there should be multiple stuffer and insert fragments.

Production of the circular RNA or introduction of the linear RNA followed by circularization would take place in virus infected material (plants, animal cells culture, etc.). In this way, viral replication machinery is already present within the cells. In most cases, the inserted sequences within the left terminal loop do not contain a sequence that can interact with the viral replication machinery so no complementary RNA is generated. In some cases, the viral replication machinery interacts with the insert sequence and complementary sequences are generated as shown in FIG. 5. Processing of this newly synthesized primary transcript is shown in FIG. 6. The newly synthesized stuffer-containing fragments are not circularized because they do not contain a ribozyme core. The stuffer sequences also do not contain the primer binding sites and so are not recovered after RT-PCR. The newly synthesized insert-containing fragments do contain a ribozyme core and therefore are circularized and recoverable by RT-PCR with reverse and forward primers (e.g., primers 1 and 2). Deep sequencing of the insert-containing fragments identifies the sequences that are recognizable by the viral replication machinery. Subsequent rounds of selection after mutagenesis can improve the RNA promoter function.

Once selected, these viral RNA promoter molecules can be used directly as antiviral agents as they compete for viral RNA replication machinery, or the viral RNA promoters can be combined with an anti-RNA virus gene, like RNase to make a novel anti-viral gene, which is only be expressed when the virus is present. These novel anti-viral genes can be used directly as RNAs by introduction into virus-infected cells by liposome or other means, or can be used to make transgenic organisms resistant to virus infection.

2. Constructs

The constructs described herein are generally synthetic and/or recombinant. The constructs can be comprised wholly of naturally occurring nucleic acids, or in certain embodiments can contain one or more nucleic acid analogues or derivatives. The nucleic acid analogues can include backbone analogues and/or nucleic acid base analogues and/or utilize non-naturally occurring base pairs. Illustrative artificial nucleic acids that can be used in the present constructs include, without limitation, nucleic backbone analogs peptide nucleic acids (PNA), morpholino and locked nucleic acids (LNA), bridged nucleic acids (BNA), glycol nucleic acids (GNA) and threose nucleic acids (TNA). Nucleic acid base analogues that can be used in the present constructs include, without limitation, fluorescent analogs (e.g., 2-aminopurine (2-AP), 3-Methylindole (3-MI), 6-methyl isoxanthoptherin (6-MI), 6-MAP, pyrrolo-dC and derivatives thereof, furan-modified bases, 1,3-Diaza-2-oxophenothiazine (tC), 1,3-diaza-2-oxophenoxazine); non-canonical bases (e.g., inosine, thiouridine, pseudouridine, dihydrouridine, queuosine and wyosine), 2-aminoadenine, thymine analogue 2,4-difluorotoluene (F), adenine analogue 4-methylbenzimidazole (Z), isoguanine, isocytosine; diaminopyrimidine, xanthine, isoquinoline, pyrrolo[2,3-b]pyridine; 2-amino-6-(2-thienyl)purine, pyrrole-2-carbaldehyde, and universal bases (e.g., 2' deoxyinosine (hypoxanthine deoxynucleotide) derivatives, nitroazole analogues). Non-naturally occurring base pairs that can be used in the present constructs include, without limitation, isoguanine and isocytosine; diaminopyrimidine and xanthine; 2-aminoadenine and thymine; isoquinoline and pyrrolo[2,3-b]pyridine; 2-amino-6-(2-thienyl)purine and pyrrole-2-carbaldehyde; two 2,6-bis(ethylthiomethyl)pyridine (SPy) with a silver ion; pyridine-2,6-dicarboxamide (Dipam) and a mondentate pyridine (Py) with a copper ion.

Provided are constructs useful for the identification of RNA promoters, e.g., from sequences suspected of encoding a RNA promoter. The constructs can be DNA or RNA and generally comprise following operably linked polynucleotide elements in the 5' to 3' direction:

i) a hammerhead ribozyme catalytic core;
ii) a first hairpin ribozyme cleavage site in the antisense orientation;
iii) a non-functional or stuffer polynucleotide;
iv) a second hairpin ribozyme cleavage site in the antisense orientation;
v) a hairpin ribozyme catalytic core in the antisense orientation;
vi) reverse and forward primer annealing sites in the antisense orientation; and
vii) an inserted polynucleotide suspected of comprising a RNA promoter. See, FIG. 4. In varying embodiments, the DNA and/or RNA constructs have a length of about 600 bp to about 1600 bp.

a. DNA Constructs

The DNA constructs generally comprise the following operably linked polynucleotide elements in the 5' to 3' direction:

i) a promoter;
ii) a hammerhead ribozyme cleavage site;
iii) a hammerhead ribozyme catalytic core;
iv) a first hairpin ribozyme cleavage site in the antisense orientation;
v) a non-functional or stuffer polynucleotide;
vi) a second hairpin ribozyme cleavage site in the antisense orientation;
vii) a hairpin ribozyme catalytic core in the antisense orientation;
viii) reverse and forward primer annealing sites in the antisense orientation;
ix) an inserted polynucleotide suspected of comprising a RNA promoter; and
x) a third ribozyme catalytic core, wherein the third ribozyme catalytic core is in the sense orientation, is not a hairpin ribozyme catalytic core and does not comprise a hairpin ribozyme cleavage site.

i. Promoter

The 5' or upstream promoter allows transcription of the entire or full length of the construct into RNA. The ribozyme cleavage sites within the first and third ribozyme catalytic core sequences can then be cleaved by the first and third ribozyme catalytic cores, respectively.

For in vivo transcription of the full length of construct, the selected promoter is active in a selected host cell. For example, if the DNA construct is introduced into a eukaryotic cell, the selected 5' or upstream promoter is biologically active in the eukaryotic cell. As appropriate, the 5' or upstream promoter can be a mammalian promoter that actively promotes transcription in a mammalian host cell. In some embodiments, the 5' or upstream promoter can be a plant promoter that actively promotes transcription in a plant host cell.

For in vitro transcription of the full length of construct, the 5' or upstream promoter is any RNA polymerase promoter suitable for in vitro transcription. In varying embodiments, the 5' or upstream promoter is a bacteriophage promoter, e.g., a T7, a T3 or SP6 bacteriophage promoter.

In vivo and in vitro transcription of the DNA construct produces a RNA construct as described herein. The RNA construct may or may not be cleaved at the ribozyme cleavage sites within the first and third ribozyme cleavage sites.

ii. 5' Hammerhead Ribozyme Catalytic Core

The first and 5'-most ribozyme catalytic core is a hammerhead ribozyme catalytic core. This first and 5'-most hammerhead ribozyme catalytic core is in the positive strand orientation and includes a hammerhead ribozyme cleavage site at or near its 5'-end. The first and 5'-most hammerhead ribozyme catalytic core is positioned or located 5' to the first hairpin ribozyme cleavage site, as depicted in FIG. 4.

The minimal hammerhead sequence required for the self-cleavage reaction includes approximately 13 conserved or invariant "core" nucleotides, most of which are not involved in forming canonical Watson-Crick base-pairs. The core region is flanked by Stems I, II and III, which are in general made of canonical Watson-Crick base-pairs but are otherwise not constrained with respect to sequence. Functionally, a hammerhead ribozyme performs a chemical reaction that results in the breakage of the substrate strand of RNA, specifically at C17, the cleavage-site nucleotide.

Structurally, the hammerhead ribozyme is composed of three base paired helices, separated by short linkers of conserved sequences. These helices are called I, II and III. Hammerhead ribozymes can be classified into three types based on which helix the 5' and 3' ends are found in. If the 5' and 3' ends of the sequence contribute to stem I then it is a type I hammerhead ribozyme, to stem II is a type II and to stem III then it is a type III hammerhead ribozyme. In varying embodiments, the first and 5'-most hammerhead ribozyme catalytic core can be a Type I, Type II, Type III, HH9 and HH10 hammerhead ribozyme catalytic core.

The structure and function of hammerhead ribozymes is well-characterized in the art, and has been reviewed in, e.g., Scott, et al., *Prog Mol Biol Transl Sci*. (2013) 120:1-23; Lee, et al., *Prog Mol Biol Transl Sci*. (2013) 120:25-91; and Hammann, et al., RNA. (2012) 18(5):871-85.

iii. 5' Hammerhead Ribozyme Cleavage Site

A hammerhead ribozyme cleavage site is located or positioned within and near the 5'-end of the first and 5'-most hammerhead ribozyme catalytic core.

The hammerhead ribozyme becomes active to cleave at the hammerhead ribozyme cleavage site when the construct is RNA. As a result of cleavage at the hammerhead ribozyme cleavage site within the hammerhead ribozyme catalytic core, the 5'-product possesses a 2',3'-cyclic phosphate terminus, and the 3'-product possesses a 5'-OH terminus.

The hammerhead ribozyme is capable of cleaving immediately after a NHH sequence, where N is any nucleotide and H is an A, C or U nucleotide. There is also a structural requirement for the N and first H nucleotide to be base paired, reviewed in Kore, et al., *Nucl. Acid Res.*, (1998), 26, 4116-20.

iv. Hairpin Ribozyme Cleavage Sites

The DNA and RNA constructs comprise first (upstream) and second (downstream) antisense hairpin ribozyme cleavage sites. The first or upstream antisense ribozyme cleavage site is located 3' to or downstream of the first or upstream hammerhead ribozyme catalytic core and 5' to or upstream of the non-functional stuffer polynucleotide. The second or downstream antisense ribozyme cleavage site is located 3' to or downstream of the non-functional stuffer polynucleotide and 5' to or upstream of the antisense hairpin ribozyme catalytic core. See, FIG. 4, which depicts the primary DNA construct and primary RNA transcript.

Figure 7:
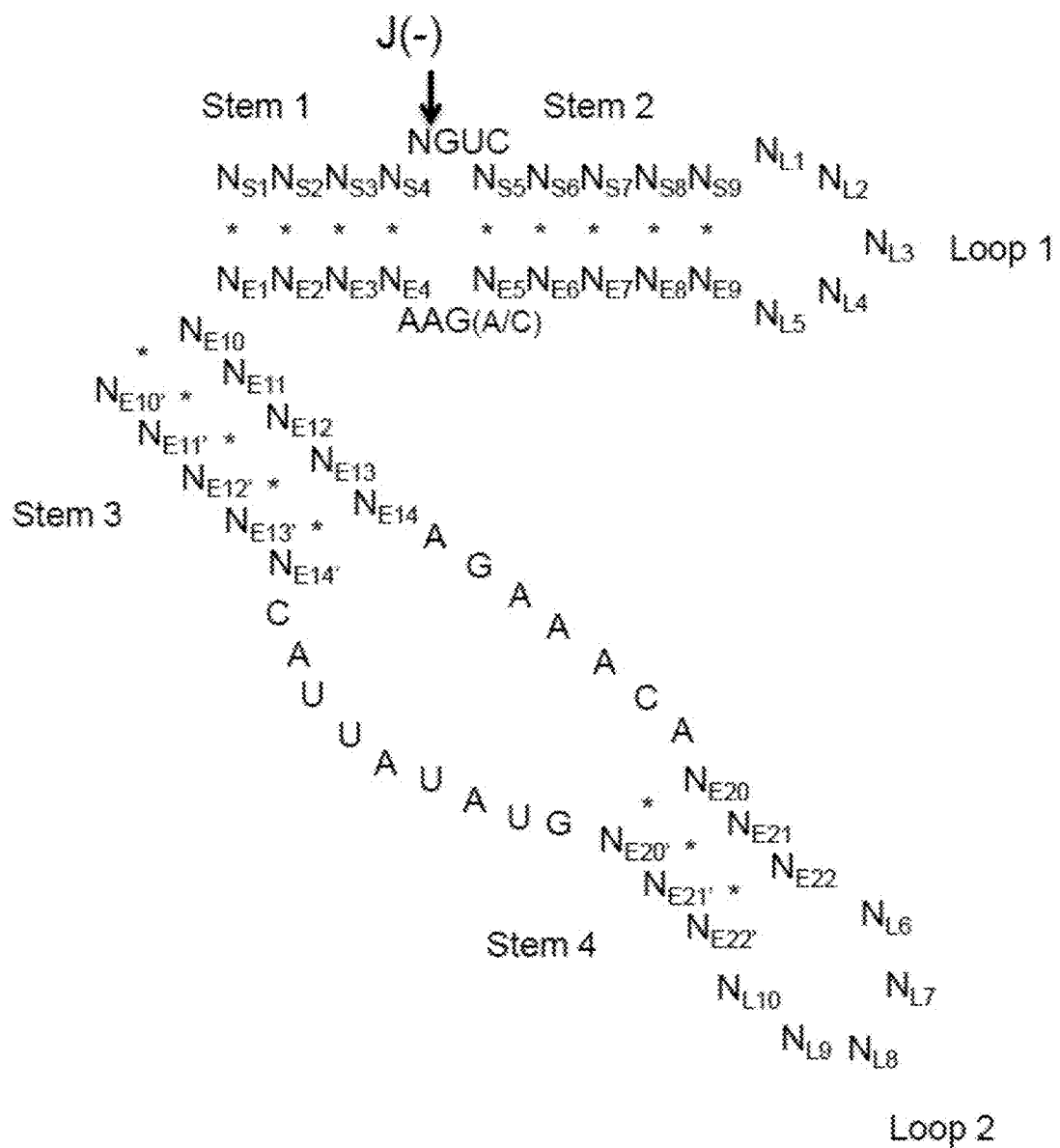
FIG. 7 illustrates a depiction of a generalized structure of the P-D regions and ribozyme core regions and their interactions.
Figure 9:
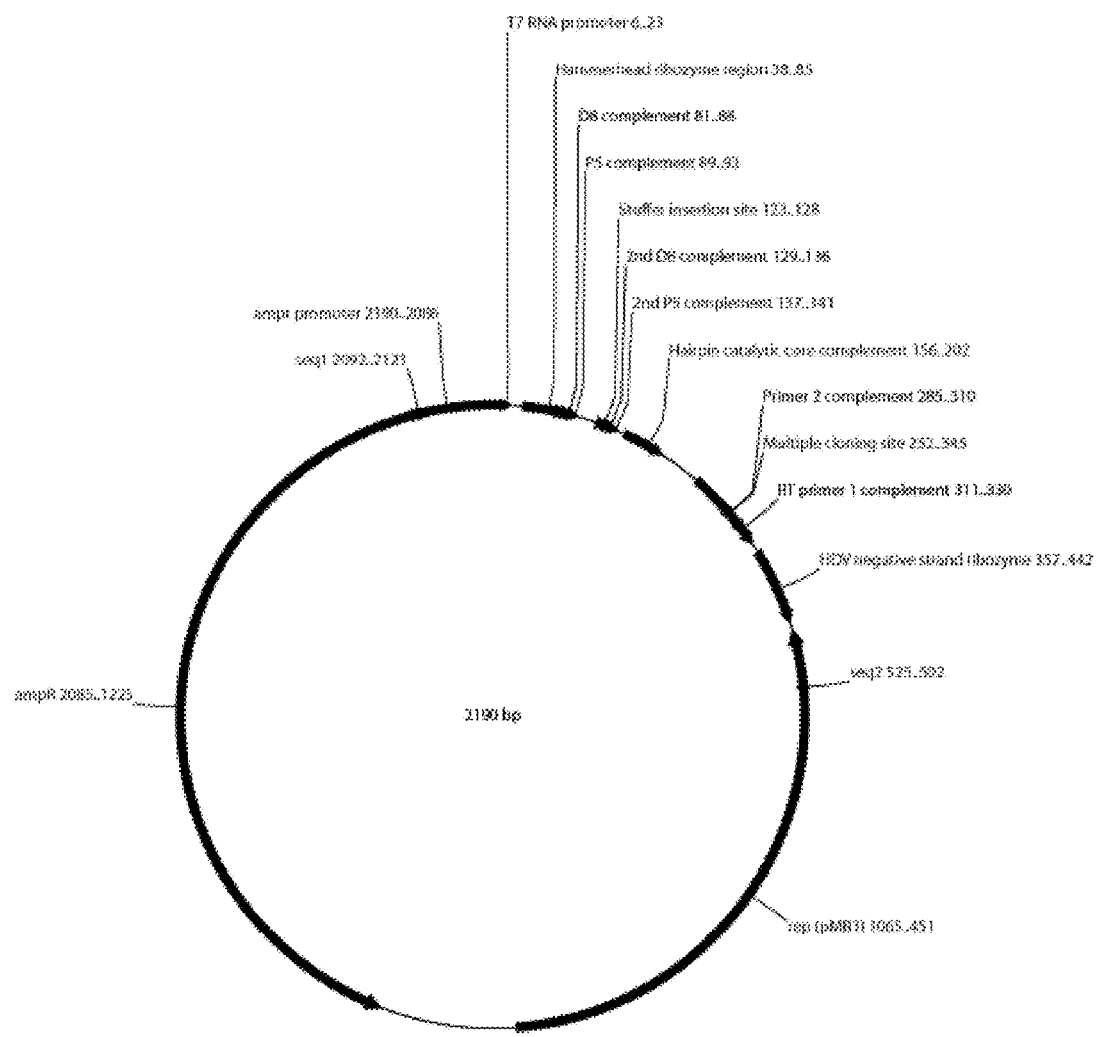
FIG. 9 illustrates a plasmid schematic of an in vitro production construct for MiniM cassette production for RNA promoter selection.
Figure 11:
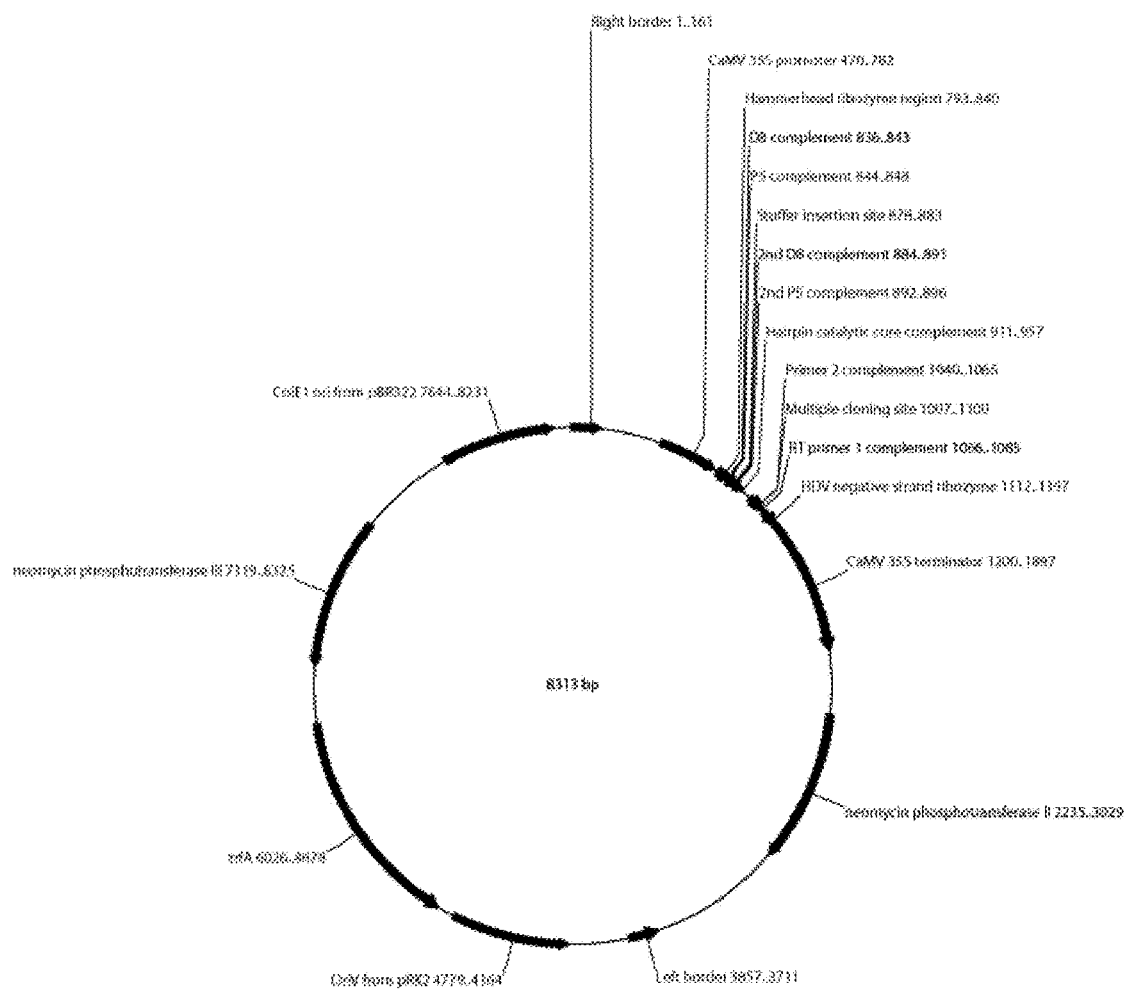
FIG. 11 illustrates a plasmid schematic of an in piano production construct for MiniM cassette production for RNA promoter selection. The illustrated in planta construct is a derivative of pEAQ-HT, a known plasmid for plant expression. See, e.g., Peyret, et al., *Plant Mol Biol.* (2013) 83(1-2):51-8.
Figure 13:
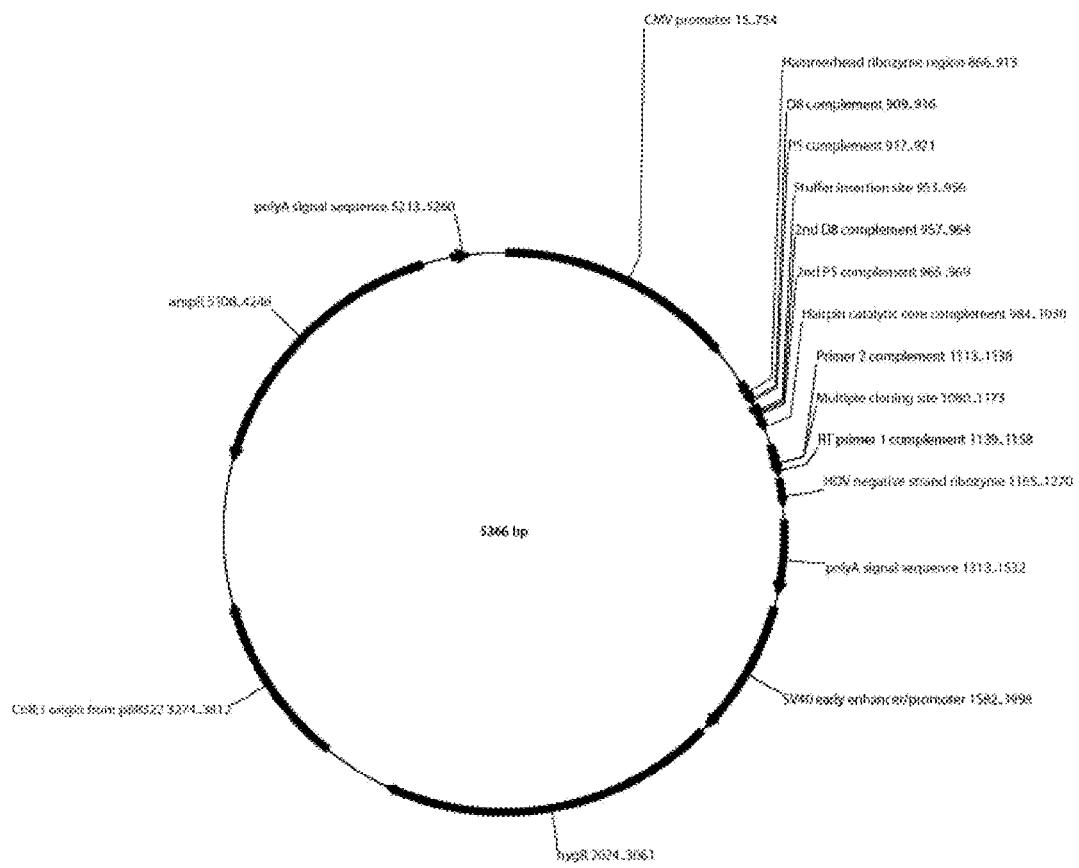
FIG. 13 illustrates a plasmid schematic of an animal cell production construct for MiniM cassette production for RNA promoter selection. The illustrated animal cell construct is a derivative of pNL 3.2, a known cytomegalovirus promoter-containing expression vector (commercially available from Promega; promega.com).

The hairpin ribozyme cleavage sites in the DNA and RNA constructs can be any polynucleotide sequence capable of being cleaved by a hairpin ribozyme. A generalized or consensus ribozyme is provided in SEQ ID NO:7. As depicted in FIG. 7, the sequence and structure of the ribozyme cleavage sites are guided by the polynucleotide sequence of the hairpin ribozyme catalytic core. Interactions between the ribozyme cleavage site (as generalized in SEQ ID NO:7) and the negative strand self-cleavage domain (as generalized in SEQ ID NO:8) are via hydrogen bonds forming two stems—1 and 2 (as depicted in FIG. 7).

Stem 1 is formed by hydrogen bonds between NS1 and NE1, NS2 and NE2, NS3 and NE3, NS4 and NE4

Stem 2 is formed by hydrogen bonds between NS5 and NE5, NS6 and NE6, NS7 and NE7, NS8 and NE8, NS9 and NE9

Interactions within the generalized negative strand self-cleavage and ligation domain form 2 stems—3 and 4

Stem 3 is formed by hydrogen bonds between NE10 and NE10', NE11 and NE11', NE12 and NE12', NE13 and NE13', NE14 and NE14'

Stem 4 is formed by hydrogen bonds between NE20 and NE20', NE21 and NE21', and NE22 and NE22'

Stem 1 is essentially universally 4 base pairs long

Stem 2 can be as short as 4 base pairs, but can be longer

Stem 3 is essentially universally 5 base pairs long

Stem 4 is from 2 to 4 base pairs long depending on the source

Loop 1 can be as small as 4 nucleotides, if it is a special sequence called a tetra-loop, but can be longer, e.g., 100's of nucleotides up to 1000 nucleotides Loop 2 varies from 4 to 6 bases long in natural sequences The polynucleotide sequences of an illustrative hairpin ribozyme cleavage site is provided herein as SEQ ID NO:6. In varying embodiments, the hairpin ribozyme cleavage site comprises a polynucleotide sequence having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO:6.

Generally, the polynucleotide sequences of the first and second hairpin ribozyme cleavage sites are the same.

v. Hairpin Ribozyme Catalytic Core

The DNA and RNA constructs and DNA plasmids described herein can comprise the antisense of any functional hairpin ribozyme catalytic core known in the art. The antisense hairpin ribozyme catalytic core is positioned or located 3' to or downstream of the second antisense hairpin ribozyme cleavage site and 5' to or upstream of the forward and reverse primer annealing polynucleotides. This hairpin ribozyme catalytic core is in the negative strand orientation (e.g., antisense orientation to the hammerhead ribozyme catalytic core).

The hairpin ribozyme catalytic core polynucleotides of use, when in the sense orientation, are capable of self-cleaving itself and flanking sequences within ribozyme cleavage sites out of the context of a longer polynucleotide sequence and then ligating the excised polynucleotide into a circularized polynucleotide. The hairpin ribozyme catalytic core polynucleotides are in the inactive, antisense form in the primary RNA transcript. In varying embodiments, the hairpin ribozyme catalytic core can be derived from a naturally occurring source. For example, Rubino, et al, *J Gen Virol* (1990) 71:1897-1903 describes examples of naturally-derived and consensus sequences of hairpin ribozyme catalytic core polynucleotides. In varying embodiments, the hairpin ribozyme catalytic core is or is derived from the negative strand self-cleavage domain of a satellite RNA of a plant virus, e.g., the satellite RNA of tobacco ringspot virus (sTRSV), the satellite RNA of *arabis* mosaic virus (sArMV), and the satellite RNA of chicory yellow mottle virus (sCYMV). In varying embodiments, the hairpin ribozyme catalytic core is or is derived from the negative strand self-cleavage domain of a satellite RNA of the plant virus tobacco ringspot virus (sTRSV). In some embodiments, the hairpin ribozyme catalytic core polynucleotide is a synthetic sequence, e.g., based on naturally occurring or consensus hairpin ribozyme catalytic core sequences. The general structure for a hairpin ribozyme catalytic core is provided in FIG. 7. The structure of hairpin ribozyme catalytic cores are well known in the art, and described, e.g., in Müller, et al., *IUBMB Life*. (2012) 64(1):36-47; Fedor, *J Mol Biol*. (2000) 297(2):269-91; and Ferré-D'Amaré, *Biopolymers*. (2004) 73(1):71-8.

In varying embodiments, the hairpin ribozyme catalytic core can be or can be derived from (e.g., can be a variant of) a circularizing ribozyme. Examples include the *Neurospora* Varkud Satellite ribozyme ("VS ribozyme") and circularizing group I intron ribozyme (e.g., circularizing introns from Tetrahymena. The structure and sequence of the VS ribozyme is known in the art, and described, e.g., in Bonneau, et al., *Biochemistry* (2014) 53(39):6264-75; Bouchard, et al., *RNA*. (2014) 20(9):1451-64; and Desjardins, et al, *Nucleic Acids Res*. (2011) 39(10):4427-37. The structure and sequence of circularizing group I intron ribozymes, including circularizing introns from Tetrahymena are known in the art and described, e.g., in Puttaraju and Been, *Nucl. Acid Res*. (1992), 20:5357-64; Puttaraju and Been, *J Biol Chem* (1996), 271:26081-7, Ford and Ares, *PNAS* (1994), 91:3117-21. Ribozyme structures and mechanisms are also reviewed in Doherty, et al., *Annu Rev Biochem*. (2000) 69:597-615.

A generalized or consensus negative strand self-cleavage domain of a hairpin ribozyme catalytic core is provided in SEQ ID NO:8. The polynucleotide sequences of illustrative hairpin ribozyme catalytic core molecules are provided herein as SEQ ID NOs: 3, 4 and 5. In varying embodiments, the hairpin ribozyme catalytic core comprises a polynucleotide sequence having at least about 60% sequence identity, e.g., at least about 65%, 70%, 75%, 80%, 85%, 90%, 91%, 92%, 93%, 94%, 95%, 96%, 97%, 98%, 99% or 100% sequence identity to any one of SEQ ID NOs:3, 4 or 5.

vi. Non-Functional or Stuffer Polynucleotide

The DNA and RNA constructs comprise a non-functional or stuffer polynucleotide. Generally, the non-functional or stuffer polynucleotide does not comprise any one of a functional RNA promoter, a primer annealing site, or a transcription modifying sequence. Accordingly, the non-functional or stuffer polynucleotide does not circularize and is not amplified. Generally, the non-functional or stuffer polynucleotide is located or positioned 3' to or downstream of the first hairpin ribozyme cleavage site and 5' to or upstream of the second ribozyme cleavage site. See, e.g., FIG. 4.

In varying embodiments, the non-functional or stuffer polynucleotide comprises from about 200 base pairs (bp) to 1000 base pairs. The non-functional or stuffer polynucleotide can be any size or length such that when it is cleaved out after rolling circle replication, it is of a distinguishable size (e.g., by electrophoresis) from the cleaved out polynucleotide comprising the hammerhead ribozyme catalytic core, insert containing a RNA promoter, primer annealing polynucleotides and hairpin ribozyme catalytic core. See, FIG. 6.

vii. Forward and Reverse RT-PCR Primer Annealing Polynucleotides

The DNA and RNA constructs comprise forward and reverse RT-PCR primer annealing polynucleotides. The forward and reverse RT-PCR primer annealing polynucleotides are each unique sequences in the constructs or DNA plasmids and generally abut each other or are located proximally to each other (e.g., within about 500, 400, 300, 200 or 100 nucleotides from one another) with the reverse RT-PCR primer annealing polynucleotide positioned 5' to the forward RT-PCR primer annealing polynucleotide. The forward and reverse RT-PCR primer annealing polynucleotides are positioned or located such that they are between the two ribozyme cleavage sites (e.g., the P-D regions) so they are excised as part of the mini-monomer cassette, and they face each other across the P-D region formed from the first and second P-D regions by ribozyme cleavage and ligation. The PCR product they make contains the insert region. In varying embodiments, the forward and reverse RT-PCR primer annealing polynucleotides are positioned or located such that they are 5' to or upstream of the insert suspected of containing a RNA promoter and 3' to or downstream of the hairpin ribozyme catalytic core. See, e.g., FIG. 4.

viii. Inserted Polynucleotide Suspected of Comprising a RNA Promoter

The DNA and RNA constructs comprise an inserted polynucleotide suspected of comprising a RNA promoter. The inserted polynucleotide suspected of comprising a RNA promoter is positioned or located 3' to or downstream of the forward and reverse primer annealing polynucleotides and 5' to or upstream of the third ribozyme catalytic core.

The inserted polynucleotide suspected of comprising a RNA promoter can be from any source, for example, a randomly generated library, a naturally occurring source (e.g., a genomic library), a chemically synthesized source, a mutated or mutagenized known RNA promoter, random polynucleotides, restriction fragments of eukaryotic DNA, or randomized PCR fragments of eukaryotic DNA. In varying embodiments, the inserted polynucleotide suspected of comprising a RNA promoter is variously fragmented genomic DNA from an organism, e.g., there may be RNA promoters present in genomic DNA. Generally, the polynucleotide suspected of comprising a promoter has from about 50 bp to about 200 bp. In varying embodiments, the polynucleotide suspected of comprising a promoter contains an entire promoter or a partial promoter. Within the inserted or captured polynucleotide suspected of comprising a promoter, the promoter may be centered or located more proximal to the 3' or 5' end. The methods of employing the DNA constructs described herein identify functional promoters, e.g., promoters capable of inducing, directing or promoting transcription, regardless of whether the entire promoter or a partial promoter is captured, or the location of the RNA promoter within the captured insert.

ix. Third Ribozyme Catalytic Core

The third ribozyme catalytic core is located or positioned 3' to or downstream of the inserted polynucleotide suspected of comprising a RNA promoter. The third or 3' ribozyme catalytic core is not a hairpin ribozyme catalytic core but can be in varying embodiments a hammerhead ribozyme catalytic core so long as the hammerhead ribozyme catalytic core does not comprise a hairpin cleavage site at its 3' end. Generally, the third ribozyme catalytic core is in the positive strand orientation (e.g., same or sense orientation to the hammerhead ribozyme catalytic core). In varying embodiments, the third ribozyme catalytic core comprises a positive or negative strand hepatitis delta virus (HDV) ribozyme catalytic core or a ribozyme catalytic core from a member of the HDV family. The structure of hepatitis delta virus (HDV) and HDV family members are known in the art. See, e.g., Riccitelli, et al., *Prog Mol Biol Transl Sci.* (2013) 120:123-71; Kapral, et al., *Nucleic Acids Res.* (2014) 42(20):12833-46.

Consensus sequences for the HDV negative strand (antigenomic) ribozyme has been examined by Nehdi and Perreault, *Nucl. Acid Res.* (2006) 34:584-92, and for the HDV positive strand (genomic) ribozyme has been examined by Chadalavada et al., RNA (2007) 13:2189-2201. General aspects of the HDV ribozyme structures and mechanisms of action are reviewed in Doherty and Doudna, *Ann. Rev. Biochem.* (2000) 69:597-615.

b. RNA Constructs

The DNA constructs generally comprise the following operably linked polynucleotide elements in the 5' to 3' direction:

i) a hammerhead ribozyme catalytic core;

ii) a first hairpin ribozyme cleavage site in the antisense orientation;

iii) a non-functional or stuffer polynucleotide;

iv) a second hairpin ribozyme cleavage site in the antisense orientation;

v) a hairpin ribozyme catalytic core in the antisense orientation;

vi) reverse and forward primer annealing sites in the antisense orientation; and vii) an inserted polynucleotide suspected of comprising a RNA promoter.

Embodiments of the hammerhead ribozyme catalytic core, the hairpin ribozyme cleavage sites, the non-functional or stuffer polynucleotide, the hairpin ribozyme catalytic core, the reverse and forward primer annealing sites and inserted polynucleotide suspected of comprising a RNA promoter are as described above for the DNA constructs. In addition, the RNA constructs comprise an hydroxyl group at the 5'-end and a 2':3' cyclic phosphodiester at the 3'-end in order to get cyclization of the RNA inside a host cell.

3. Plasmids and Viral Replicating Vectors

Further provided are DNA plasmids and viral replicating vectors comprising the DNA constructs described above and herein. In varying embodiments, the entire size of the DNA plasmids that are designed for screening and identifying functional RNA promoter sequences is from about 3000 bp to about 15,000 bp. Generally, the plasmid backbone comprises an origin of replication and an expression cassette for expressing a selection gene. In varying embodiments, the expression cassette for expressing a selection gene is in the antisense orientation from the 5' hammerhead ribozyme catalytic core. The selection gene can be any marker known in the art for selection of a host cell that has been transformed with a desired plasmid. In varying embodiments, the selection marker comprises a polynucleotide encoding a gene or protein conferring antibiotic resistance, heat tolerance, fluorescence, or luminescence.

Viral replicating vectors can be used to express the DNA or RNA constructs as described. Due to the presence of ribozymes in both strands of the RNA constructs, RNA virus vectors can be used by implementing adjustments to the RNA constructs. In planta, geminiviruses are a representative DNA virus that can be used as an expression system. Reviewed in, e.g., Hefferon, *Vaccines* (2014) 2:642-53. In animal cells, there are more choices. Plasmid expression constructs containing viral origins of replication, while not truly viral replicating systems, are stably maintained in cells. Truly replicating viral systems of use include without limitation, e.g., adenovirus, adeno-associated virus, baculovirus, and Vaccinia virus vectors, which are known in the art.

4. Host Cells

Further provided are host cells comprising the DNA or RNA constructs as described above and herein.

In varying embodiments, the host cell expresses a RNA dependent RNA polymerase. For example, in some embodiments, the host cell is transfected with a polynucleotide that encodes an exogenous RNA-dependent RNA polymerase. In some embodiments, the host cell is infected with a RNA virus. Illustrative RNA viruses include a virus of the taxonomic Orders Mononegavirales, Nidovirales, Picornavirales, and Tymovirales. Further illustrative RNA viruses include a virus of the taxonomic Groups arenaviridae, astroviridae, barnaviridae, benyviridae, bromoviridae, bunyaviridae, carmotetraviridae, closteroviridae, flaviviridae, hepeviridae, leviviridae, luteoviridae, narnaviridae, nodaviridae, ophioviridae, orthomyxoviridae, permutotetraviridae, potyviridae, togaviridae, tombusviridae, and virgaviridae. Further illustrative RNA viruses include a virus of the taxonomic Family celivirus, deltavirus, emaravirus, higrevirus, idaeovirus, ourmiavirus, polemovirus, sobemovirus, tenuivirus, umbravirus, or varicosavirus.

In varying embodiments, the host cell is a prokaryotic cell, e.g., a bacterial cell, an archaeal cell, or an archaebacterial cell. In varying embodiments, the host cell is a eukaryotic cell, e.g., an animal cell (e.g., a mammalian cell or an insect cell), a plant cell or a fungal cell.

Illustrative plant cells include without limitation, e.g., *Brassicaceae, Solanaceae, Phaseoleae, Zea* and Oryzeae.

5. Methods of Identifying RNA Promoters

Further provided are methods of identifying RNA Promoters. In the first instance, the methods employ one or more of the DNA or RNA constructs and one or more host cells, the embodiments of which are described above and herein.

In varying embodiments, the methods entail the following steps:
  a) transfecting a host cell with the DNA or RNA construct as described above and herein, wherein the 5' promoter is capable of promoting transcription in the host cell; wherein the host cell expresses a RNA-dependent RNA polymerase and rolling circle transcription of the RNA construct or RNA transcribed from the DNA construct within the host cell when the inserted polynucleotide comprises a functional RNA promoter yields a circularized RNA comprising:
    i) a hammerhead ribozyme catalytic core in the antisense orientation;
    ii) a hairpin ribozyme cleavage site;
    iii) a hairpin ribozyme catalytic core;
    iv) reverse and forward primer annealing sites; and
    v) the inserted polynucleotide comprising a functional RNA promoter;
  b) isolating the circularized RNA;
  c) amplifying the inserted polynucleotide comprising a functional RNA promoter; and
  d) sequencing the inserted polynucleotide comprising a functional RNA promoter, thereby identifying the RNA promoter.

In varying embodiments, the methods entail the following steps:
  a) transcribing in vitro into RNA the DNA construct as described above and herein, thereby producing a RNA transcript of the DNA construct;
  b) transfecting a host cell with the RNA transcript, wherein the host cell expresses a RNA-dependent RNA polymerase and rolling circle transcription of the RNA construct within the host cell when the inserted polynucleotide comprises a functional RNA promoter yields a circularized RNA comprising:
    i) a hammerhead ribozyme catalytic core in the antisense orientation;
    ii) a ribozyme cleavage site;
    iii) a hairpin ribozyme catalytic core;
    iv) reverse and forward primer annealing sites; and
    v) the inserted polynucleotide comprising a functional RNA promoter;
  c) isolating the circularized RNA;
  d) amplifying the inserted polynucleotide comprising a functional RNA promoter; and
  e) sequencing the inserted polynucleotide comprising a functional RNA promoter, thereby identifying the RNA promoter.

a. Transcribing In Vitro into RNA the DNA Construct

In varying embodiments, the one or more DNA constructs, as described above and herein, are first transcribed in vitro into RNA and then the RNA transcript is transfected into a host cell. The step of transcribing the one or more DNA constructs into RNA in vitro can be performed using any methodologies known in the art. In vitro transcription of one or more (e.g., a population of) DNA constructs comprising a library of inserts suspected of comprising a functional RNA promoter sequence can be achieved using purified RNA polymerases, e.g. T7 RNA polymerase. Such methodologies are described, e.g., in Green and Sambrook, Molecular Cloning, A Laboratory Manual, 4th Ed., Cold Spring Harbor Press, (2012). A schematic of the starting material DNA construct is depicted in FIG. 4A. The transcribed RNA construct is depicted in FIG. 4B. Cleavage will take place producing the RNA depicted in FIG. 4C. The in vitro transcribed and cleaved RNA construct remains linear.

b. Transfecting a Host Cell with the DNA or RNA Construct

In varying embodiments, the DNA construct or in vitro transcribed RNA construct is transfected into a suitable host cell of closed circular DNA plasmid using any method known in the art, e.g., by electroporation of protoplasts, fusion of liposomes to cell membranes, cell transfection methods using calcium ions or PEG, use of gold or tungsten microparticles coated with plasmid with the gene gun. Such methodologies are described, e.g., in Green and Sambrook, Molecular Cloning, A Laboratory Manual, 4th Ed., Cold Spring Harbor Press, (2012). As discussed above, the cells of all eukaryotic organisms (plants, animals, fungi, etc.) can be used. In varying embodiments, the host cell is a prokaryotic cell, e.g., a bacterial cell, an archaeal cell, or an archaebacterial cell.

In vitro produced linear molecules are circularized by introduction into cells. Production of the circular RNA or introduction of the linear RNA followed by circularization occurs in a host cell that expresses a RNA dependent RNA promoter. In varying embodiments, the host cell is infected with a RNA virus, as described above. In this way, viral replication machinery is already present within the transfected host cells. In most cases, the insert sequences suspected of comprising a RNA promoter (e.g., within the left terminal loop) do not contain a sequence that can interact with the viral replication machinery so no complementary RNA is generated. In some cases, the viral replication machinery will interact with the insert sequence suspected of comprising a RNA promoter and complementary sequences will be generated as shown in FIG. 5. Constructs having inserts that actually contain a RNA promoter construct undergo rolling circle replication. The mini-monomer cassette polynucleotide subsequences containing the hairpin ribozyme catalytic core, the insert containing a RNA promoter and the RT-PCR primer annealing sites are cleaved by the hairpin ribozyme catalytic core and circularize. Processing of this newly synthesized primary transcript is shown in FIG. 6. In contrast, the newly synthesized stuffier-containing fragments are not circularized because they do not contain a hairpin ribozyme catalytic core. Further the stuffer-containing fragments do not contain the primer binding sites and so are not recovered after RT-PCR.

c. Isolating the Circularized RNA

The step of isolating the circularized RNA molecules can be performed using any methodologies known in the art. Such methodologies are described, e.g., in Green and Sambrook, Molecular Cloning, A Laboratory Manual, 4th Ed., Cold Spring Harbor Press, (2012).

d. Amplifying the Inserted Polynucleotide Comprising a Functional RNA Promoter

The inserts containing a RNA promoter sequence in the circularized RNA molecules are amplified by RT-PCR, usually from the forward and reverse RT-PCR primer annealing polynucleotides. The step of reverse-transcribing the inserts containing a RNA promoter sequence in the circularized RNA molecules into cDNA can be performed using any methodologies known in the art. Such methodologies are described, e.g., in Green and Sambrook, Molecular Cloning, A Laboratory Manual, 4th Ed., Cold Spring Harbor Press, (2012).

cDNA can be synthesized from reverse transcription of the RNA of circularized and self-cleaved mini-monomer carrying a functional promoter (e.g., eukaryotic or prokaryotic) using a primer that binds at the reverse RT-PCR primer annealing sequence. Reverse transcription can be followed by PCR with the forward and reverse primers, thereby yielding a PCR product containing the mini-monomer sequence with the RNA promoter-containing insert if the RNA template for reverse transcription is circular. Because production and processing of the circularized RNA molecules requires initiation of transcription from a RNA promoter in the original linear construct, RT-PCR-derived cDNAs can only be produced if a cloned DNA insert contains a functional RNA promoter.

e. Sequencing the Inserted Polynucleotide Comprising a Functional RNA Promoter

The step of sequencing the inserted polynucleotides comprising a functional RNA promoter in the DNA polynucleotides amplified from the isolated circularized RNA can be performed using any methodologies known in the art. Such methodologies are described, e.g., in Green and Sambrook, Molecular Cloning, A Laboratory Manual, 4th Ed., Cold Spring Harbor Press, (2012). In varying embodiments, next generation sequencing, deep sequencing or ultra deep sequencing methodologies are applied. Deep sequencing data analysis is described, e.g., in "Deep Sequencing Data Analysis (Methods in Molecular Biology)," Noam Shomron (Editor), Humana Press; 2013 edition. Next generation sequencing is described, e.g., in "Next-Generation DNA Sequencing Informatics," Stuart M. Brown (Editor), Cold Spring Harbor Laboratory Press; 1st edition (2013); and "Next-generation Sequencing: Current Technologies and Applications," Jianping Xu (Editor), Caister Academic Press (2014); Wilhelm, et al., *Nature*. (2008) 453:1239-1243; Nagalakshmi, et al., *Science*. (2008) 320:1344-1349; and Mortazavi, et al., *Nat. Methods*. (2008) 5:621-628.

f. Exposure to External Influences

In varying embodiments, de novo selection and subsequent evolution of externally influenced RNA promoter sequences is performed. Using a library containing inserted polynucleotides suspected of comprising a RNA promoter sequence, as described above, insertion of this library into cells with or without some external factor $Ca^{++}$ ions, salt, temperature stress, hormones, etc.), followed by analysis as described previously will allow detection of sequences that are increased preferentially in the presence of the external factor. Analysis of these sequences allows determination of common features that can make the significant structural features more obvious. Reconstruction of a library of mutagenized sequences related to these initial sequences followed by reanalysis, again in the presence or absence of the external factor, will allow an evolutionary optimization of said RNA promoter sequences, ultimately leading to the selection of a de novo optimized RNA promoter sequence that can be used in the construction of novel promoters or modified genes that are responsive to the external factor in question.

g. Methods of Identifying Modifying RNA Promoter Sequences

The methods described herein can be used to identify functional RNA promoter sequences derived from known RNA promoter sequences, but having increased or decreased RNA transcriptional efficiencies or strengths. In varying embodiments, the insert suspected of comprising a RNA promoter sequence comprises a known RNA promoter sequence that has been mutated or mutagenized. The methods of RNA promoter sequence identification described above and herein allow one to take a known RNA promoter sequence, mutagenize it, then run the mutagenized sequences through the RNA promoter sequences selection procedure, thereby generating a quasispecies of new RNA promoter sequences with a range of RNA promoter sequences strengths (ability to increase or decrease RNA transcriptional efficiencies or strengths). This procedure can be done iteratively or generationally (e.g., providing a population of polynucleotides comprising mutagenized promoters, selecting for RNA promoter sequences having increased or decreased transcription efficiency (as desired), recovering RT-PCR products, performing one or more further rounds of mutagenesis and then performing the steps of the methods again, as many iterations as necessary or desired).

6. Kits

Further provided are kits containing one or more of the DNA and/or RNA constructs described herein. In varying embodiments, the kits can further comprise in one or more containers or vessels buffers, reagents, nucleotides, enzymes, control polynucleotides, host cells as described herein, and instructions for use. In varying embodiments, the kits comprise a library of DNA and/or RNA constructs for use in screening for RNA promoters, wherein each member of the library is pre-loaded with an inserted polynucleotide suspected of comprising a RNA promoter.

EXAMPLES

The following examples are offered to illustrate, but not to limit the claimed invention.

Example 1

Selection of an RNA Promoter from a Randomized DNA Library

This example illustrates the selection of a RNA promoter from a library of randomized DNA.

Two oligonucleotides are synthesized—one oligonucleotide containing a restriction endonuclease cleavage site, 50 N residues, where N can be any nucleotide, a specific sequence 3' to the 50 N residues and a second restriction endonuclease cleavage sites and a second oligonucleotide containing the complement of the specific sequence and second restriction endonuclease cleavage site. The two oligonucleotides are hybridized, made double stranded and cloned into a plasmid forming a construct of as shown in FIG. 4A using methods known to someone skilled in the art. If in vitro production of the RNA is to be performed, the plasmid may contain a T7 or other bacteriophage RNA polymerase promoter. If in vivo production of the RNA is to be performed, the plasmid can contain an appropriate promoter as well as any other necessary sequences appropriate for the in vivo environment being used, e.g. Left and Right T-DNA borders for *Agrobacterium*-mediated transient expression in plant cells.

In vitro produced RNA is purified, e.g., using phenol/chloroform/iso-amyl alcohol extraction and ethanol precipitation. The in vitro produced RNA may be introduced into cells already infected with the RNA virus for which the RNA promoter is being sought. If in vivo production is done, a construct using a eukaryotic promoter appropriate for a particular cell or organism type may be used. Alternatively, intracellular production of the viral RNA dependent RNA polymerase in the cells may be done. At various times after introduction, e.g. at 12 hours, 24 hours, 48 hours and 72 hours, total RNA are extracted from the cells into which the in vitro produced RNAs were introduced, e.g., using such methods as a Trizol reagent protocol or a commercial RNA extraction kit. This RNA is used directly for further steps. Alternatively, any circular RNAs is purified, e.g., using 2-D polyacrylamide gel electrophoresis. Complementary DNA (cDNA) is synthesized, e.g., by hybridizing an oligonucleotide to the RNA followed by reverse transcription, e.g., using an enzyme such as SuperScript II or Superscript III. PCR is performed to amplify any synthesized cDNA using a set of oligonucleotide primers that only amplifies the complementary RNA that was circularized by hairpin ribozyme ligation. To ensure that any newly synthesized complementary RNA is generated by the virus replication machinery, a control experiment can be performed in uninfected cells. Sequencing of the amplified cDNA sequences from both virus-infected and uninfected cells followed by a comparison of any sequences recovered from said cells identifies those sequences that are uniquely present in the virus-infect cells. These unique sequences can be recognized by the viral RNA dependent RNA polymerase.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

| INFORMAL SEQUENCE LISTING |  |
|---|---|
| Sequence ID No: 1 - mini-monomer cassette sequence for RNA promoter selection Annotation: | |
| Hammerhead ribozyme region | 8-55 |
| D8 complement | 51-58 |
| P5 complement | 59-63 |
| Stuffer insertion site | 93-98 |
| 2nd D8 complement | 99-106 |
| 2nd P5 complement | 107-111 |
| Hairpin catalytic core complement | 126-172 |
| Multiple cloning site | 221-315 |
| RT primer 1 complement | 281-301 |
| Primer 2 complement | 255-280 |
| HDV negative strand ribozyme | 326-413 |

| INFORMAL SEQUENCE LISTING |
|---|
| ATACCCTGTCACCGGATGTGCTTTCCGGTCTGATGAGTCCGTGAGGACGAAACAGGACTGT |
| CAGGTGGCCGAAAGCCACCACGTAAACTAGTGGATCCAACAGGACTGTCAGCTAGTCAAGG |
| CGTACCAGGTAATATACCACAACGTGTGTTTCTCTGGTTGACTTCTCTGTTTGTTGTGTCA |
| TTGGTTCCCGGATCTCGCATTAGCGGCGACGGGGTATCCTGCAGGAAGCTTGGATCCGTCG |
| ACGCGGCCGCGATCGTCGGACTGTAGAACTCTGAACCCTTGGCACCCGAGAATTCCAGAAT |
| TCGGCGCGCCATACCCTGTCGGGTCGGCATGGCATCTCCACCTCCTCGCGGTCCGACCTGG |
| GCATCCGAAGGAGGACAGACGTCCACTCGGATGGCTAAGGGAGAGCC |

Sequence ID No: 2 - intentionally left blank

Sequence ID No: 3 - negative strand self-cleavage domain of the satellite RNA of tobacco ringspot virus (sTRSV)
GACAGAGAAGTCAACCAGAGAAACACACGTTGTGGTATATTACCTGGT Sequence ID No: 4 - negative strand self-cleavage domain of the satellite RNA of arabis mosaic virus (sArMV)
GACAGCGAAGTCAAACGGCGAAACACACCTTGTGTGGTATATTACCCGTT Sequence ID No: 5 - negative strand self-cleavage domain of the satellite RNA of the satellite RNA of chicory yellow mottle virus (sCYMV)
GACAGCGAAGTCAGCCAGGGAAACACACCATGTGTGGTATATTATCTGGC Sequence ID No: 6 - ribozyme cleavage site
TGACCGTCCTGTC Sequence ID No: 7 - Generalized ribozyme cleavage site
$N_{S1}N_{S2}N_{S3}N_{S4}$NGUCN$_{S5}N_{S6}N_{S7}N_{S8}N_{S9}$
Wherein N = Any nucleotide (For RNA, A, C, G or U)

Sequence ID No: 8 - Generalized negative strand self-cleavage domain
$N_{E9}N_{E8}N_{E7}N_{E6}N_{E5}$(A/C)GAAN$_{E4}N_{E3}N_{E2}N_{E1}N_{E10}N_{E11}N_{E12}N_{E13}N_{E14}$AGAAACAN$_{E20}N_{E21}N_{E22}$
$N_{L6}N_{L7}N_{L8}N_{L9}N_{L10}N_{E22'}N_{E21'}N_{E20'}$GUAUAUUACN$_{E14'}N_{E13'}N_{E12'}N_{E11'}N_{E10'}$
Wherein N = Any nucleotide (For RNA, A, C, G or U)

Interactions between the generalized ribozyme cleavage site (SEQ ID NO: 7) and the generalized negative strand self-cleavage domain (SEQ ID NO: 8) are via hydrogen bonds forming two stems-1 and 2

Stem 1 is formed by hydrogen bonds between $N_{S1}$ and $N_{E1}$, $N_{S2}$ and $N_{E2}$, $N_{S3}$ and $N_{E3}$, $N_{S4}$ and $N_{E4}$.

Stem 2 is formed by hydrogen bonds between $N_{S5}$ and $N_{E5}$, $N_{S6}$ and $N_{E6}$, $N_{S7}$ and $N_{E7}$, $N_{S8}$ and $N_{E8}$, $N_{S9}$ and $N_{E9}$.

Interactions within the generalized negative strand self-cleavage domain form 2 stems-3 and 4.

Stem 3 is formed by hydrogen bonds between $N_{E10}$ and $N_{E10'}$, $N_{E11}$ and $N_{E11'}$, $N_{E12}$ and $N_{E12'}$, $N_{E13}$ and $N_{E13'}$, $N_{E14}$ and $N_{E14'}$.

Stem 4 is formed by hydrogen bonds between $N_{E20}$ and $N_{E20'}$, $N_{E21}$ and $N_{E21'}$, and $N_{E22}$ and $N_{E22'}$.

Stem 1 is essentially universally 4 base pairs long
Stem 2 can be as short as 4 base pairs, but can be longer
Stem 3 is essentially universally 5 base pairs long
Stem 4 is from 2 to 4 base pairs long depending on the source Loop 1 can be as small as 4 nucleotides, if it is a special sequence called a tetra-loop, but can be longer, e.g., 100's of nucleotides up to 1000 nucleotides
Loop 2 varies from 4 to 6 bases long in natural sequences -continued

INFORMAL SEQUENCE LISTING

SEQ ID NO: 9 - In vitro production construct for MiniM
cassette production for RNA promoter selection
Features List

| Name | location |
|---|---|
| T7 RNA promoter | 6..23 |
| Hammerhead ribozyme region | 38..85 |
| D8 complement | 81..88 |
| P5 complement | 89..93 |
| Stuffer insertion site | 123..128 |
| 2nd D8 complement | 129..136 |
| 2nd P5 complement | 137..141 |
| Hairpin catalytic core complement | 156..202 |
| Multiple cloning site | 252..345 |
| Primer 2 complement | 285..310 |
| RT primer 1 complement | 311..330 |
| HDV negative strand ribozyme | 357..442 |
| seq1 | 2092..2121 |
| seq2 | rev: 502..525 |
| rep (pMB1) | rev: 451..1065 |
| ampR | rev: 1225..2085 |
| ampr promoter | rev: 2086..2190 |

AGATCTAATAGCACTCACTATAGGGGATCTATACCCTGTCACCGGATGTGCTTTCCGGTCT

GATGAGTCCGTGAGGACGAAACAGGACTGTCAGGTGGCCGAAAGCCACCACGTAAACTAGT

GGATCCAACAGGACTGTCAGCTAGTCAAGGCGTACCAGGTAATATACCACAACGTGTGTTT

CTCTGGTTGACTTCTCTGTTTGTTGTGTCATTGGTTCCCGGATCTCGCATTAGCGGCGACG

GGGTATCCTGCAGGAAGCTTGGATCCGTCGACGCGGCCGCGATCGTCGGACTGTAGAACTC

TGAACCCTTGGCACCCGAGAATTCCAGAATTCGGCGCGCCATACCCTGTCGGGTCGGCATG

GCATCTCCACCTCCTCGCGGTCCGACCTGGGCATCCGAAGGAGGACAGACGTCCACTCGGA

TGGCTAAGGGAGAGCCATCTAGACGCGTTGCTGGCGTTTTTCCATAGGCTCCGCCCCCCTG

ACGAGCATCACAAAAATCGACGCTCAAGTCAGAGGTGGCGAAACCCGACAGGACTATAAAG

ATACCAGGCGTTTCCCCCTGGAAGCTCCCTCGTGCGCTCTCCTGTTCCGACCCTGCCGCTT

ACCGGATACCTGTCCGCCTTTCTCCCTTCGGGAAGCGTGGCGCTTTCTCATAGCTCACGCT

GTAGGTATCTCAGTTCGGTGTAGGTCGTTCGCTCCAAGCTGGGCTGTGTGCACGAACCCCC

CGTTCAGCCCGACCGCTGCGCCTTATCCGGTAACTATCGTCTTGAGTCCAACCCGGTAAGA

CACGACTTATCGCCACTGGCAGCAGCCACTGGTAACAGGATTAGCAGAGCGAGGTATGTAG

GCGGTGCTACAGAGTTCTTGAAGTGGTGGCCTAACTACGGCTACACTAGAAGAACAGTATT

TGGTATCTGCGCTCTGCTGAAGCCAGTTACCTTCGGAAAAAGAGTTGGTAGCTCTTGATCC

GGCAAACAAACCACCGCTGGTAGCGGTGGTTTTTTTGTTTGCAAGCAGCAGATTACGCGCA

GAAAAAAGGATCTCAAGAAGATCCTTTGATCTTTTCTACGGGGTCTGACGCTCAGTGGAA

CGAAAACTCACGTTAAGGGATTTTGGTCATGAGATTATCAAAAAGGATCTTCACCTAGATC

| INFORMAL SEQUENCE LISTING |
|---|
| CTTTTAAATTAAAAATGAAGTTTTAAATCAATCTAAAGTATATATGAGTAAACTTGGTCTG |
| ACAGTTACCAATGCTTAATCAGTGAGGCACCTATCTCAGCGATCTGTCTATTTCGTTCATC |
| CATAGTTGCCTGACTCCCCGTCGTGTAGATAACTACGATACGGGAGGGCTTACCATCTGGC |
| CCCAGTGCTGCAATGATACCGCGAGACCCACGCTCACCGGCTCCAGATTTATCAGCAATAA |
| ACCAGCCAGCCGGAAGGGCCGAGCGCAGAAGTGGTCCTGCAACTTTATCCGCCTCCATCCA |
| GTCTATTAATTGTTGCCGGGAAGCTAGAGTAAGTAGTTCGCCAGTTAATAGTTTGCGCAAC |
| GTTGTTGCCATTGCTACAGGCATCGTGGTGTCACGCTCGTCGTTTGGTATGGCTTCATTCA |
| GCTCCGGTTCCCAACGATCAAGGCGAGTTACATGATCCCCCATGTTGTGCAAAAAAGCGGT |
| TAGCTCCTTCGGTCCTCCGATCGTTGTCAGAAGTAAGTTGGCCGCAGTGTTATCACTCATG |
| GTTATGGCAGCACTGCATAATTCTCTTACTGTCATGCCATCCGTAAGATGCTTTTCTGTGA |
| CTGGTGAGTACTCAACCAAGTCATTCTGAGAATAGTGTATGCGGCGACCGAGTTGCTCTTG |
| CCCGGCGTCAATACGGGATAATACCGCGCCACATAGCAGAACTTTAAAAGTGCTCATCATT |
| GGAAAACGTTCTTCGGGGCGAAAACTCTCAAGGATCTTACCGCTGTTGAGATCCAGTTCGA |
| TGTAACCCACTCGTGCACCCAACTGATCTTCAGCATCTTTTACTTTCACCAGCGTTTCTGG |
| GTGAGCAAAAACAGGAAGGCAAAATGCCGCAAAAAAGGGAATAAGGGCGACACGGAAATGT |
| TGAATACTCATACTCTTCCTTTTTCAATATTATTGAAGCATTTATCAGGGTTATTGTCTCA |
| TGAGCGGATACATATTTGAATGTATTTAGAAAAATAAACAAATAGGGGTTCCGCG |

| SEQ ID NO: 10 - In planta production construct for MiniM cassette production for RNA promoter selection Features List |||
|---|---|
| Name | location |
| Right border | 1..161 |
| CaMV 35S promoter | 470..782 |
| Hammerhead ribozyme region | 793..840 |
| D8 complement | 836..843 |
| P5 complement | 844..848 |
| Stuffer insertion site | 878..883 |
| 2nd D8 complement | 884..891 |
| 2nd P5 complement | 892..896 |
| Hairpin catalytic core complement | 911..957 |
| Multiple cloning site | 1007..1100 |
| Primer 2 complement | 1040..1065 |
| RT primer 1 complement | 1066..1085 |
| HDV negative strand ribozyme | 1112..1197 |
| CaMV 35S terminator | 1200..1897 |
| neomycin phosphotransferase II | 2235..3029 |
| ColE1 on from pBR322 | 7644..8231 |
| Left border | rev: 3711..3857 |
| OriV from pRK2 | rev: 4164..4779 |

| INFORMAL SEQUENCE LISTING | |
|---|---|
| trfA | rev: 4878..6026 |
| neomycin phosphotransferase III | rev: 6325..7119 |

CCTGTGGTTGGCATGCACATACAAATGGACGAACGGATAAACCTTTTCACGCCCTTTTAAATATCCG

ATTATTCTAATAAACGCTCTTTTCTCTTAGGTTTACCCGCCAATATATCCTGTCAAACACTGATAGT

TTGTGAACCATCACCCAAATCAAGTTTTTTGGGGTCGAGGTGCCGTAAAGCACTAAATCGGAACCCT

AAAGGGAGCCCCCGATTTAGAGCTTGACGGGGAAAGCCGGCGAACGTGGCGAGAAAGGAAGGGAAGA

AAGCGAAAGGAGCGGGCGCCATTCAGGCTGCGCAACTGTTGGGAAGGGCGATCGGTGCGGGCCTCTT

CGCTATTACGCCAGCTGGCGAAAGGGGATGTGCTGCAAGGCGATTAAGTTGGGTAACGCCAGGGTT

TTCCCAGTCACGACGTTGTAAAACGACGGCCAGTGAATTGTTAATTAAGAATTCGAGCTCCACCGCG

GAAACCTCCTCGGATTCCATTGCCCAGCTATCTGTCACTTTATTGAGAAGATAGTGGAAAAGGAAGG

TGGCTCCTACAAATGCCATCATTGCGATAAAGGAAAGGCCATCGTTGAAGATGCCTCTGCCGACAGT

GGTCCCAAAGATGGACCCCCACCCACGAGGAGCATCGTGGAAAAAGAAGACGTTCCAACCACGTCTT

CAAAGCAAGTGGATTGATGTGATATCTCCACTGACGTAAGGGATGACGCACAATCCCACTATCCTTC

GCAAGACCCTTCCTCTATATAAGGAAGTTCATTTCATTTGGAGAGGGTATACCCTGTCACCGGATGT

GCTTTCCGGTCTGATGAGTCCGTGAGGACGAAACAGGACTGTCAGGTGGCCGAAAGCCACCACGTAA

ACTAGTGGATCCAACAGGACTGTCAGCTAGTCAAGGCGTACCAGGTAATATACCACAACGTGTGTTT

CTCTGGTTGACTTCTCTGTTTGTTGTGTCATTGGTTCCCGGATCTCGCATTAGCGGCGACGGGGTAT

CCTGCAGGAAGCTTGGATCCGTCGACGCGGCCGCGATCGTCGGACTGTAGAACTCTGAACCCTTGGC

ACCCGAGAATTCCAGAATTCGGCGCGCCATACCCTGTCGGGTCGGCATGGCATCTCCACCTCCTCGC

GGTCCGACCTGGGCATCCGAAGGAGGACAGACGTCCACTCGGATGGCTAAGGGAGAGCCATCGAATT

CGCTGAAATCACCAGTCTCTCTCTACAAATCTATCTCTCTATTTTCTCCATAAATAATGTGTGAG

TAGTTTCCCGATAAGGGAAATTAGGGTTCTTATAGGGTTTCGCTCATGTGTTGAGCATATAAGAAAC

CCTTAGTATGTATTTGTATTTGTAAAATACTTCTATCAATAAAATTTCTAATTCCTAAAACCAAAAT

CCAGTACTAAAATCCAGATCTCCTAAAGTCCCTATAGATCTTTGTCGTGAATATAAACCAGACACGA

GACGACTAAACCTGGAGCCCAGACGCCGTTCGAAGCTAGAAGTACCGCTTAGGCAGGAGGCCGTTAG

GGAAAAGATGCTAAGGCAGGGTTGGTTACGTTGACTCCCCCGTAGGTTTGGTTTAAATATGATGAAG

TGGACGGAAGGAAGGAGGAAGACAAGGAAGGATAAGGTTGCAGGCCCTGTGCAAGGTAAGAAGATGG

AAATTTGATAGAGGTACGCTACTATACTTATACTATACGCTAAGGGAATGCTTGTATTTATACCCTA

TACCCCCTAATAACCCCTTATCAATTTAAGAAATAATCCGCATAAGCCCCGCTTAAAAATTGGTAT

CAGAGCCATGAATAGGTCTATGACCAAAACTCAAGAGGATAAAACCTCACCAAAATACGAAAGAGTT

CTTAACTCTAAAGATAAAAGATGGCGCGTGGCCGGCCTACAGTATGAGCGGAGAATTAAGGGAGTCA

CGTTATGACCCCCGCCGATGACGCGGGACAAGCCGTTTTACGTTTGGAACTGACAGAACCGCAACGT

TGAAGGAGCCACTCAGCCGCGGGTTTCTGGAGTTTAATGAGCTAAGCACATACGTCAGAAACCATTA

TTGCGCGTTCAAAAGTCGCCTAAGGTCACTATCAGCTAGCAAATATTTCTTGTCAAAAATGCTCCAC

TGACGTTCCATAAATTCCCCTCGGTATCCAATTAGAGTCTCATATTCACTCTCAATCCAAATAATCT

GCACCGGATCTGGATCGTTTCGCATGATTGAACAAGATGGATTGCACGCAGGTTCTCCGGCCGCTTG

GGTGGAGAGGCTATTCGGCTATGACTGGGCACAACAGACAATCGGCTGCTCTGATGCCGCCGTGTTC

CGGCTGTCAGCGCAGGGGCGCCCGGTTCTTTTTGTCAAGACCGACCTGTCCGGTGCCCTGAATGAAC

TGCAGGACGAGGCAGCGCGGCTATCGTGGCTGGCCACGACGGGCGTTCCTTGCGCAGCTGTGCTCGA

INFORMAL SEQUENCE LISTING

CGTTGTCACTGAAGCGGGAAGGGACTGGCTGCTATTGGGCGAAGTGCCGGGGCAGGATCTCCTGTCA

TCTCACCTTGCTCCTGCCGAGAAAGTATCCATCATGGCTGATGCAATGCGGCGGCTGCATACGCTTG

ATCCGGCTACCTGCCCATTCGACCACCAAGCGAAACATCGCATCGAGCGAGCACGTACTCGGATGGA

AGCCGGTCTTGTCGATCAGGATGATCTGGACGAAGAGCATCAGGGGCTCGCGCCAGCCGAACTGTTC

GCCAGGCTCAAGGCGCGCATGCCCGACGGCGATGATCTCGTCGTGACCCATGGCGATGCCTGCTTGC

CGAATATCATGGTGGAAAATGGCCGCTTTTCTGGATTCATCGACTGTGGCCGGCTGGGTGTGGCGGA

CCGCTATCAGGACATAGCGTTGGCTACCCGTGATATTGCTGAAGAGCTTGGCGGCGAATGGGCTGAC

CGCTTCCTCGTGCTTTACGGTATCGCCGCTCCCGATTCGCAGCGCATCGCCTTCTATCGCCTTCTTG

ACGAGTTCTTCTGAGCGGGACTCTGGGGTTCGAAATGACCGACCAAGCGACGCCCAACCTGCCATCA

CGAGATTTCGATTCCACCGCCGCCTTCTATGAAAGGTTGGGCTTCGGAATCGTTTTCCGGGACGCCG

GCTGGATGATCCTCCAGCGCGGGGATCTCATGCTGGAGTTCTTCGCCCACGGGATCTCTGCGGAACA

GGCGGTCGAAGGTGCCGATATCATTACGACAGCAACGGCCGACAAGCACAACGCCACGATCCTGAGC

GACAATATGATCGCGGCGTCCACATCAACGGCGTCGGCGGCGACTGCCCAGGCAAGACCGAGATGCA

CCGCGATATCTTGCTGCGTTCGGATATTTTCGTGGAGTTCCCGCCACAGACCCGGATGATCCCCGAT

CGTTCAAACATTTGGCAATAAAGTTTCTTAAGATTGAATCCTGTTGCCGGTCTTGCGATGATTATCA

TATAATTTCTGTTGAATTACGTTAAGCATGTAATAATTAACATGTAATGCATGACGTTATTTATGAG

ATGGGTTTTATGATTAGAGTCCCGCAATTATACATTTAATACGCGATAGAAAACAAAATATAGCGC

GCAAACTAGGATAAATTATCGCGCGCGGTGTCATCTATGTTACTAGATCGGGACTGTAGGCCGGCCC

TCACTGGTGAAAAGAAAAACCACCCCAGTACATTAAAAACGTCCGCAATGTGTTATTAAGTTGTCTA

AGCGTCAATTTGTTTACACCACAATATATCCTGCCACCAGCCAGCCAACAGCTCCCCGACCGGCAGC

TCGGCACAAAATCACCACTCGATACAGGCAGCCCATCAGTCCGGGACGGCGTCAGCGGGAGAGCCGT

TGTAAGGCGGCAGACTTTGCTCATGTTACCGATGCTATTCGGAAGAACGGCAACTAAGCTGCCGGGT

TTGAAACACGGATGATCTCGCGGAGGGTAGCATGTTGATTGTAACGATGACAGAGCGTTGCTGCCTG

TGATCAAATATCATCTCCCTCGCACAGATCCGAATTATCAGCCTTCTTATTCATTTCTCGCTTAACC

GTGACAGAGTAGACAGGCTGTCTCGCGGCCGAGGGGCGCAGCCCCTGGGGGGATGGGAGGCCCGCG

TTAGCGGGCCGGGAGGGTTCGAGAAGGGGGGGCACCCCCCTTCGGCGTGCGCGGTCACGCGCACAGG

GCGCAGCCCTGGTTAAAAACAAGGTTTATAAATATTGGTTTAAAAGCAGGTTAAAAGACAGGTTAGC

GGTGGCCGAAAAACGGGCGGAAACCCTTGCAAATGCTGGATTTTCTGCCTGTGGACAGCCCCTCAAA

TGTCAATAGGTGCGCCCCTCATCTGTCAGCACTCTGCCCCTCAAGTGTCAAGGATCGCGCCCCTCAT

CTGTCAGTAGTCGCGCCCCTCAAGTGTCAATACCGCAGGGCACTTATCCCCAGGCTTGTCCACATCA

TCTGTGGGAAACTCGCGTAAAATCAGGCGTTTTCGCCGATTTGCGAGGCTGGCCAGCTCCACGTCGC

CGGCCGAAATCGAGCCTGCCCCTCATCTGTCAACGCCGCGCCGGGTGAGTCGGCCCCTCAAGTGTCA

ACGTCCGCCCCTCATCTGTCAGTGAGGGCCAAGTTTTCCGCGAGGTATCCACAACGCCGGCGGCCGC

GGTGTCTCGCACACGGCTTCGACGGCGTTTCTGGCGCGTTTGCAGGGCCATAGACGGCCGCCAGCCC

AGCGGCGAGGGCAACCAGCCCGGTGAGCGTCGGAAAGGCGCTCGGTCTTGCCTTGCTCGTCGGTGAT

GTACACTAGTCGCTGGCTGCTGAACCCCCAGCCGGAACTGACCCCACAAGGCCCTAGCGTTTGCAAT

GCACCAGGTCATCATTGACCCAGGCGTGTTCCACCAGGCCGCTGCCTCGCAACTCTTCGCAGGCTTC

GCCGACCTGCTCGCGCCACTTCTTCACGCGGGTGGAATCCGATCCGCACATGAGGCGGAAGGTTTCC

INFORMAL SEQUENCE LISTING

```
AGCTTGAGCGGGTACGGCTCCCGGTGCGAGCTGAAATAGTCGAACATCCGTCGGGCCGTCGGCGACA
GCTTGCGGTACTTCTCCCATATGAATTTCGTGTAGTGGTCGCCAGCAAACAGCACGACGATTTCCTC
GTCGATCAGGACCTGGCAACGGGACGTTTTCTTGCCACGGTCCAGGACGCGGAAGCGGTGCAGCAGC
GACACCGATTCCAGGTGCCCAACGCGGTCGGACGTGAAGCCCATCGCCGTCGCCTGTAGGCGCGACA
GGCATTCCTCGGCCTTCGTGTAATACCGGCCATTGATCGACCAGCCCAGGTCCTGGCAAAGCTCGTA
GAACGTGAAGGTGATCGGCTCGCCGATAGGGGTGCGCTTCGCGTACTCCAACACCTGCTGCCACACC
AGTTCGTCATCGTCGGCCCGCAGCTCGACGCCGGTGTAGGTGATCTTCACGTCCTTGTTGACGTGGA
AAATGACCTTGTTTTGCAGCGCCTCGCGCGGGATTTTCTTGTTGCGCGTGGTGAACAGGGCAGAGCG
GGCCGTGTCGTTTGGCATCGCTCGCATCGTGTCCGGCCACGGCGCAATATCGAACAAGGAAAGCTGC
ATTTCCTTGATCTGCTGCTTCGTGTGTTTCAGCAACGCGGCCTGCTTGGCCTCGCTGACCTGTTTTG
CCAGGTCCTCGCCGGCGGTTTTTCGCTTCTTGGTCGTCATAGTTCCTCGCGTGTCGATGGTCATCGA
CTTCGCCAAACCTGCCGCCTCCTGTTCGAGACGACGCGAACGCTCCACGGCGGCCGATGGCGCGGGC
AGGGCAGGGGGAGCCAGTTGCACGCTGTCGCGCTCGATCTTGGCCGTAGCTTGCTGGACCATCGAGC
CGACGGACTGGAAGGTTTCGCGGGGCGCACGCATGACGGTGCGGCTTGCGATGGTTTCGGCATCCTC
GGCGGAAAACCCCGCGTCGATCAGTTCTTGCCTGTATGCCTTCCGGTCAAACGTCCGATTCATTCAC
CCTCCTTGCGGGATTGCCCCGACTCACGCCGGGGCAATGTGCCCTTATTCCTGATTTGACCCGCCTG
GTGCCTTGGTGTCCAGATAATCCACCTTATCGGCAATGAAGTCGGTCCCGTAGACCGTCTGGCCGTC
CTTCTCGTACTTGGTATTCCGAATCTTGCCCTGCACGAATACCAGCGACCCCTTGCCCAAATACTTG
CCGTGGGCCTCGGCCTGAGAGCCAAAACACTTGATGCGGAAGAAGTCGGTGCGCTCCTGCTTGTCGC
CGGCATCGTTGCGCCACATCTAGGTACTAAAACAATTCATCCAGTAAAATATAATATTTTATTTTCT
CCCAATCAGGCTTGATCCCCAGTAAGTCAAAAAATAGCTCGACATACTGTTCTTCCCCGATATCCTC
CCTGATCGACCGGACGCAGAAGGCAATGTCATACCACTTGTCCGCCCTGCCGCTTCTCCCAAGATCA
ATAAAGCCACTTACTTTGCCATCTTTCACAAAGATGTTGCTGTCTCCCAGGTCGCCGTGGGAAAAGA
CAAGTTCCTCTTCGGGCTTTTCCGTCTTTAAAAAATCATACAGCTCGCGCGGATCTTTAAATGGAGT
GTCTTCTTCCCAGTTTTCGCAATCCACATCGGCCAGATCGTTATTCAGTAAGTAATCCAATTCGGCT
AAGCGGCTGTCTAAGCTATTCGTATAGGGACAATCCGATATGTCGATGGAGTGAAAGAGCCTGATGC
ACTCCGCATACAGCTCGATAATCTTTTCAGGGCTTTGTTCATCTTCATACTCTTCCGAGCAAAGGAC
GCCATCGGCCTCACTCATGAGCAGATTGCTCCAGCCATCATGCCGTTCAAAGTGCAGGACCTTTGGA
ACAGGCAGCTTTCCTTCCAGCCATAGCATCATGTCCTTTTCCCGTTCCACATCATAGGTGGTCCCTT
TATACCGGCTGTCCGTCATTTTTAAATATAGGTTTTCATTTTCTCCCACCAGCTTATATACCTTAGC
AGGAGACATTCCTTCCGTATCTTTTACGCAGCGGTATTTTTCGATCAGTTTTTTCAATTCCGGTGAT
ATTCTCATTTTAGCCATTTATTATTTCCTTCCTCTTTTCTACAGTATTTAAAGATACCCCAAGAAGC
TAATTATAACAAGACGAACTCCAATTCACTGTTCCTTGCATTCTAAAACCTTAAATACCAGAAAACA
GCTTTTTCAAAGTTGTTTTCAAAGTTGGCGTATAACATAGTATCGACGGAGCCGATTTTGAAACCAC
AATTATGGGTGATGCTGCCAACTTACTGATTTAGTGTATGATGGTGTTTTTGAGGTGCTCCAGTGGC
TTCTGTTTCTATCAGCTGTCCCTCCTGTTCAGCTACTGACGGGGTGGTGCGTAACGGCAAAAGCACC
GCCGGACATCAGCGCTATCTCTGCTCTCACTGCCGTAAAACATGGCAACTGCAGTTCACTTACACCG
CTTCTCAACCCGGTACGCACCAGAAAATCATTGATATGGCCATGAATGGCGTTGGATGCCGGCAAC
AGCCCGCATTATGGGCGTTGGCCTCAACACGATTTTACGTCACTTAAAAAACTCAGGCCGCAGTCGG
```

TAACTATGCGGTGTGAAATACCGCACAGATGCGTAAGGAGAAAATACCGCATCAGGCGCTCTTCCGC

TTCCTCGCTCACTGACTCGCTGCGCTCGGTCGTTCGGCTGCGGCGAGCGGTATCAGCTCACTCAAAG

GCGGTAATACGGTTATCCACAGAATCAGGGGATAACGCAGGAAAGAACATGTGAGCAAAAGGCCAGC

AAAAGGCCAGGAACCGTAAAAAGGCCGCGTTGCTGGCGTTTTTCCATAGGCTCCGCCCCCCTGACGA

GCATCACAAAAATCGACGCTCAAGTCAGAGGTGGCGAAACCCGACAGGACTATAAAGATACCAGGCG

TTTCCCCCTGGAAGCTCCCTCGTGCGCTCTCCTGTTCCGACCCTGCCGCTTACCGGATACCTGTCCG

CCTTTCTCCCTTCGGGAAGCGTGGCGCTTTCTCATAGCTCACGCTGTAGGTATCTCAGTTCGGTGTA

GGTCGTTCGCTCCAAGCTGGGCTGTGTGCACGAACCCCCCGTTCAGCCCGACCGCTGCGCCTTATCC

GGTAACTATCGTCTTGAGTCCAACCCGGTAAGACACGACTTATCGCCACTGGCAGCAGGTAACCTCG

CGCATACAGCCGGGCAGTGACGTCATCGTCTGCGCGGAAATGGACGGGCCCCCGGCGCCAGATCTGG

GGAAC

| SEQ ID NO: 11 - Animal cell production construct for MiniM cassette production for RNA promoter selection Features List | |
|---|---|
| Name | location |
| CMV promoter | 15..754 |
| Hammerhead ribozyme region | 866..913 |
| D8 complement | 909..916 |
| P5 complement | 917..921 |
| Stuffer insertion site | 951..956 |
| 2nd D8 complement | 957..964 |
| 2nd P5 complement | 965..969 |
| Hairpin catalytic core complement | 984..1030 |
| Multiple cloning site | 1080..1173 |
| Primer 2 complement | 1113..1138 |
| RT primer 1 complement | 1139..1158 |
| HDV negative strand ribozyme | 1185..1270 |
| polyA signal sequence | 1313..1532 |
| SV40 early enhancer/promoter | 1582..1998 |
| hygR | 2024..3061 |
| ColE1 origin from pBR322 | 3274..3812 |
| polyA signal sequence | 5213..5260 |
| ampR | rev: 4248..5108 |

GGCCTAACTGGCCTCAATATTGGCCATTAGCCATATTATTCATTGGTTATATAGCATAAATCAATAT

TGGCTATTGGCCATTGCATACGTTGTATCTATATCATAATATGTACATTTATATTGGCTCATGTCCA

ATATGACCGCCATGTTGGCATTGATTATTGACTAGTTATTAATAGTAATCAATTACGGGGTCATTAG

TTCATAGCCCATATATGGAGTTCCGCGTTACATAACTTACGGTAAATGGCCCGCCTGGCTGACCGCC

CAACGACCCCCGCCCATTGACGTCAATAATGACGTATGTTCCCATAGTAACGCCAATAGGGACTTTC

CATTGACGTCAATGGGTGGAGTATTTACGGTAAACTGCCCACTTGGCAGTACATCAAGTGTATCATA

| INFORMAL SEQUENCE LISTING |
|---|
| TGCCAAGTCCGCCCCCTATTGACGTCAATGACGGTAAATGGCCCGCCTGGCATTATGCCCAGTACAT |
| GACCTTACGGGACTTTCCTACTTGGCAGTACATCTACGTATTAGTCATCGCTATTACCATGGTGATG |
| CGGTTTTGGCAGTACACCAATGGGCGTGGATAGCGGTTTGACTCACGGGGATTTCCAAGTCTCCACC |
| CCATTGACGTCAATGGGAGTTTGTTTTGGCACCAAAATCAACGGGACTTTCCAAAATGTCGTAATAA |
| CCCCGCCCCGTTGACGCAAATGGGCGGTAGGCGTGTACGGTGGGAGGTCTATATAAGCAGAGCTCGT |
| TTAGTGAACCGTCAGATCACTAGAAGCTTTATTGCGGTAGTTTATCACAGTTAAATTGCTAACGCAG |
| TCAGTGGGCCTCGGCGGCCAAGCTTGGCAATCCGGTACTGTTGGTAAAGCCACCATACCCTGTCACC |
| GGATGTGCTTTCCGGTCTGATGAGTCCGTGAGGACGAAACAGGACTGTCAGGTGGCCGAAAGCCACC |
| ACGTAAACTAGTGGATCCAACAGGACTGTCAGCTAGTCAAGGCGTACCAGGTAATATACCACAACGT |
| GTGTTTCTCTGGTTGACTTCTCTGTTTGTTGTGTCATTGGTTCCCGGATCTCGCATTAGCGGCGACG |
| GGGTATCCTGCAGGAAGCTTGGATCCGTCGACGCGGCCGCGATCGTCGGACTGTAGAACTCTGAACC |
| CTTGGCACCCGAGAATTCCAGAATTCGGCGCGCCATACCCTGTCGGGTCGGCATGGCATCTCCACCT |
| CCTCGCGGTCCGACCTGGGCATCCGAAGGAGGACAGACGTCCACTCGGATGGCTAAGGGAGAGCCAG |
| GCCGCGACTCTAGAGTCGGGGCGGCCGGCCGCTTCGAGCAGACATGATAAGATACATTGATGAGTTT |
| GGACAAACCACAACTAGAATGCAGTGAAAAAAATGCTTTATTTGTGAAATTTGTGATGCTATTGCTT |
| TATTTGTAACCATTATAAGCTGCAATAAACAAGTTAACAACAACAATTGCATTCATTTTATGTTTCA |
| GGTTCAGGGGGAGGTGTGGGAGGTTTTTTAAAGCAAGTAAAACCTCTACAAATGTGGTAAAATCGAT |
| AAGGATCCGTTTGCGTATTGGGCGCTCTTCCGCTGATCTGCGCAGCACCATGGCCTGAAATAACCTC |
| TGAAAGAGGAACTTGGTTAGCTACCTTCTGAGGCGGAAAGAACCAGCTGTGGAATGTGTGTCAGTTA |
| GGGTGTGGAAAGTCCCCAGGCTCCCCAGCAGGCAGAAGTATGCAAAGCATGCATCTCAATTAGTCAG |
| CAACCAGGTGTGGAAAGTCCCCAGGCTCCCCAGCAGGCAGAAGTATGCAAAGCATGCATCTCAATTA |
| GTCAGCAACCATAGTCCCGCCCCTAACTCCGCCCATCCCGCCCCTAACTCCGCCCAGTTCCGCCCAT |
| TCTCCGCCCCATGGCTGACTAATTTTTTTTATTTATGCAGAGGCCGAGGCCGCCTCTGCCTCTGAGC |
| TATTCCAGAAGTAGTGAGGAGGCTTTTTTGGAGGCCTAGGCTTTTGCAAAAAGCTCGATTCTTCTGA |
| CACTAGCGCCACCATGAAGAAGCCCGAACTCACCGCTACCAGCGTTGAAAAATTTCTCATCGAGAAG |
| TTCGACAGTGTGAGCGACCTGATGCAGTTGTCGGAGGGCGAAGAGAGCCGAGCCTTCAGCTTCGATG |
| TCGGCGGACGCGGCTATGTACTGCGGGTGAATAGCTGCGCTGATGGCTTCTACAAAGACCGCTACGT |
| GTACCGCCACTTCGCCAGCGCTGCACTACCCATCCCCGAAGTGTTGGACATCGGCGAGTTCAGCGAG |
| AGCCTGACATACTGCATCAGTAGACGCGCCCAAGGCGTTACTCTCCAAGACCTCCCCGAAACAGAGC |
| TGCCTGCTGTGTTACAGCCTGTCGCCGAAGCTATGGATGCTATTGCCGCCGCCGACCTCAGTCAAAC |
| CAGCGGCTTCGGCCCATTCGGGCCCCAAGGCATCGGCCAGTACACAACCTGGCGGGATTTCATTTGC |
| GCCATTGCTGATCCCCATGTCTACCACTGGCAGACCGTGATGGACGACACCGTGTCCGCCAGCGTAG |
| CTCAAGCCCTGGACGAACTGATGCTGTGGGCCGAAGACTGTCCCGAGGTGCGCCACCTCGTCCATGC |
| CGACTTCGGCAGCAACAACGTCCTGACCGACAACGGCCGCATCACCGCCGTAATCGACTGGTCCGAA |
| GCTATGTTCGGGGACAGTCAGTACGAGGTGGCCAACATCTTCTTCTGGCGGCCCTGGCTGGCTTGCA |
| TGGAGCAGCAGACTCGCTACTTCGAGCGCCGGCATCCCGAGCTGGCCGGCAGCCCTCGTCTGCGAGC |
| CTACATGCTGCGCATCGGCCTGGATCAGCTCTACCAGAGCCTCGTGGACGGCAACTTCGACGATGCT |
| GCCTGGGCTCAAGGCCGCTGCGATGCCATCGTCCGCAGCGGGGCCGGCACCGTCGGTCGCACACAAA |
| TCGCTCGCCGGAGCGCAGCCGTATGGACCGACGGCTGCGTCGAGGTGCTGGCCGACAGCGGCAACCG |

-continued

INFORMAL SEQUENCE LISTING

CCGGCCCAGTACACGACCGCGCGCTAAGGAGGTAGGTCGAGTTTAAACTCTAGAACCGGTCATGGCC

GCAATAAAATATCTTTATTTTCATTACATCTGTGTGTTGGTTTTTTGTGTGTTCGAACTAGATGCTG

TCGACCGATGCCCTTGAGAGCCTTCAACCCAGTCAGCTCCTTCCGGTGGGCGCGGGGCATGACTATC

GTCGCCGCACTTATGACTGTCTTCTTTATCATGCAACTCGTAGGACAGGTGCCGGCAGCGCTCTTCC

GCTTCCTCGCTCACTGACTCGCTGCGCTCGGTCGTTCGGCTGCGGCGAGCGGTATCAGCTCACTCAA

AGGCGGTAATACGGTTATCCACAGAATCAGGGGATAACGCAGGAAAGAACATGTGAGCAAAAGGCCA

GCAAAAGGCCAGGAACCGTAAAAAGGCCGCGTTGCTGGCGTTTTTCCATAGGCTCCGCCCCCCTGAC

GAGCATCACAAAAATCGACGCTCAAGTCAGAGGTGGCGAAACCCGACAGGACTATAAAGATACCAGG

CGTTTCCCCCTGGAAGCTCCCTCGTGCGCTCTCCTGTTCCGACCCTGCCGCTTACCGGATACCTGTC

CGCCTTTCTCCCTTCGGGAAGCGTGGCGCTTTCTCATAGCTCACGCTGTAGGTATCTCAGTTCGGTG

TAGGTCGTTCGCTCCAAGCTGGGCTGTGTGCACGAACCCCCCGTTCAGCCCGACCGCTGCGCCTTAT

CCGGTAACTATCGTCTTGAGTCCAACCCGGTAAGACACGACTTATCGCCACTGGCAGCAGCCACTGG

TAACAGGATTAGCAGAGCGAGGTATGTAGGCGGTGCTACAGAGTTCTTGAAGTGGTGGCCTAACTAC

GGCTACACTAGAAGAACAGTATTTGGTATCTGCGCTCTGCTGAAGCCAGTTACCTTCGGAAAAAGAG

TTGGTAGCTCTTGATCCGGCAAACAAACCACCGCTGGTAGCGGTGGTTTTTTGTTTGCAAGCAGCA

GATTACGCGCAGAAAAAAAGGATCTCAAGAAGATCCTTTGATCTTTTCTACGGGGTCTGACGCTCAG

TGGAACGAAAACTCACGTTAAGGGATTTTGGTCATGAGATTATCAAAAAGGATCTTCACCTAGATCC

TTTTAAATTAAAAATGAAGTTTTAAATCAATCTAAAGTATATATGAGTAAACTTGGTCTGACAGCGG

CCGCAAATGCTAAACCACTGCAGTGGTTACCAGTGCTTGATCAGTGAGGCACCGATCTCAGCGATCT

GCCTATTTCGTTCGTCCATAGTGGCCTGACTCCCCGTCGTGTAGATCACTACGATTCGTGAGGGCTT

ACCATCAGGCCCCAGCGCAGCAATGATGCCGCGAGAGCCGCGTTCACCGGCCCCGATTTGTCAGCA

ATGAACCAGCCAGCAGGGAGGGCCGAGCGAAGAAGTGGTCCTGCTACTTTGTCCGCCTCCATCCAGT

CTATGAGCTGCTGTCGTGATGCTAGAGTAAGAAGTTCGCCAGTGAGTAGTTTCCGAAGAGTTGTGGC

CATTGCTACTGGCATCGTGGTATCACGCTCGTCGTTCGGTATGGCTTCGTTCAACTCTGGTTCCCAG

CGGTCAAGCCGGGTCACATGATCACCCATATTATGAAGAAATGCAGTCAGCTCCTTAGGGCCTCCGA

TCGTTGTCAGAAGTAAGTTGGCCGCGGTGTTGTCGCTCATGGTAATGGCAGCACTACACAATTCTCT

TACCGTCATGCCATCCGTAAGATGCTTTTCCGTGACCGGCGAGTACTCAACCAAGTCGTTTTGTGAG

TAGTGTATACGGCGACCAAGCTGCTCTTGCCCGGCGTCTATACGGGACAACACCGCGCCACATAGCA

GTACTTTGAAAGTGCTCATCATCGGGAATCGTTCTTCGGGGCGGAAAGACTCAAGGATCTTGCCGCT

ATTGAGATCCAGTTCGATATAGCCCACTCTTGCACCCAGTTGATCTTCAGCATCTTTTACTTTCACC

AGCGTTTCGGGGTGTGCAAAAACAGGCAAGCAAAATGCCGCAAAGAAGGGAATGAGTGCGACACGAA

AATGTTGGATGCTCATACTCGTCCTTTTTCAATATTATTGAAGCATTTATCAGGGTTACTAGTACGT

CTCTCAAGGATAAGTAAGTAATATTAAGGTACGGGAGGTATTGGACAGGCCGCAATAAAATATCTTT

ATTTTCATTACATCTGTGTGTTGGTTTTTTGTGTGAATCGATAGTACTAACATACGCTCTCCATCAA

AACAAAACGAAACAAAACAAACTAGCAAAATAGGCTGTCCCCAGTGCAAGTGCAGGTGCCAGAACAT

TTCTCT

What is claimed is:

1. A RNA construct comprising the following operably linked polynucleotide elements in the 5' to 3' direction:
   i) a hammerhead ribozyme catalytic core;
   ii) a first hairpin ribozyme cleavage site in the antisense orientation;
   iii) a non-functional or stuffer polynucleotide;
   iv) a second hairpin ribozyme cleavage site in the antisense orientation;
   v) a hairpin ribozyme catalytic core in the antisense orientation;
   vi) reverse and forward primer annealing sites in the antisense orientation; and
   vii) an inserted polynucleotide suspected of comprising a RNA promoter.

2. The RNA construct of claim 1, wherein the hammerhead ribozyme catalytic core is from a hammerhead ribozyme selected from the group consisting of Type I, Type II, Type III, HH9 and HH10.

3. The RNA construct of claim 1, wherein the first and/or second hairpin ribozyme cleavage sites have a polynucleotide selected from the group of SEQ ID NO:7 and SEQ ID NO:6.

4. The RNA construct of claim 1, wherein the hairpin ribozyme catalytic core is derived from the negative strand self-cleavage domain of a plant virus satellite RNA selected from the group consisting of the satellite RNA of tobacco ringspot virus (sTRSV), the satellite RNA of *arabis* mosaic virus (sArMV), and the satellite RNA of chicory yellow mottle virus (sCYMV).

5. The RNA construct of claim 1, wherein the hairpin ribozyme catalytic core is derived from the negative strand self-cleavage domain of the satellite RNA of tobacco ringspot virus (sTRSV).

6. The RNA construct of claim 1, wherein the hairpin ribozyme catalytic core comprises a polynucleotide selected from the group of polynucleotides consisting of SEQ ID NO:8, SEQ ID NO:3, SEQ ID NO:4 and SEQ ID NO:5.

7. The RNA construct of claim 1, wherein the inserted polynucleotide suspected of comprising a RNA promoter is a promotor selected from the group consisting of cDNA of a RNA virus genome, a promotor from genomic DNA, a mutagenized RNA promoter and a library of randomized chemically synthesized DNA sequences.

8. A host cell comprising the RNA construct of claim 1, wherein the host cell expresses a RNA-dependent RNA polymerase.

9. The host cell of claim 8, wherein the host cell is transfected with a polynucleotide that encodes an exogenous RNA-dependent RNA polymerase.

10. A method of identifying a RNA promoter comprising the steps of:
    a) providing the RNA construct of claim 5;
    b) transfecting a host cell with the RNA construct, wherein the host cell expresses a RNA-dependent RNA polymerase and rolling circle transcription of the RNA construct within the host cell when the inserted polynucleotide comprises a functional RNA promoter yields a circularized RNA comprising:
       i) a hammerhead ribozyme catalytic core in the antisense orientation;
       ii) a ribozyme cleavage site;
       iii) a hairpin ribozyme catalytic core;
       iv) reverse and forward primer annealing sites; and
       v) the inserted polynucleotide comprising a functional RNA promoter;
    c) isolating the circularized RNA;
    d) amplifying the inserted polynucleotide comprising a functional RNA promoter; and
    e) sequencing the inserted polynucleotide comprising a functional RNA promoter, thereby identifying the RNA promoter.

11. The method of claim 10, wherein the host cell is infected with a RNA virus.

12. The method of claim 11, wherein the host cell is infected with a RNA virus from a virus taxonomic Order selected from the group consisting of Mononegavirales, Nidovirales, Picornavirales, and Tymovirales.

13. The method of claim 11, wherein the host cell is infected with a RNA virus from a virus taxonomic Group selected from the group of arenaviridae, astroviridae, bamaviridae, benyviridae, bromoviridae, bunyaviridae, caliciviridae, carmotetraviridae, closteroviridae, flaviviridae, hepeviridae, leviviridae, luteoviridae, namaviridae, nodaviridae, ophioviridae, orthomyxoviridae, permutotetraviridae, potyviridae, toga viridae, tombusviridae, virgaviridae.

14. The method of claim 11, wherein the host cell is infected with a RNA virus from a virus taxonomic Family selected from a group of celivirus, deltavirus, emaravirus, higrevirus, idaeovirus, ourmiavirus, polemovirus, sobemovirus, tenuivirus, umbravirus, or varicosavirus.

* * * * *